US012595285B2

(12) United States Patent
Zhang et al.

(10) Patent No.: US 12,595,285 B2
(45) Date of Patent: *Apr. 7, 2026

(54) LMP-1 EXPRESSING CELLS AND METHODS OF USE THEREOF

(71) Applicant: Dana-Farber Cancer Institute, Inc., Boston, MA (US)

(72) Inventors: Baochun Zhang, Newton, MA (US); Il-Kyu Choi, Boston, MA (US); Zhe Wang, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 792 days.

This patent is subject to a terminal disclaimer.

(21) Appl. No.: 17/663,344

(22) Filed: May 13, 2022

(65) Prior Publication Data

US 2022/0362296 A1     Nov. 17, 2022

Related U.S. Application Data

(63) Continuation of application No. 16/322,812, filed as application No. PCT/US2017/045089 on Aug. 2, 2017, now Pat. No. 11,369,635.

(60) Provisional application No. 62/532,622, filed on Jul. 14, 2017, provisional application No. 62/506,281, filed on May 15, 2017, provisional application No. 62/370,011, filed on Aug. 2, 2016.

(51) Int. Cl.

| | |
|---|---|
| *C07K 14/005* | (2006.01) |
| *A01K 67/0278* | (2024.01) |
| *A61K 35/17* | (2025.01) |
| *A61K 35/768* | (2015.01) |
| *A61K 40/11* | (2025.01) |
| *A61K 40/13* | (2025.01) |
| *A61K 40/32* | (2025.01) |
| *A61K 40/42* | (2025.01) |
| *A61K 45/06* | (2006.01) |
| *A61P 35/00* | (2006.01) |
| *C12N 15/62* | (2006.01) |
| *C12N 15/85* | (2006.01) |

(52) U.S. Cl.
CPC ........ *C07K 14/005* (2013.01); *A01K 67/0278* (2013.01); *A61K 35/17* (2013.01); *A61K 35/768* (2013.01); *A61K 40/11* (2025.01); *A61K 40/32* (2025.01); *A61K 40/42* (2025.01); *A61K 45/06* (2013.01); *A61P 35/00* (2018.01); *C12N 15/62* (2013.01); *C12N 15/85* (2013.01); *A01K 2217/072* (2013.01); *A01K 2227/105* (2013.01); *A01K 2267/0331* (2013.01); *A61K 2239/31* (2023.05); *A61K 2239/38* (2023.05); *A61K 2239/48* (2023.05); *C12N 2710/16222* (2013.01); *C12N 2740/10043* (2013.01)

(58) Field of Classification Search
CPC ...... C07K 14/005; A61K 40/42; A61K 40/13; A61K 35/17
See application file for complete search history.

(56) References Cited

U.S. PATENT DOCUMENTS

| | | | |
|---|---|---|---|
| 7,235,392 B2 * | 6/2007 | Platz | C12N 7/00 435/235.1 |
| 11,369,635 B2 * | 6/2022 | Zhang et al. | A61K 35/17 |
| 2007/0196389 A1 | 8/2007 | Caligiuri et al. | |
| 2012/0107319 A1 | 5/2012 | Ooka | |

FOREIGN PATENT DOCUMENTS

| | | |
|---|---|---|
| DE | 102014001771 A1 | 8/2015 |
| WO | WO 2007/131182 A2 | 11/2007 |

OTHER PUBLICATIONS

Termini, James (2014) "Latent Membrane Protein-1 as a Vaccine Adjuvant", Dissertation, University of Miami, 87 pages. (Year: 2014).*

Zhang et al. (2012) "Immune surveillance and therapy of lymphomas driven by Epstein-Barr virus protein LMP1 in a mouse model" Cell, 148(4), 739-751. (Year: 2012).*

Singavi et al. (2015) "Post-transplant lymphoproliferative disorders" In: Evens, A., Blum, K. (eds) Non-Hodgkin Lymphoma, Cancer Treatment and Research, vol. 165, pp. 305-327, Springer, Cham. (Year: 2015).*

YP_401722.1, "LMP1 [Human herpesvirus 4]", entry dated: Nov. 5, 2013, available from: National Library of Medicine (US), National Center for Biotechnology Information. (Year: 2013).*

Choi et al. (2018) "Signaling by the Epstein-Barr virus LMP1 protein induces potent cytotoxic CD4+ and CD8+ T cell responses" Proceedings of the National Academy of Sciences, 115(4), E686-E695. (Year: 2018).*

Yao et al. (2001) "Interleukin-18 expression induced by Epstein-Barr virus-infected cells" Journal of Leukocyte Biology, 69(5), 779-784. (Year: 2001).*

Yasuda et al. (2013) "Studying Epstein-Barr virus pathologies and immune surveillance by reconstructing EBV infection in mice" In Cold Spring Harbor symposia on quantitative biology, vol. 78, pp. 259-263, Cold Spring Harbor Laboratory Press. (Year: 2013).*

Batzer et al., "Enhanced evolutionary PCR using oligonucleotides with inosine at the 3'-terminus", *Nucleic Acid Research* 19(18):5081 (1991).

(Continued)

*Primary Examiner* — James Joseph Graber
(74) *Attorney, Agent, or Firm* — Mueting Raasch Group

(57) ABSTRACT

The disclosure provides immunogenic cells expressing LMP1, and use thereof in activating T cells and treating cancer. Also provided are methods of producing the immunogenic cells.

15 Claims, 31 Drawing Sheets

Specification includes a Sequence Listing.

(56) References Cited

OTHER PUBLICATIONS

Blankenstein et al., "The determinants of tumour immunogenicity", *Nature Reviews Cancer* 12(4):307-313 (2012).

Cheng et al., "A Gfp reporter system to assess gene transfer and expression in human hematopoietic progenitor cells", *Gene Therapy* 4(10):1013-1022 (1997).

Coulie et al., "Tumour antigens recognized by T lymphocytes: at the core of cancer immunotherapy", *Nature Reviews Cancer* 14(2):135-146 (2014).

Curran et al., "Systemic 4-1BB activation induces a novel T cell phenotype driven by high expression of Eomesodermin", *The Journal of Experimental Medicine* 210(4):743-755 (2013).

European Search Report and Search Opinion received for EP Application No. 17837602.6, mailed on Dec. 3, 2019, 7 pages.

Genbank Accession No. NP_001104569 updated Mar. 19, 2019.

Genbank Accession No. NP_001159878 updated Feb. 22, 2019.

Genbank Accession No. NP_033819 updated Feb. 9, 2019.

Genbank Accession No. NP_034269 updated Feb. 23, 2019.

Genbank Accession No. YP_401722 updated Aug. 13, 2018.

He et al., "A sensitive flow cytometry-based cytotoxic T-lymphocyte assay through detection of cleaved caspase 3 in target cells", *Journal of Immunological Methods* 304(1-2):43-59 (2005).

Homig-Holzel et al., "Constitutive CD40 signaling in B cells selectively activates the noncanonical NF-κB pathway and promotes lymphomagenesis", *The Journal of Experimental Medicine* 205(6):1317-1329 (2008).

International Search Report with Written Opinion for PCT/US2017/045089 dated Oct. 12, 2017.

Kaye et al., "Epstein-Barr virus latent membrane protein 1 is essential for B-lymphocyte growth transformation", *PNAS USA* 90(19):9150-9154 (1993).

Koralov et al., "Dicer Ablation Affects Antibody Diversity and Cell Survival in the B Lymphocytic Lineage", *Cell* 132:860-874 (2008).

Mehl et al., "Characterization of Intercellular Adhesion Molecule-1 Regulation by Epstein-Barr Virus-encoded Latent Membrane Protein-1 Identifies Pathways That Cooperate with Nuclear κB to Activate Transcription", *The Journal of Biological Chemistry* 276(2):984-992 (2001).

NCBI Gene ID No. 958 updated Feb. 13, 2019.

NCBI Gene ID No. 21939 updated Mar. 5, 2019.

NCBI Gene ID No. 3783750 updated Mar. 17, 2019.

Ohtsuka et al., "An Alternative Approach to Deoxyoligonucleotides as Hybridization Probes by Insertion of Deoxyinosine at Ambiguous Codon Positions", *The Journal of Biological Chemistry* 260(5):2605-2608 (1985).

Qui et al., "CD134 Plus CD137 Dual Costimulation Induces Eomesodermin in CD4 T Cells To Program Cytotoxic Th1 Differentiation", *The Journal of Immunology* 187:3555-3564 (2011).

Rossolini et al., "Use of deoxyinosine-containing primers vs degenerate primers for polymerase chain reaction based on ambiguous sequence information", *Molecular and Cellular Probes* 8:91-98 (1994).

Rowe et al., "Restoration of endogenous antigen processing in Burkitt's lymphoma cells by Epstein-Barr virus latent membrane protein-1: coordinate up-regulation of peptide transporters and HLA-class I antigen expression", *European Journal of Immunology* 25:1374-1384 (1995).

Schultze et al., "Follicular lymphomas can be induced to present alloantigen efficiently: A conceptual model to improve their tumor immunogenicity," *PNAS USA* 92:8200-8204 (1995).

Schultze et al., "Autologous Tumor Infiltrating T Cells Cytotoxic for Follicular Lymphoma Cells Can Be Expanded In Vitro", *Blood* 89(10):3806-3816 (1997).

Smith et al., "Discerning regulation of cis- and trans-presentation of CD8+ T-cell epitopes by EBV-encoded oncogene LMP-1 through self-aggregation", *Blood* 113:6148-6152 (2009).

Swain et al., "Expanding roles for CD4(+) T cells in immunity to viruses", *Nature Reviews Immunology* 12:136-148 (2012).

Termini "Latent Membrane Protein-1 as a Vaccine Adjuvant", Phd dissertation, University of Miami, published Apr. 28, 2014.

Yasuda et al., "Studying Epstein-Barr Virus Pathologies and Immune Surveillance by Reconstructing EBV Infection in Mice", *Cold Spring Harbor Symposia on Quantitative Biology* 78:259-263 (2013).

Yasui et al., "Latent infection membrane protein transmembrane FWLY is critical for intermolecular interaction, raft localization, and signaling", *PNAS USA* 101:278-283 (2004).

Yu et al., "A precise excision of the complete Epstein-Barr virus genome in a plasmid based on a bacterial artificial chromosome", *Journal of Virology Methods* 176(1-2):103-107 (2011).

Zhang et al., "Immune Surveillance and Therapy of Lymphomas Driven by Epstein-Barr-Virus Protein LMP1 in a Mouse Model", *Cell* 148(4):739-51 (2012).

Zhang et al., "An Oncogenic Role for Alternative NF-κB Signaling in DLBCL Revealed Upon Deregulated BCL6 Expression", *Cell Reports* 11(5):715-726 (2015).

International Preliminary Report on Patentability for International Application No. PCT/US2017/045089, mailed Feb. 14, 2019, 6 Pages.

* cited by examiner

Figure 13A

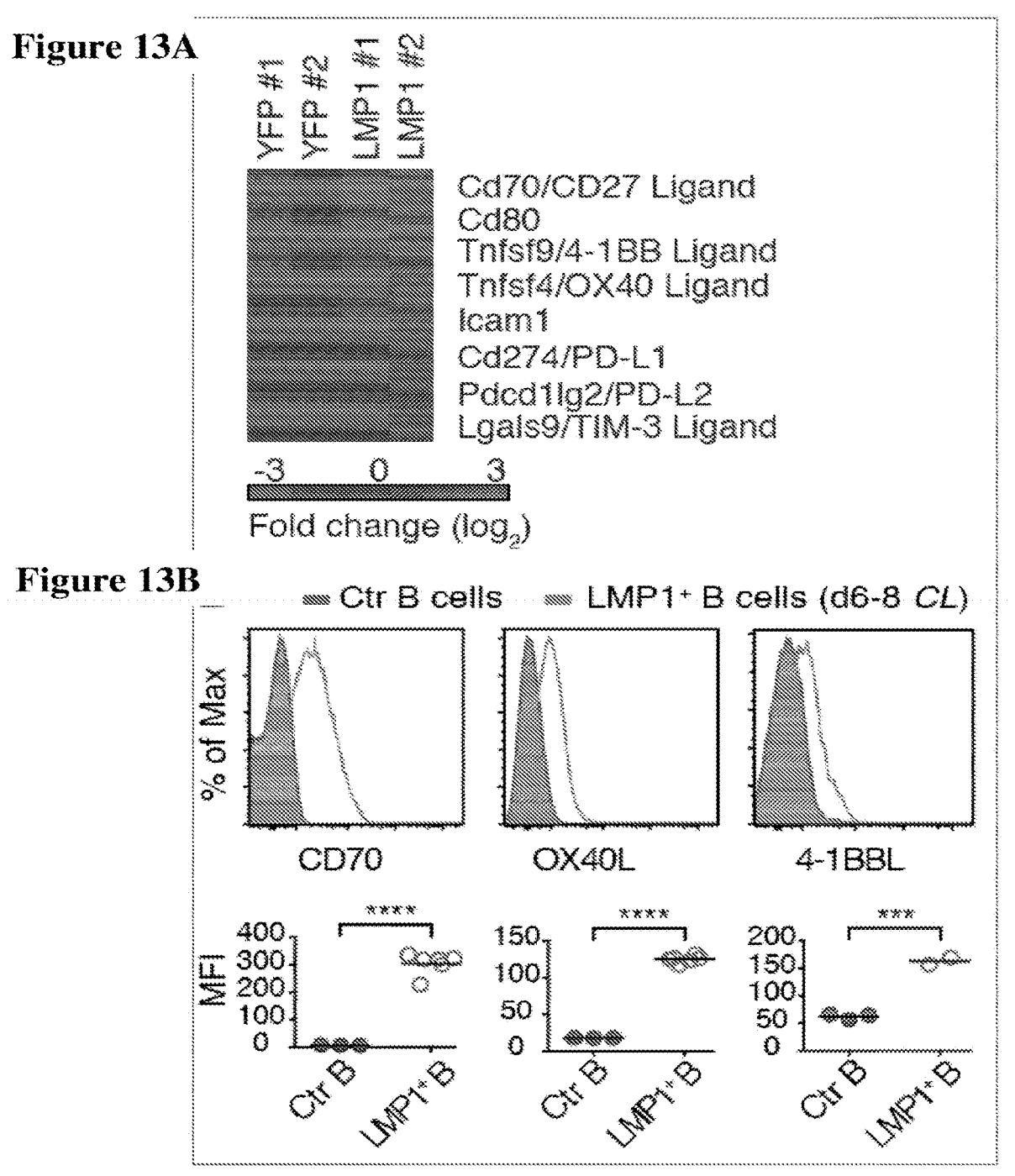

YFP #1
YFP #2
LMP1 #1
LMP1 #2

Cd70/CD27 Ligand
Cd80
Tnfsf9/4-1BB Ligand
Tnfsf4/OX40 Ligand
Icam1
Cd274/PD-L1
Pdcd1lg2/PD-L2
Lgals9/TIM-3 Ligand -3    0    3
Fold change (log$_2$)

Figure 13B

— Ctr B cells    — LMP1$^+$ B cells (d6-8 *CL*)

% of Max

CD70    OX40L    4-1BBL

MFI

****

Ctr B    LMP1$^+$ B

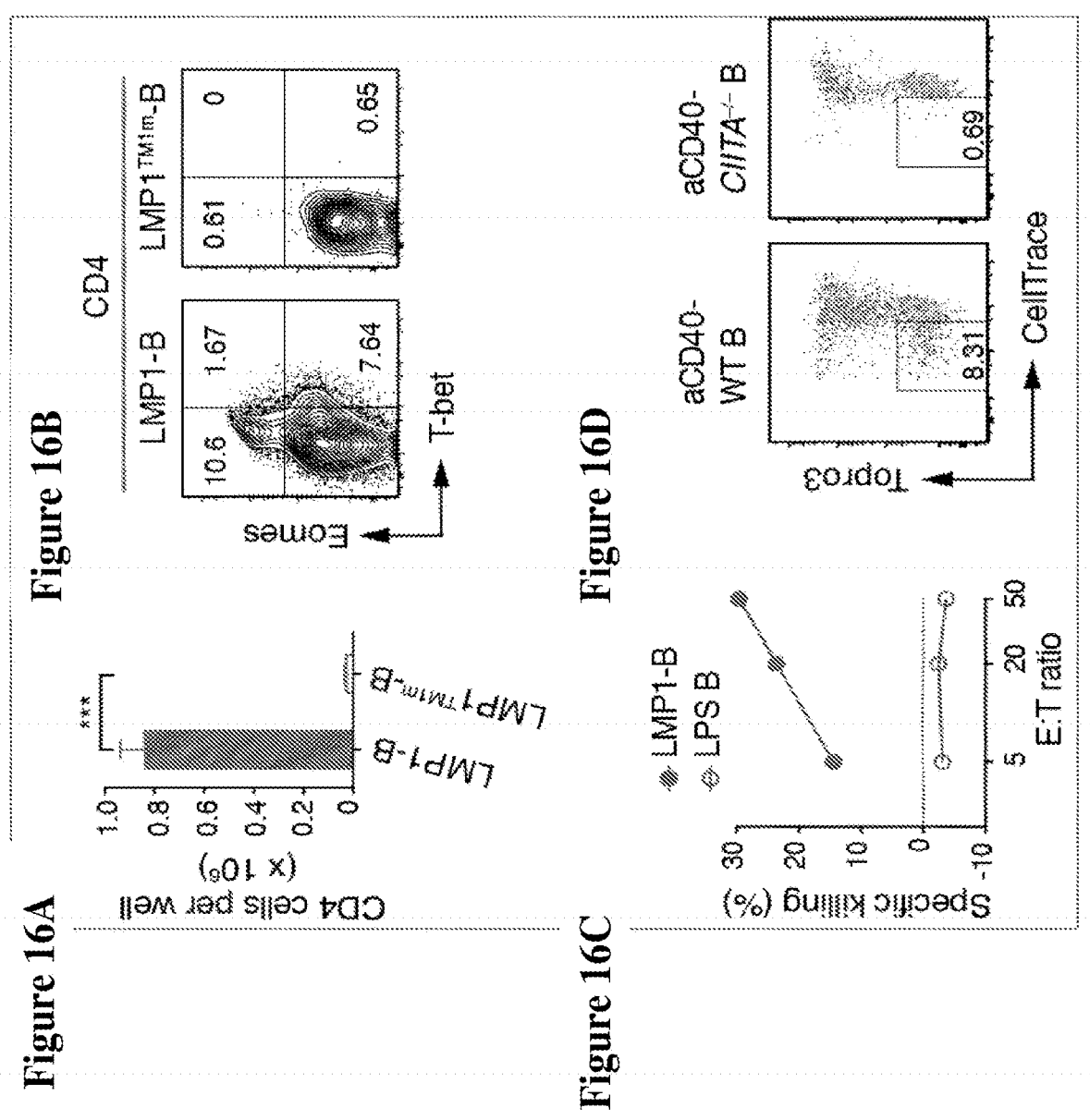

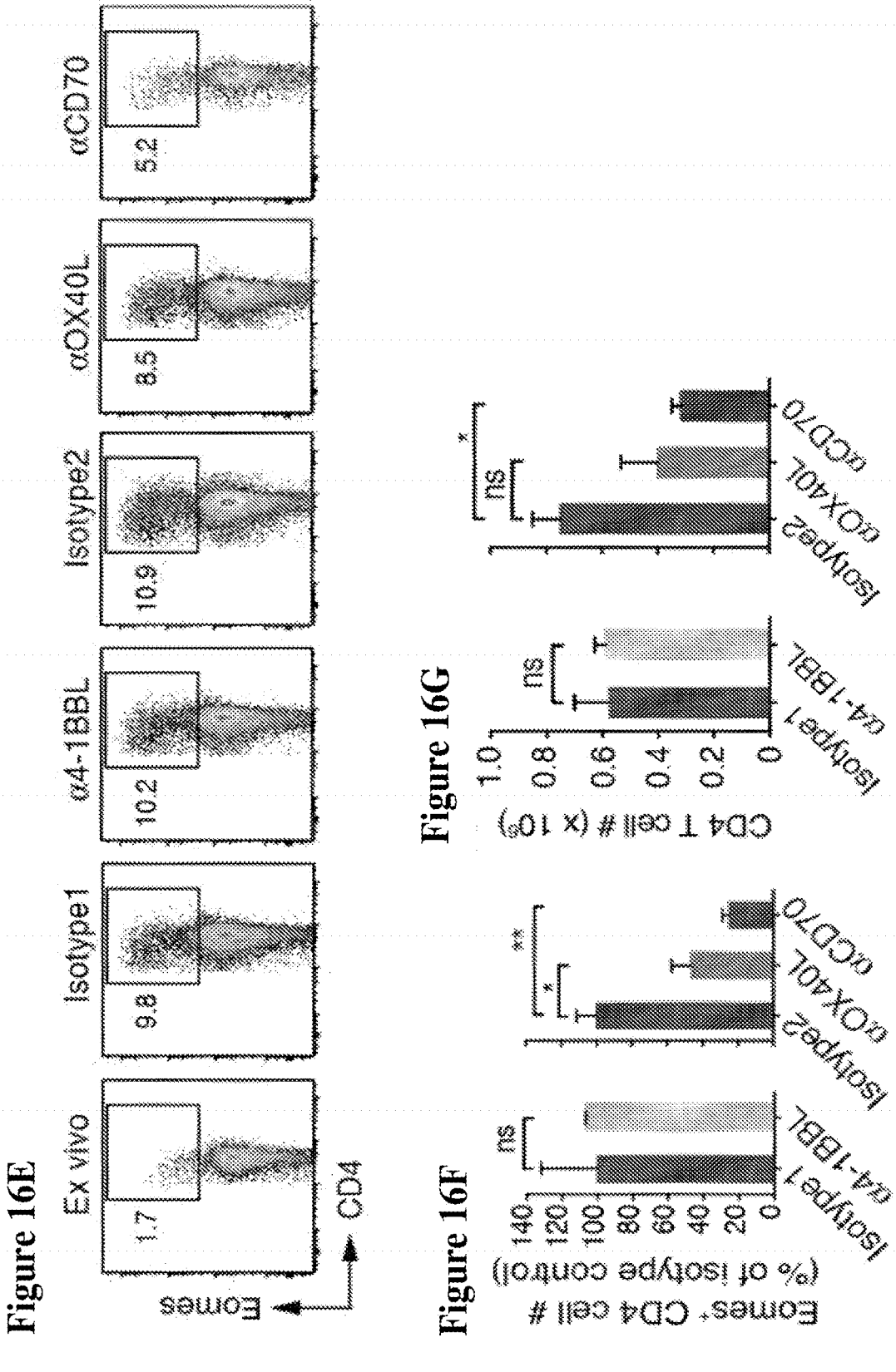

Figure 20A
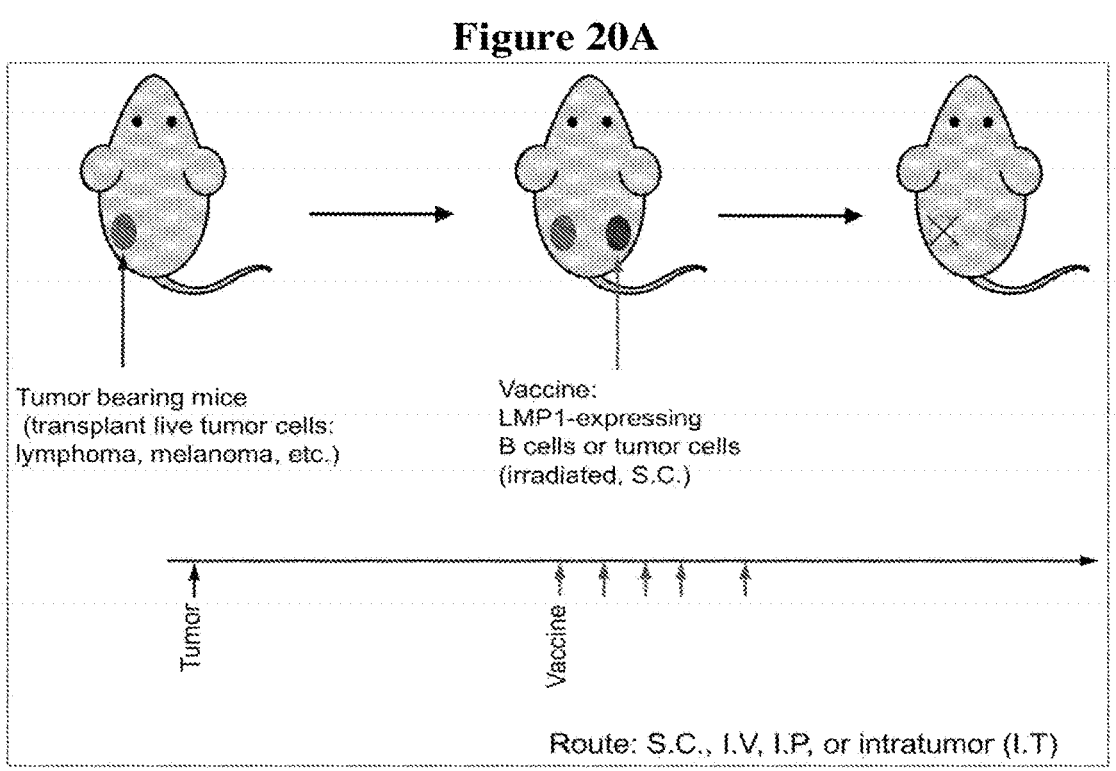
Figure 20B
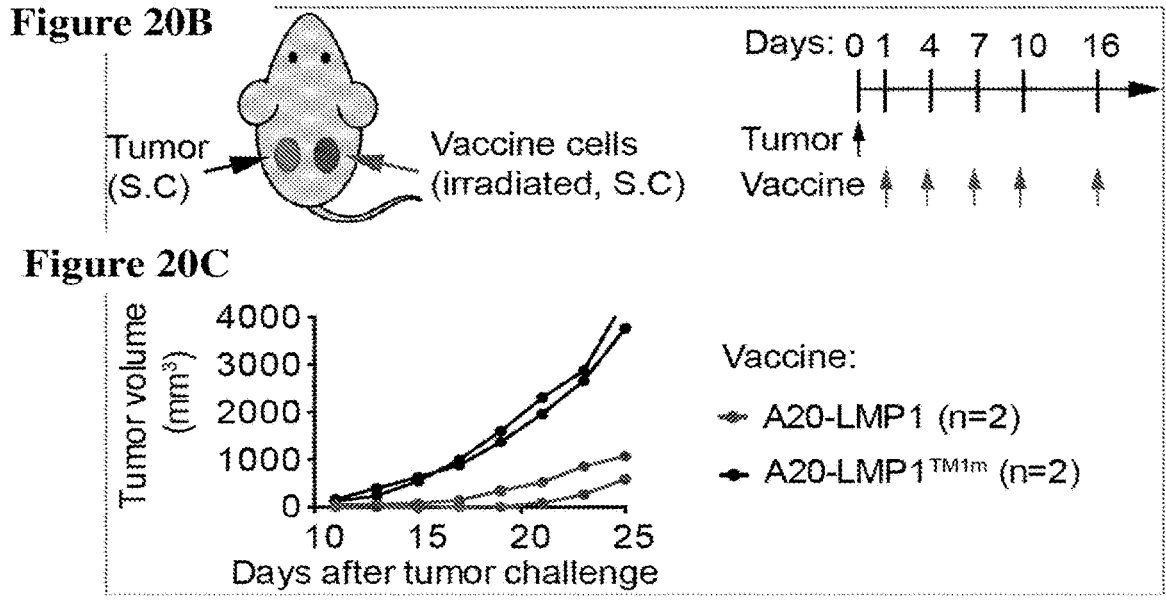
Figure 20C

SEQUENCE LISTING

<160> NUMBER OF SEQ ID NOS: 5

<210> SEQ ID NO 1
<211> LENGTH: 386
<212> TYPE: PRT
<213> ORGANISM: Human herpesvirus 4

<400> SEQUENCE: 1

```
Met Glu His Asp Leu Glu Arg Gly Pro Pro Gly Pro Arg Arg Pro Pro
1               5                   10                  15

Arg Gly Pro Pro Leu Ser Ser Ser Leu Gly Leu Ala Leu Leu Leu Leu
```

-continued

```
           20              25              30
Leu Leu Ala Leu Leu Phe Trp Leu Tyr Ile Val Met Ser Asp Trp Thr
       35              40              45
Gly Gly Ala Leu Leu Val Leu Tyr Ser Phe Ala Leu Met Leu Ile Ile
       50              55              60
Ile Ile Leu Ile Ile Phe Ile Phe Arg Arg Asp Leu Leu Cys Pro Leu
65              70              75              80
Gly Ala Leu Cys Ile Leu Leu Leu Met Ile Thr Leu Leu Leu Ile Ala
           85              90              95
Leu Trp Asn Leu His Gly Gln Ala Leu Phe Leu Gly Ile Val Leu Phe
       100             105             110
Ile Phe Gly Cys Leu Leu Val Leu Gly Ile Trp Ile Tyr Leu Leu Glu
       115             120             125
Met Leu Trp Arg Leu Gly Ala Thr Ile Trp Gln Leu Leu Ala Phe Phe
       130             135             140
Leu Ala Phe Phe Leu Asp Leu Ile Leu Leu Ile Ile Ala Leu Tyr Leu
145             150             155             160
Gln Gln Asn Trp Trp Thr Leu Leu Val Asp Leu Leu Trp Leu Leu Leu
           165             170             175
Phe Leu Ala Ile Leu Ile Trp Met Tyr Tyr His Gly Gln Arg His Ser
       180             185             190
Asp Glu His His His Asp Asp Ser Leu Pro His Pro Gln Gln Ala Thr
       195             200             205
Asp Asp Ser Gly His Glu Ser Asp Ser Asn Ser Asn Glu Gly Arg His
       210             215             220
His Leu Leu Val Ser Gly Ala Gly Asp Gly Pro Pro Leu Cys Ser Gln
225             230             235             240
Asn Leu Gly Ala Pro Gly Gly Gly Pro Asp Asn Gly Pro Gln Asp Pro
           245             250             255
Asp Asn Thr Asp Asp Asn Gly Pro Gln Asp Pro Asp Asn Thr Asp Asp
           260             265             270
Asn Gly Pro His Asp Pro Leu Pro Gln Asp Pro Asp Asn Thr Asp Asp
       275             280             285
Asn Gly Pro Gln Asp Pro Asp Asn Thr Asp Asp Asn Gly Pro His Asp
       290             295             300
Pro Leu Pro His Ser Pro Ser Asp Ser Ala Gly Asn Asp Gly Gly Pro
305             310             315             320
Pro Gln Leu Thr Glu Glu Val Glu Asn Lys Gly Gly Asp Gln Gly Pro
           325             330             335
Pro Leu Met Thr Asp Gly Gly Gly Gly His Ser His Asp Ser Gly His
           340             345             350
Gly Gly Gly Asp Pro His Leu Pro Thr Leu Leu Leu Gly Ser Ser Gly
       355             360             365
Ser Gly Gly Asp Asp Asp Asp Pro His Gly Pro Val Gln Leu Ser Tyr
       370             375             380
Tyr Asp
385
```

<210> SEQ ID NO 2
<211> LENGTH: 159
<212> TYPE: PRT
<213> ORGANISM: Mus musculus

<400> SEQUENCE: 2

```
Met Ser Asn Pro Gly Asp Val Arg Pro Val Pro His Arg Ser Lys Val
1               5                   10                  15

Cys Arg Cys Leu Phe Gly Pro Val Asp Ser Glu Gln Leu Arg Arg Asp
            20                  25                  30

Cys Asp Ala Leu Met Ala Gly Cys Leu Gln Glu Ala Arg Glu Arg Trp
        35                  40                  45

Asn Phe Asp Phe Val Thr Glu Thr Pro Leu Glu Gly Asn Phe Val Trp
    50                  55                  60

Glu Arg Val Arg Ser Leu Gly Leu Pro Lys Val Tyr Leu Ser Pro Gly
65                  70                  75                  80

Ser Arg Ser Arg Asp Asp Leu Gly Gly Asp Lys Arg Pro Ser Thr Ser
                85                  90                  95

Ser Ala Leu Leu Gln Gly Pro Ala Pro Glu Asp His Val Ala Leu Ser
            100                 105                 110

Leu Ser Cys Thr Leu Val Ser Glu Arg Pro Glu Asp Ser Pro Gly Gly
        115                 120                 125

Pro Gly Thr Ser Gln Gly Arg Lys Arg Gln Thr Ser Leu Thr Asp
    130                 135                 140

Phe Tyr His Ser Lys Arg Arg Leu Val Phe Cys Lys Arg Lys Pro
145                 150                 155
```

<210> SEQ ID NO 3
<211> LENGTH: 140
<212> TYPE: PRT
<213> ORGANISM: Mus musculus

<400> SEQUENCE: 3

```
Met Gly Ala Pro Ala Leu Pro Gln Ile Trp Gln Leu Tyr Leu Lys Asn
1               5                   10                  15

Tyr Arg Ile Ala Thr Phe Lys Asn Trp Pro Phe Leu Glu Asp Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Asn Pro Ile Glu Glu His Arg Lys His
65                  70                  75                  80

Ser Pro Gly Cys Ala Phe Leu Thr Val Lys Lys Gln Met Glu Glu Leu
                85                  90                  95

Thr Val Ser Glu Phe Leu Lys Leu Asp Arg Gln Arg Ala Lys Asn Lys
            100                 105                 110

Ile Ala Lys Glu Thr Asn Asn Lys Gln Lys Glu Phe Glu Glu Thr Ala
        115                 120                 125

Lys Thr Thr Arg Gln Ser Ile Glu Gln Leu Ala Ala
    130                 135                 140
```

<210> SEQ ID NO 4
<211> LENGTH: 977
<212> TYPE: PRT
<213> ORGANISM: Mus musculus

<400> SEQUENCE: 4

```
Met Glu Leu Arg Ala Val Gly Phe Cys Leu Ala Leu Leu Trp Gly Cys
1               5                   10                  15

Ala Leu Ala Ala Ala Ala Ala Gln Gly Lys Glu Val Val Leu Leu Asp
            20                  25                  30
```

-continued

```
Phe Ala Ala Met Lys Gly Glu Leu Gly Trp Leu Thr His Pro Tyr Gly
        35              40                  45

Lys Gly Trp Asp Leu Met Gln Asn Ile Met Asp Asp Met Pro Ile Tyr
    50              55                  60

Met Tyr Ser Val Cys Asn Val Val Ser Gly Asp Gln Asp Asn Trp Leu
65                  70                  75                  80

Arg Thr Asn Trp Val Tyr Arg Glu Glu Ala Glu Arg Ile Phe Ile Glu
            85                  90                  95

Leu Lys Phe Thr Val Arg Asp Cys Asn Ser Phe Pro Gly Gly Ala Ser
            100                 105                 110

Ser Cys Lys Glu Thr Phe Asn Leu Tyr Tyr Ala Glu Ser Asp Val Asp
        115                 120                 125

Tyr Gly Thr Asn Phe Gln Lys Arg Gln Phe Thr Lys Ile Asp Thr Ile
    130                 135                 140

Ala Pro Asp Glu Ile Thr Val Ser Ser Asp Phe Glu Ala Arg Asn Val
145                 150                 155                 160

Lys Leu Asn Val Glu Glu Arg Met Val Gly Pro Leu Thr Arg Lys Gly
            165                 170                 175

Phe Tyr Leu Ala Phe Gln Asp Ile Gly Ala Cys Val Ala Leu Leu Ser
            180                 185                 190

Val Arg Val Tyr Tyr Lys Lys Cys Pro Glu Met Leu Gln Ser Leu Ala
        195                 200                 205

Arg Phe Pro Glu Thr Ile Ala Val Ala Val Ser Asp Thr Gln Pro Leu
        210                 215                 220

Ala Thr Val Ala Gly Thr Cys Val Asp His Ala Val Val Pro Tyr Gly
225                 230                 235                 240

Gly Glu Gly Pro Leu Met His Cys Thr Val Asp Gly Glu Trp Leu Val
            245                 250                 255

Pro Ile Gly Gln Cys Leu Cys Gln Glu Gly Tyr Glu Lys Val Glu Asp
            260                 265                 270

Ala Cys Arg Ala Cys Ser Pro Gly Phe Phe Lys Ser Glu Ala Ser Glu
        275                 280                 285

Ser Pro Cys Leu Glu Cys Pro Glu His Thr Leu Pro Ser Thr Glu Gly
    290                 295                 300

Ala Thr Ser Cys Gln Cys Glu Glu Gly Tyr Phe Arg Ala Pro Glu Asp
305                 310                 315                 320

Pro Leu Ser Met Ser Cys Thr Arg Pro Pro Ser Ala Pro Asn Tyr Leu
            325                 330                 335

Thr Ala Ile Gly Met Gly Ala Lys Val Glu Leu Arg Trp Thr Ala Pro
            340                 345                 350

Lys Asp Thr Gly Gly Arg Gln Asp Ile Val Tyr Ser Val Thr Cys Glu
        355                 360                 365

Gln Cys Trp Pro Glu Ser Gly Glu Cys Gly Pro Cys Glu Ala Ser Val
    370                 375                 380

Arg Tyr Ser Glu Pro Pro His Ala Leu Thr Arg Thr Ser Val Thr Val
385                 390                 395                 400

Ser Asp Leu Glu Pro His Met Asn Tyr Thr Phe Ala Val Glu Ala Arg
            405                 410                 415

Asn Gly Val Ser Gly Leu Val Thr Ser Arg Ser Phe Arg Thr Ala Ser
            420                 425                 430

Val Ser Ile Asn Gln Thr Glu Pro Pro Lys Val Arg Leu Glu Asp Arg
        435                 440                 445

Ser Thr Thr Ser Leu Ser Val Thr Trp Ser Ile Pro Val Ser Gln Gln
```

-continued

```
            450              455              460

Ser Arg Val Trp Lys Tyr Glu Val Thr Tyr Arg Lys Lys Gly Asp Ala
465              470              475              480

Asn Ser Tyr Asn Val Arg Arg Thr Glu Gly Phe Ser Val Thr Leu Asp
                485              490              495

Asp Leu Ala Pro Asp Thr Thr Tyr Leu Val Gln Val Gln Ala Leu Thr
                500              505              510

Gln Glu Gly Gln Gly Ala Gly Ser Lys Val His Glu Phe Gln Thr Leu
            515              520              525

Ser Thr Glu Gly Ser Ala Asn Met Ala Val Ile Gly Gly Val Ala Val
            530              535              540

Gly Val Val Leu Leu Leu Val Leu Ala Gly Val Gly Leu Phe Ile His
545              550              555              560

Arg Arg Arg Arg Asn Leu Arg Ala Arg Gln Ser Ser Glu Asp Val Arg
                565              570              575

Phe Ser Lys Ser Glu Gln Leu Lys Pro Leu Lys Thr Tyr Val Asp Pro
            580              585              590

His Thr Tyr Glu Asp Pro Asn Gln Ala Val Leu Lys Phe Thr Thr Glu
            595              600              605

Ile His Pro Ser Cys Val Ala Arg Gln Lys Val Ile Gly Ala Gly Glu
            610              615              620

Phe Gly Glu Val Tyr Lys Gly Thr Leu Lys Ala Ser Ser Gly Lys Lys
625              630              635              640

Glu Ile Pro Val Ala Ile Lys Thr Leu Lys Ala Gly Tyr Thr Glu Lys
                645              650              655

Gln Arg Val Asp Phe Leu Ser Glu Ala Ser Ile Met Gly Gln Phe Ser
                660              665              670

His His Asn Ile Ile Arg Leu Glu Gly Val Val Ser Lys Tyr Lys Pro
            675              680              685

Met Met Ile Ile Thr Glu Tyr Met Glu Asn Gly Ala Leu Asp Lys Phe
            690              695              700

Leu Arg Glu Lys Asp Gly Glu Phe Ser Val Leu Gln Leu Val Gly Met
705              710              715              720

Leu Arg Gly Ile Ala Ser Gly Met Lys Tyr Leu Ala Asn Met Asn Tyr
                725              730              735

Val His Arg Asp Leu Ala Ala Arg Asn Ile Leu Val Asn Ser Asn Leu
                740              745              750

Val Cys Lys Val Ser Asp Phe Gly Leu Ser Arg Val Leu Glu Asp Asp
            755              760              765

Pro Glu Ala Thr Tyr Thr Thr Ser Gly Gly Lys Ile Pro Ile Arg Trp
            770              775              780

Thr Ala Pro Glu Ala Ile Ser Tyr Arg Lys Phe Thr Ser Ala Ser Asp
785              790              795              800

Val Trp Ser Tyr Gly Ile Val Met Trp Glu Val Met Thr Tyr Gly Glu
                805              810              815

Arg Pro Tyr Trp Glu Leu Ser Asn His Glu Val Met Lys Ala Ile Asn
                820              825              830

Asp Gly Phe Arg Leu Pro Thr Pro Met Asp Cys Pro Ser Ala Ile Tyr
            835              840              845

Gln Leu Met Met Gln Cys Trp Gln Gln Glu Arg Ser Arg Arg Pro Lys
            850              855              860

Phe Ala Asp Ile Val Ser Ile Leu Asp Lys Leu Ile Arg Ala Pro Asp
865              870              875              880
```

-continued

```
Ser Leu Lys Thr Leu Ala Asp Phe Asp Pro Arg Val Ser Ile Arg Leu
                885                 890                 895

Pro Ser Thr Ser Gly Ser Glu Gly Val Pro Phe Arg Thr Val Ser Glu
                900                 905                 910

Trp Leu Glu Ser Ile Lys Met Gln Gln Tyr Thr Glu His Phe Met Val
                915                 920                 925

Ala Gly Tyr Thr Ala Ile Glu Lys Val Val Gln Met Ser Asn Glu Asp
        930                 935                 940

Ile Lys Arg Ile Gly Val Arg Leu Pro Gly His Gln Lys Arg Ile Ala
945                 950                 955                 960

Tyr Ser Leu Leu Gly Leu Lys Asp Gln Val Asn Thr Val Gly Ile Pro
                965                 970                 975

Ile

<210> SEQ ID NO 5
<211> LENGTH: 887
<212> TYPE: PRT
<213> ORGANISM: Mus musculus

<400> SEQUENCE: 5

Met Ser His Arg Ile Leu Ser Pro Pro Ala Gly Leu Leu Ser Asp Glu
1               5                   10                  15

Asp Val Val Asp Ser Pro Ile Leu Glu Ser Thr Ala Ala Asp Leu Arg
                20                  25                  30

Ser Val Val Arg Lys Asp Leu Leu Ser Asp Cys Ser Val Ile Ser Ala
        35                  40                  45

Ser Leu Glu Asp Lys Gln Ala Leu Leu Glu Asp Thr Ser Glu Lys Val
        50                  55                  60

Lys Val Tyr Leu Arg Ile Arg Pro Phe Leu Thr Ser Glu Leu Asp Arg
65                  70                  75                  80

Gln Glu Asp Gln Gly Cys Val Cys Ile Glu Asn Thr Glu Thr Leu Val
                85                  90                  95

Leu Gln Ala Pro Lys Asp Ser Phe Ala Leu Lys Ser Asn Glu Arg Gly
                100                 105                 110

Val Gly Gln Ala Thr His Lys Phe Thr Phe Ser Gln Ile Phe Gly Pro
        115                 120                 125

Glu Val Gly Gln Val Ala Phe Phe Asn Leu Thr Met Lys Glu Met Val
        130                 135                 140

Lys Asp Val Leu Lys Gly Gln Asn Trp Leu Ile Tyr Thr Tyr Gly Val
145                 150                 155                 160

Thr Asn Ser Gly Lys Thr Tyr Thr Ile Gln Gly Thr Ser Lys Asp Ala
                165                 170                 175

Gly Ile Leu Pro Gln Ser Leu Ala Leu Ile Phe Asn Ser Leu Gln Gly
                180                 185                 190

Gln Leu His Pro Thr Pro Asp Leu Lys Pro Leu Leu Ser Asn Glu Val
        195                 200                 205

Ile Trp Leu Asp Ser Lys Gln Ile Arg Gln Glu Glu Met Lys Lys Leu
        210                 215                 220

Ser Leu Leu Ile Gly Gly Leu Gln Glu Glu Glu Leu Ser Thr Ser Val
225                 230                 235                 240

Lys Lys Arg Val His Thr Glu Ser Arg Ile Gly Ala Ser Asn Ser Phe
                245                 250                 255

Asp Ser Gly Val Ala Gly Leu Ser Ser Thr Ser Gln Phe Thr Ser Ser
        260                 265                 270
```

-continued

```
Ser Gln Leu Asp Glu Thr Ser Gln Leu Trp Ala Gln Pro Asp Thr Val
    275                 280                 285

Pro Val Ser Val Pro Ala Asp Ile Arg Phe Ser Val Trp Ile Ser Phe
    290                 295                 300

Phe Glu Ile Tyr Asn Glu Leu Leu Tyr Asp Leu Leu Glu Pro Pro Ser
305                 310                 315                 320

His Gln His Lys Arg Gln Thr Leu Arg Leu Cys Glu Asp Gln Asn Gly
                325                 330                 335

Asn Pro Tyr Val Lys Asp Leu Asn Trp Ile His Val Arg Asp Val Glu
                340                 345                 350

Glu Ala Trp Lys Leu Leu Lys Val Gly Arg Lys Asn Gln Ser Phe Ala
                355                 360                 365

Ser Thr His Met Asn Gln Gln Ser Ser Arg Ser His Ser Ile Phe Ser
    370                 375                 380

Ile Arg Ile Leu His Leu Gln Gly Glu Gly Asp Ile Val Pro Lys Ile
385                 390                 395                 400

Ser Glu Leu Ser Leu Cys Asp Leu Ala Gly Ser Glu Arg Cys Lys His
                405                 410                 415

Gln Lys Ser Gly Glu Arg Leu Lys Glu Ala Gly Asn Ile Asn Thr Ser
                420                 425                 430

Leu His Thr Leu Gly Arg Cys Ile Ala Ala Leu Arg Gln Asn Gln Gln
    435                 440                 445

Asn Arg Ser Lys Gln Asn Leu Ile Pro Phe Arg Asp Ser Lys Leu Thr
    450                 455                 460

Arg Val Phe Gln Gly Phe Phe Thr Gly Arg Gly Arg Ser Cys Met Ile
465                 470                 475                 480

Val Asn Val Asn Pro Cys Ala Ser Thr Tyr Asp Glu Thr Leu His Ala
                485                 490                 495

Ala Lys Phe Ser Ala Leu Ala Ser Gln Leu Val His Ala Pro Pro Val
                500                 505                 510

His Leu Gly Ile Pro Ser Leu His Ser Phe Ile Lys Lys His Ser Pro
    515                 520                 525

Gln Val Gly Pro Gly Leu Glu Lys Glu Asp Lys Ala Asp Ser Asp Leu
    530                 535                 540

Glu Asp Ser Pro Glu Asp Glu Ala Asp Val Ser Val Tyr Gly Lys Glu
545                 550                 555                 560

Glu Leu Leu Gln Val Val Glu Ala Met Lys Ala Leu Leu Leu Lys Glu
                565                 570                 575

Arg Gln Glu Lys Leu Gln Leu Glu Ile Gln Leu Arg Glu Glu Ile Cys
                580                 585                 590

Asn Glu Met Val Glu Gln Met Gln Gln Arg Glu Gln Trp Cys Ser Glu
    595                 600                 605

Arg Leu Asp Asn Gln Lys Glu Leu Met Glu Glu Leu Tyr Glu Glu Lys
    610                 615                 620

Leu Lys Ile Leu Lys Glu Ser Leu Thr Thr Phe Tyr Gln Glu Gln Ile
625                 630                 635                 640

Gln Glu Arg Asp Glu Lys Ile Glu Glu Leu Glu Thr Leu Leu Gln Glu
                645                 650                 655

Ala Lys Gln Gln Pro Ala Ala Gln Gln Ser Gly Gly Leu Ser Leu Leu
                660                 665                 670

Arg Arg Ser Gln Arg Leu Ala Ala Ser Ala Ser Thr Gln Gln Phe Gln
    675                 680                 685
```

-continued

```
Glu Val Lys Ala Glu Leu Glu Gln Cys Lys Thr Glu Leu Ser Ser Thr
    690             695         700

Thr Ala Glu Leu His Lys Tyr Gln Gln Val Leu Lys Pro Pro Pro Pro
705             710             715             720

Ala Lys Pro Phe Thr Ile Asp Val Asp Lys Lys Leu Glu Glu Gly Gln
            725             730             735

Lys Asn Ile Arg Leu Leu Arg Thr Glu Leu Gln Lys Leu Gly Gln Ser
            740             745             750

Leu Gln Ser Ala Glu Arg Ala Cys Cys His Ser Thr Gly Ala Gly Lys
        755             760             765

Leu Arg Gln Ala Leu Thr Asn Cys Asp Asp Ile Leu Ile Lys Gln Asn
    770             775             780

Gln Thr Leu Ala Glu Leu Gln Asn Asn Met Val Leu Val Lys Leu Asp
785             790             795             800

Leu Gln Lys Lys Ala Ala Cys Ile Ala Glu Gln Tyr His Thr Val Leu
            805             810             815

Lys Leu Gln Gly Gln Ala Ser Ala Lys Lys Arg Leu Gly Ala Asn Gln
            820             825             830

Glu Asn Gln Gln Pro Asn His Gln Pro Pro Gly Lys Lys Pro Phe Leu
        835             840             845

Arg Asn Leu Leu Pro Arg Thr Pro Thr Cys Gln Ser Ser Thr Asp Ser
    850             855             860

Ser Pro Tyr Ala Arg Ile Leu Arg Ser Arg His Ser Pro Leu Leu Lys
865             870             875             880

Ser Pro Phe Gly Lys Lys Tyr
            885
```

LMP-1 EXPRESSING CELLS AND METHODS OF USE THEREOF

RELATED APPLICATIONS

This application claims the benefit of U.S. Provisional Application Nos. 62/370,011, filed Aug. 2, 2016; 62/506,281, filed May 15, 2017; and 62/532,622, filed Jul. 14, 2017, each of which is incorporated by reference herein in its entirety.

FIELD OF INVENTION

The present invention relates generally to methods of immunotherapy strategy, more specifically Adoptive Cell Transfer Therapy strategy and Vaccination strategy, for treatment of cancer. The present invention also relates to methods of activating and expanding cytotoxic T cells with diverse TCR repertoire against a broad array of tumor-associated antigens (TAAs) and neoantigens in a simple and speedy way using an isolated cell engineered to express LMP1.

BACKGROUND

Preclinical and clinical developments have shown that cancer immunotherapy represents powerful means to battle with and even cure the disease. However, only small fractions of patients of most cancer types can benefit from current immunotherapy approaches. These include three main approaches: 1) extracting patient's immune system T cells and adding to them a selected T cell receptor (TCR) in a native or modified form to recognize a protein marker (called antigen) on cancer cells and kill them, a strategy referred to as adoptive cell transfer therapy (ACT); 2) pre-sensitizing the immune system with a protein antigen known to be expressed on cancer cells, a process called vaccination; 3) reinvigorating anti-tumor immunity through immune co-stimulation and/or immune checkpoint blockade. A major hurdle limiting the efficacy of current ACT and vaccination approaches is that only a single or few tumor antigens are being targeted, which often allows antigen-negative/loss tumor variants to escape. Checkpoint blockade therapies require pre-existing tumor antigen-specific T cells, lack of which may account for the failure of this approach in many patients. Clearly, a key task for better cancer immunotherapy is to find ways to raise T cells against broad-spectrum tumor antigens.

Epstein-Barr virus (EBV), also known as human herpes virus 4 (HHV-4), is a potent tumor virus. EBV specifically infects and transforms human B cells, but also some epithelial cells. EBV-infected B cells are rapidly eliminated by T cells, but EBV acquires a dormant state in a minute fraction of B cells, establishing a life-long latent infection in more than 90% of human beings. Under conditions of immunosuppression, EBV can spread from these few cells, resulting in explosive expansion of infected B cells and their malignant transformation. Expression of EBV-encoded latent membrane protein 1 (LMP1) is essential for the transformation of human B cells by EBV and can by itself induce oncogenic transformation of rodent fibroblasts. It has been reported that, in a transgenic mouse model, LMP1-positive B cell lymphomas sporadically develop in aged mice, yet LMP1 expression is barely detectable at young age, a phenomenon not well understood. Therefore, it would desirable to develop B cell specific LMP1 transgenic mouse model that can be used to study EBV-induced immune surveillance and lymphomagenesis.

SUMMARY

The present disclosure provides methods of immunotherapy strategy, more specifically Adaptive Cell Transfer Therapy strategy and Vaccination strategy, for treatment of cancer.

In one aspect, the present disclosure provides a vector comprising a nucleic acid, wherein the nucleic acid encodes a polypeptide comprising a sequence at least 90% identical to SEQ ID NO: 1, wherein at least 50% of an Epstein-Barr virus (EBV) genome is absent from the vector.

In some embodiments, the vector comprises a promoter operably linked to the nucleic acid encoding the polypeptide comprising a sequence at least 90% identical to SEQ ID NO: 1. In some embodiments, the vector is an expression vector. In some embodiments, the vector is a non-viral vector. In some embodiments, the vector is a viral vector. In some embodiments, the viral vector is selected from the group consisting of an adenoviral vector, an adeno-associated viral vector, and a retroviral vector. In some embodiments, the retroviral vector is a lentiviral vector. In some embodiments, the retroviral vector is a murine stem cell virus (MSCV) vector.

In another aspect, the present disclosure provides a viral particle comprising the viral vector as described herein.

In another aspect, the present disclosure provides a method of producing an immunogenic cell, the method comprising contacting an isolated cell with a vector described herein, thereby producing an immunogenic cell.

In some embodiments, the isolated cell is a B cell. In some embodiments, the B cell is a naïve B cell. In some embodiments, the B cell is a neoplastic B cell. In some embodiments, the B cell is a B cell lymphoma cell or B cell leukemia cell. In some embodiments, the B cell is isolated from a subject with a pathology selected from the group consisting of Hodgkin's lymphoma, Burkitt's lymphoma, and AIDS-associated B cell lymphoma, a central nervous system lymphoma, a post-transplant lymphoproliferative disorder (PTLD), and a diffuse large B cell lymphoma. In some embodiments, the B cell is an A20 lymphoma cell. In some embodiments, the immunogenic cell comprises at least one antigen on the surface. In some embodiments, the antigen is a tumor-associated antigen (TAA).

In some embodiments, the isolated cell is a non-B cell. In some embodiments, the non-B cell is a cancer cell. In some embodiments, the cancer is selected from the group consisting of melanoma, gastric cancer, and nasopharyngeal carcinoma. In some embodiments, the cancer cell is a solid tumor cell. In some embodiments, the solid tumor cell is a B16 melanoma cell. In some embodiments, the immunogenic cell comprises at least one antigen on the surface. In some embodiments, the antigen is selected from the group consisting of a TAA and a neoantigen. In some embodiments, the TAA is selected from the group consisting of Cdkn1a (p21), Birc5 (Survivin), Epha2, Kif20a. In some embodiments, the TAA is a peptide comprising at least 8 contiguous amino acids of a sequence selected from the group consisting of SEQ ID NOs: 2-5.

In some embodiments, the antigen is conjugated to an MHC. In some embodiments, the MHC is selected from the group consisting of MHC I, MHC II, HLA-A, HLA-B, HLA-C, HLA-DPA1, HLA-DPB1, HLA-DQA1, HLA-DQB1, HLA-DRα, and HLA-DRβ. In some embodiments, the MHC is a MHC-I. In some embodiments, the MHC-I is H-2D$^b$ and H-2K$^b$. In some embodiments, the MHC is a MHC-II. In some embodiments, the MHC-II is I-A$^b$.

In some embodiments, the isolate cell has reduced proliferative capacity. In some embodiments, proliferation of the isolated cell is ceased. In some embodiments, the isolated cell is irradiated.

In some embodiments, the immunogenic cell has reduced proliferative capacity. In some embodiments, proliferation of the immunogenic cell is ceased. In some embodiments, the immunogenic cell is irradiated.

In some embodiments, LMP1 signaling activates endogenous antigen processing and presenting function in the cell. In some embodiments, the immunogenic cell expresses an enhanced level of a co-stimulatory molecule and/or an adhesion molecule relative to an isolated cell not contacted with the vector or viral particle. In some embodiments, the co-stimulatory molecule is selected from the group consisting of CD80, CD86, CD70, OX40 ligand, and 4-1BB ligand. In some embodiments, the adhesion molecule is CD54 (ICAM-1). In some embodiments, LMP1 signaling increases the amount of CD95/Fas on the cell surface.

In another aspect, the present disclosure provides an immunogenic cell produced by a method of producing immunogenic cells as described herein. In another aspect, the present disclosure provides an isolated cell comprising a vector as described herein. In another aspect, the instant disclosure provides an isolated cell comprising a viral particle as described herein.

In certain embodiments, the cell is a B cell. In some embodiments, the B cell is a naïve B cell. In some embodiments, the B cell is a neoplastic B cell. In some embodiments, the B cell is a B cell lymphoma cell isolated from a subject with a B cell lymphoma or a B cell isolated from a subject with a B cell leukemia. In some embodiments, the B cell is isolated from a subject with Hodgkin's lymphoma, Burkitt's lymphoma, and AIDS-associated B cell lymphoma, a central nervous system lymphoma, a post-transplant lymphoproliferative disorder (PTLD), and diffuse large B cell lymphoma. In some embodiments, the B cell is an A20 lymphoma cell. In some embodiments, the cell comprises at least one antigen on the surface. In some embodiments, the antigen is a TAA.

In some embodiments, the cell is a non-B cell. In some embodiments, the non-B cell is a cancer cell. In some embodiments, the cancer is selected from the group consisting of melanoma, gastric cancer, and nasopharyngeal carcinoma. In some embodiments, the cancer cell is a solid tumor cell. In some embodiments, the solid tumor cell is a B16 melanoma cell. In some embodiments, the cell comprises at least one antigen on the surface. In some embodiments, the antigen is selected from the group consisting of a TAA and a neoantigen. In some embodiments, the TAA is selected from the group consisting of Cdkn1a (p21), Birc5 (Survivin), Epha2, Kit20a. In some embodiments, the TAA is a peptide comprising at least 8 contiguous amino acids of a sequence selected from the group consisting of SEQ ID NOs: 2-5.

In some embodiments, the antigen is conjugated to an MHC. In some embodiments, the MHC is selected from the group consisting of MHC I, MHC II, HLA-A, HLA-B, HLA-C, HLA-DPA1, HLA-DPB1, HLA-DQA1, HLA-DQB1, HLA-DRα, and HLA-DRβ. In some embodiments, the MHC is a MHC-T. In some embodiments, the MHC-I is H-2D$^b$ and H-2K$^b$. In some embodiments, the MHC is a MHC-II. In some embodiments, the MHC-II is I-A$^b$.

In some embodiments, the cell has reduced proliferative capacity. In some embodiments, cell proliferation is ceased. In some embodiments, the cell is irradiated.

In some embodiments, LMP1 signaling activates endogenous antigen processing and presenting function in the cell. In some embodiments, the isolated cell expresses an enhanced level of a co-stimulatory molecule and/or an adhesion molecule relative to an isolated cell not comprising the vector or viral particle. In some embodiments, the co-stimulatory molecule is selected from the group consisting of CD80, CD86, CD70, CD27, OX40 ligand, OX40, 4-1BB ligand, 4-1BB, and GITR. In some embodiments, the adhesion molecule is CD54 (ICAM-1). In some embodiments, LMP1 signaling increases the amount of CD95/Fas on the cell surface.

In another aspect, the present disclosure provides a vaccine comprising a cell (e.g., isolated cell, immunogenic cell) as described herein. In some embodiments, the vaccine further comprises an adjuvant.

In another aspect, the present disclosure provides a method of activating a T cell, the method comprising contacting the T cell with (a) one or more isolated cells as described herein, or (b) a vaccine as described herein.

In some embodiments, the T cell is activated and becomes a cytotoxic T cell. In some embodiments, the activated T cell expresses a T cell receptor (TCR) that binds to a TAA and/or a neoantigen. In some embodiments, the T cell is a CD4$^+$ T cell. In some embodiments, the T cell is a CD8$^+$ T cell. In some embodiments, the cytotoxic T cell is cultured under suitable conditions that allow proliferation of the cytotoxic T cell. In some embodiments, the cytotoxic T cell is cultured for 3-14 days.

In some embodiments, the T cell is contacted with the isolated cells ex vivo. In some embodiments, the method further comprises administering the T cell to a subject in need thereof. In some embodiments, the subject has cancer. In some embodiments, the cancer is a lymphoma. In some embodiments, the T cell is autologous to the subject. In some embodiments, the T cell is from an MHC matched donor of the subject. In some embodiments, the isolated cell is autologous to the subject. In some embodiments, the isolated cell is from an MHC matched donor of the subject. In some embodiments, the subject is a human.

In another aspect, the present disclosure provides a T cell activated by a method of activating a T cell as described herein.

In another aspect, the present disclosure provides a method of treating a subject in need thereof, the method comprising administering to the subject (a) one or more isolated cells as described herein, or (b) a vaccine as described herein.

In some embodiments, the method further comprises irradiating the isolated cell. In some embodiments, the subject has cancer. In some embodiments, the cancer is a lymphoma. In some embodiments, the isolated cell is autologous to the subject. In some embodiments, the isolated cell is from an MHC matched donor of the subject. In some embodiments, the subject is a human. In some embodiments, the method further comprises administering to the subject an adjuvant. In some embodiments, the method further comprises administering to the subject an immune co-stimulation therapy. In certain embodiments, the immune co-stimulation therapy is selected from the group consisting of an agonist of CD27 (e.g., an agonistic antibody that specifically binds CD27), an agonist of OX40 (e.g., an agonistic antibody that specifically binds OX40), and an agonist of 4-1BB (e.g., an agonistic antibody that specifically binds 4-1BB). In certain embodiments, the method further comprises administering to the subject an immune checkpoint targeting therapy. In certain embodiments, the method further comprises administering to the subject a Treg modulating therapy.

BRIEF DESCRIPTION OF DRAWINGS

FIG. 13A is a heat map showing expression of co-stimulatory and co-inhibitory molecules in LMP1-expressing B cells compared to control B cells. Splenic B cells from LMP1$^{flSTOP}$/YFP$^{flSTOP}$ and YFP$^{flSTOP}$ mice (both on a CB6F1 background) were treated with TAT-Cre to generate LMP1-expressing B cells and YFP control B cells. All treated B cells were collected at day 2 post-treatment for array analysis.

FIG. 13B shows FACS plots (upper panel) and mean fluorescence intensities (MFI; lower panel) of the indicated co-stimulatory ligands in LMP1-expressing B cells from day 6-8 CL mice, compared to splenic B cells from WT control (ctr) mice. Data are representative of 2-6 mice analyzed for each group. The mice (CL and control) are on a CB6F1 background. Each symbol represents an individual mouse; bars show the respective mean values; **, p<0.0001; *, p<0.001 (unpaired two-tailed student's t-test).

FIG. 16A is a graph showing numbers (mean±SEM) of recovered T cells after co-culturing for 7 days with B cells expressing LMP1 or LMP1$^{TM1m}$. The cell culture was begun with 1.5×10$^6$ purified CD4 T cells together with the indicated B cells (irradiated at 500 RAD before co-culturing) at 1:1 ratio in triplicate wells of 12-well plates. No exogenous cytokines were added. ***, p<0.001 (unpaired two-tailed student's t-test). B cells and T cells are from 2-3 months old naïve WT B6 mice spleens.

FIG. 16B shows FACS analysis of Eomes and T-bet expression in CD4 cells co-cultured with the indicated B cells (as in (A)).

FIG. 16C is a graph showing cytotoxicity of CD4 cells expanded on LMP1-B cells (as in (A)) against B cells transduced with the MSCV-LMP1-IRES-GFP retrovirus, which contained GFP$^+$ (LMP1-B cells) and GFP$^-$ cells (not successfully transduced cells and thus representing LPS-activated B cells, see Materials and Methods; these cells served as control).

FIG. 16D shows proliferation of CD4 T cells expanded on LMP1-B cells (as in (A)) assayed on CD40-activated B cells from WT or CIITA$^{-/-}$ mice. Data in (A-D) are representative of 2-4 independent experiments using splenic B cells and T cells from 2-3 months old naïve WT B6 mice.

FIG. 16E shows FACS analysis of Eomes expression in CD4 cells either freshly isolated from naïve B6 mice (Ex vivo), or after co-culturing for 7 days with LMP1-B cells in the presence of the indicated blocking antibodies or corresponding isotype controls. Representative data from one of triplicate wells are shown, with the frequency of Eomes$^+$ cells in the gate.

FIG. 16F shows numbers (mean±SEM) of Eomes$^+$ CD4 cells recovered from culture wells treated with the indicated blocking antibodies relative to those from corresponding isotype control treated wells.

FIG. 16G shows numbers (mean±SEM) of recovered CD4 cells after co-culturing for 7 days with LMP1$^+$ B cells in the presence of the indicated blocking antibodies or corresponding isotype controls. The cell culture was begun with 1×10$^6$ purified CD4 T cells in triplicate wells of 24-well plates.

FIG. 20A shows a scheme depicting vaccination strategy with LMP1-expressing B cells or tumor cells for treatment of cancers.

FIG. 20B shows a vaccination scheme in which lymphoma cells are transduced to express LMP1 and used as vaccine to treat the unmodified (parental) B cell lymphoma.

FIG. 20C is a graph showing that vaccination with LMP1-expressing A20 lymphoma cells markedly delays tumor (A20) growth. A20 lymphoma cells expressing the signaling-dead mutant LMP1$^{TM1m}$ serve as control vaccine.

DETAILED DESCRIPTION

Figure 1A:
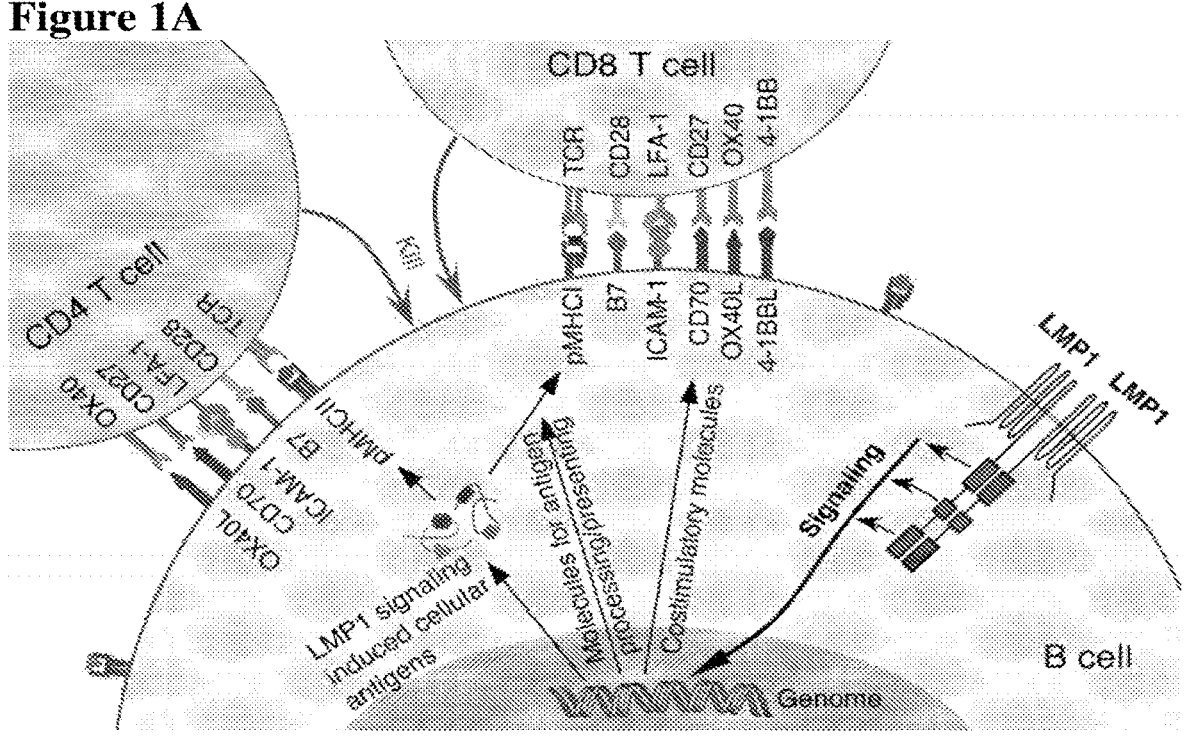
FIG. 1A is a schematic diagram showing that LMP1 signaling in B cells (e.g., primary B cells) induces expression and presentation of cellular antigens (including many TAAs), and enhances co-stimulation function, thereby eliciting potent polyclonal cytotoxic T cell responses. In B cells, constitutive LMP1 signaling induces massive cellular gene expression. This leads to upregulation of cellular machinery involved in antigen processing and presentation (e.g., MHCs), induction of strong co-stimulation signals (B7-1, B7-2, ICAM-1, and particularly CD70, OX40L and 4-1BBL), and induced and/or enhanced expression of certain cellular antigens (including a wide range of TAAs). Presentation of the LMP1 signaling-induced cellular antigens and simultaneous co-stimulations drive activation and cytotoxic differentiation of CD4$^+$ and CD8$^+$ T cells specific to these antigens. Thus, LMP1 signaling makes B cells hyperimmunogenic antigen-presenting cells (APCs).

Before the present compositions and methods are described, it is to be understood that this disclosure is not limited to particular compositions, methods, and experimental conditions described, as such compositions, methods, and conditions may vary. It is also to be understood that the terminology used herein is for purposes of describing particular embodiments only, and is not intended to be limiting, since the scope of the present disclosure will be limited only in the appended claims. It is readily apparent to one skilled in the art that various embodiments and modifications can be made to the disclosure of the present application without departing from the scope and spirit of the instant application.

In one aspect, the present disclosure provides a vector comprising a nucleic acid encoding LMP1. In certain embodiments, the amino acid sequence of LMP1 is at least 70%, 80%, 90%, 95%, or 99% identical to SEQ ID NO: 1. In certain embodiments, the vector is less than 50%, 60%, 70%, 80%, 90%, 95%, or 99% identical to an Epstein-Barr virus (EBV) genome. In certain embodiments, at least 50% of an Epstein-Barr virus (EBV) genome is absent from the expression vector.

In certain embodiments, the vector is an expression vector. In certain embodiments, the vector comprises a transcription regulatory element (e.g., a promoter and/or an enhancer) operably linked to the nucleic acid encoding the polypeptide.

In certain embodiments, the vector is a viral vector. In certain embodiments, the vector is a replication incompetent viral vector. In certain embodiments, the viral vector is packaged with one or more capsid proteins into a viral particle. In certain embodiments, the vector or the viral particle further comprises a polynucleotide encoding a polypeptide capable of inducing cell death. In certain embodiments, the polypeptide is a chimeric polypeptide comprising a multimerization (e.g., dimerization or oligomerization) region and a cell death-inducing region, wherein the cell death-inducing region is activated by multimerization. In certain embodiments, the cell death-inducing region comprises a sequence of a caspase (e.g., caspase-9) that has protease activity. In certain embodiments, the cell death-inducing region comprises the full-length human caspase-9 polypeptide. In certain embodiments, the cell death-inducing region comprises a truncated human caspase-9 polypeptide (e.g., wherein the CARD domain of caspase-9 is deleted).

In another aspect, the present disclosure provides a method of producing an immunogenic cell, the method comprising contacting an isolated cell with a vector (e.g., expression vector) described herein, thereby producing an immunogenic cell. In another aspect, the present disclosure provides an isolated cell comprising a vector (e.g., expression vector) described herein. Such cells exhibit superior efficiency of antigen presentation, because LMP1 signaling increases the expression of cellular machinery involved in antigen processing and presentation. Moreover, these cells are hyperimmunogenic, as LMP1 signaling increases the co-stimulation signals (e.g., CD70, OX40L, and 4-1BBL) on the cell surface.

Expression of LMP1 in an isolated cell described herein leads to expression and/or presentation of one or more antigens on the cell surface. Cytotoxic T cells can be generated by contacting with the isolated cell. The antigens include without limitation (1) LMP1 signaling-induced cellular antigens, which include many TAAs; (2) tumor (e.g., lymphoma) inherent TAAs; and (3) neoantigens, a group of mutation-derived tumor antigens which arise from tumor-specific mutations in expressed proteins.

In primary B cells, LMP1 signaling induces and/or enhances the expression of LMP1 signaling-induced cellular antigens, which includes many TAAs. Thus, relative to unmodified (LMP1-negative), non-immunogenic primary B cells, LMP1-expressing primary B cells increasingly express and present LMP1 signaling-induced cellular antigens on their surface, and are useful for activating T cells that express TCRs that bind to these antigens (FIG. 1A).

Figure 1B:
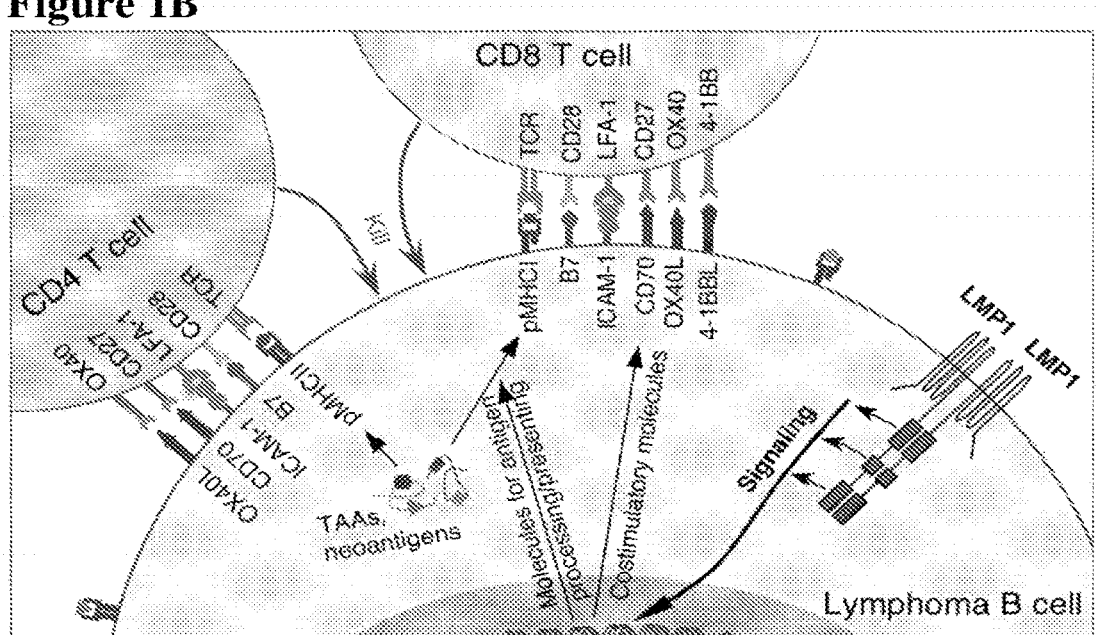
FIG. 1B is a schematic diagram showing that LMP1 signaling in lymphoma B cells enhances presentation of lymphoma inherent TAAs and neoantigens. Some of these lymphoma inherent TAAs are LMP1 signaling-induced TAAs, whose expression is enhanced by LMP1 signaling, whereas other lymphoma inherent TAAs are not. The increased antigen presentation along with enhanced co-stimulation signals leads to cytotoxic T cell responses against these tumor antigens. Thus, LMP1 signaling turns lymphoma B cells into hyperimmunogenic antigen-presenting cells (APCs).

In lymphoma B cells, LMP1 signaling increases the expression of LMP1 signaling-induced TAAs, a subgroup of lymphoma inherent TAAs. The expression of the other lymphoma inherent TAAs, as well as the neoantigens, is not induced or enhanced. Regardless of the expression levels, however, all these antigens are increasingly presented on the surface of LMP1-expressing lymphoma B cells, relative to the corresponding unmodified (LMP1-negative) lymphoma B cells. Therefore, LMP1-expressing lymphoma B cells are useful for activating T cells that express TCRs that bind to these lymphoma inherent neoantigens and TAAs (FIG. 1B).

Accordingly, in another aspect, the present disclosure provides a method of activating a T cell, the method comprising contacting the T cell with one or more isolated cells described herein. In certain embodiments, the method is used for cancer immunotherapy.

In certain embodiments, the isolated cell is a B cell. As described herein, LMP1 represents the first foreign protein capable of breaking immune tolerance when expressed as a transgene starting from early development. Constitutive LMP1 signaling in B cells induces massive cellular genes, leading to upregulation of antigen presenting function (MHCs), strong co-stimulatory signals (B7-1, B7-2, ICAM-1, and particularly CD70, OX40 ligand, and 4-1 BB ligand), and induced and/or enhanced expression of certain cellular antigens (termed here as LMP1 signaling-induced cellular antigens). Presentation of the LMP1 signaling-induced cellular antigens on MHCs (HLAs in humans) and simultaneous co-stimulation through CD70, OX40 ligand, and 4-1BB ligand drive activation and cytotoxic differentiation of CD4 and CD8 T cells specific to these antigens. Because LMP1 is the key oncoprotein for EBV-driven tumorigenesis, the LMP1 signaling-induced cellular antigens that are targeted by T cells would be various Tumor-Associated Antigens (TAAs, a group of non-mutated cellular antigens recognizable by T cells in certain tumors).

The isolated cells described herein express antigens (e.g., TAAs and neoantigens), which can be presented by MHCs (e.g., HLAs). Accordingly, in some embodiments, the isolated cells can be used to generate cytotoxic T cells with diverse TCR repertoire against wide range of TAAs and neoantigens in a simple and speedy way, without the need of identifying such TAAs and pairing with particular MHCs (e.g., HLAs). In certain embodiments, the isolated cells are patient-derived B cells or lymphoma cells. The unique strength of the therapeutic strategies described herein is that they can also be combined with immune co-stimulation therapies and/or immune checkpoint targeting therapies. Immune co-stimulation therapies and immune checkpoint targeting therapies rely on pre-existing tumor antigen-specific T cells, lack of which may have caused the failure of such therapies in many cancer patients. Therefore, the use of LMP1-expressing cells to activate T cells can bring more effective treatment to those who otherwise would fail immune co-stimulation therapies or immune checkpoint targeting therapies alone.

The activation of T cells by LMP1-expressing cells (e.g., B cells) could be dependent on the ability of CD70, OX40L, and 4-1BBL to engage CD27, OX40, and 4-1BB, respectively, on the T cells. In certain cancer patients, these stimulatory proteins may be down-regulated or defective. Accordingly, in some embodiments, a vaccination therapy using LMP1-expressing cells (e.g., B cells or tumor cells) or an adoptive cell transfer therapy (ACT) using T cells activated by LMP1-expressing cells (e.g., B cells or tumor cells) can be supplemented by an agonist of CD27, OX40, or 4-1BB. In some embodiment, the agonist is an agonistic antibody that specifically binds to CD27, OX40, or 4-1BB. The agonistic antibody can be in any format (e.g., tetrameric antibody comprising two heavy chains and two light chains, single-chain Fv, Fab fragment, $F(ab')_2$ fragment, bispecific antibody). In one embodiment, the agonistic anti-CD27 antibody is varlilumab. In one embodiment, the agonistic anti-OX40 antibody is selected from the group consisting of MOXR0916 (Genentech), MEDI6383 (MedImmune), and INCAGN1949 (Agenus). In one embodiment, the agonistic anti-4-1BB antibody is selected from the group consisting of urelumab/BMS-663513 (BMS) and PF-05082566 (Pfizer). In some embodiments, one, two, or three of these agonists are administered to a patient in need thereof.

In other embodiments, the immune checkpoint targeting therapy is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody and an IDO inhibitor, i.e., an agent that inhibits the enzymatic activity of IDO (indoleamine-(2,3)-dioxygenase) and/or TDO (tryptophan 2,3-dioxygenase).

In other embodiments, the immune checkpoint targeting therapy is an anti-PD-1 antibody, optionally wherein the anti-PD-1 antibody is pembrolizumab, nivolumab, Pidilizumab, MEDI0680, PDR001, REGN2810, PF-06801591, BGB-A317, TSR-042, or SHR-1210. In some embodiments, the immune checkpoint targeting therapy is an anti-PD-L1 antibody, optionally wherein the anti-PD-L1 antibody is atezolizumab, durvalumab, avelumab (MSB0010718C), MDX-1105, or AMP-224. In some embodiments, the immune checkpoint targeting therapy is an anti-CTLA-4 antibody, optionally wherein the anti-CTLA-4 antibody is ipilimumab. In some embodiments, the immune checkpoint targeting therapy is an IDO inhibitor, optionally wherein the IDO inhibitor is epacadostat, F001287, indoximod, or NLG919.

The activation of T cells by LMP1-expressing cells (e.g., B cells) could be controlled by Tregs (e.g., CD4 Tregs), particularly at a later chronic phase of the immune response, to achieve immune homeostasis. In certain cancer patients, the amount and activity of Tregs may be higher than in healthy individuals, and may be triggered at the earlier acute phase, which may limit the efficacy of a vaccination therapy using LMP1-expressing cells (e.g., B cells) or an adoptive cell transfer (ACT) therapy using T cells activated by LMP1-expressing cells (e.g., B cells). Accordingly, in some embodiments, a subject receiving or to receive the vaccination or ACT therapy can further receive administration of a Treg modulating therapy to inhibit or decrease the amount and activity of Tregs. Treg modulating therapies are known in the art, and include without limitation antibodies (e.g., full antibodies, and antigen-binding fragments thereof) that specifically bind to CTLA-4, GITR, CCR4, PD-1, LAG3, CD25, or CD15s. The Treg modulating therapy can be administered prior to, contemporaneously with (e.g., during the same doctor visit), or subsequent to the administration of the vaccination or ACT therapy. If the Treg modulating therapy is administered subsequent to the administration of the vaccination or ACT therapy, the patient's response to the vaccination or ACT therapy can be examined to determine the necessity and dose of the Treg modulating therapy.

In some embodiments, the isolated cells or T cells contacted therewith are administered in combination with an adjuvant. A variety of adjuvants may be employed, including, for example, systemic adjuvants and mucosal adjuvants. A systemic adjuvant is an adjuvant that can be delivered parenterally. Systemic adjuvants include adjuvants that create a depot effect, adjuvants that stimulate the immune system and adjuvants that do both. An adjuvant that creates a depot effect is an adjuvant that causes the antigen to be slowly released in the body, thus prolonging the exposure of immune cells to the antigen. In some embodiments, the adjuvant stimulate the immune system, for instance, cause an immune cell to produce and secrete cytokines or IgG. This class of adjuvants includes immunostimulatory nucleic acids, such as CpG oligonucleotides; saponins purified from the bark of the *Q. saponaria* tree, such as QS-21; poly[di (carboxylatophenoxy)phosphazene (PCPP polymer; Virus Research Institute, USA); RNA mimetics such as polyinosinic:polycytidylic acid (poly I:C) or poly I:C stabilized with poly-lysine (poly-ICLC [Hiltonol®; Oncovir, Inc.]; derivatives of lipopolysaccharides (LPS) such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.).

In some embodiments, the adjuvant is administered prior to, at about the same time as, or subsequent to the administration of the isolated cells or T cells. In some embodiments, the adjuvant is administered within the same patient visit as the administration of the isolated cells or T cells. In some embodiments, the adjuvant is administered in the same composition (e.g., vaccine) as the isolated cells or T cells. In some embodiments, the adjuvant is administered in a different composition from the isolated cells or T cells.

In one embodiment, the disclosure relates to expressing LMP1 using replication incompetent viral vectors or transfection in patient-derived B cells or lymphoma cells and using them to activate/expand T cells autologous or derived from a donor for Adoptive Cell Transfer (ACT) therapy. In some embodiments, the ACT is employed to a subject with EBV-associated B cell lymphoma. In some embodiments, the ACT is employed to an immunosuppressed patient, such as post-transplant and AIDS patients. In some embodiments, the subject has EBV-associated B cell lymphoma cells expressing LMP1, which may present the same array of antigens on their surface. In some embodiments, the cells are irradiated to have reduced proliferative capacity, as LMP1 is a potent oncogene. In certain embodiments, the proliferative capacity of the cells is reduced by irradiation.

The ACT strategy described herein can be similarly applied to EBV-associated B cell lymphomas in immunocompetent hosts, such as Burkitt lymphoma and Hodgkin lymphoma, or EBV-unrelated B cell lymphomas. These lymphoma cells share some TAAs with LMP1-expressing autologous B cells/lymphoma cells used for T cell activation/expansion. As described herein, an ACT strategy using LMP1-expressing lymphoma cells for producing therapeutic T cells, and for treating EBV-unrelated B cell lymphomas, can generate anti-tumor T cells against the array of lymphoma inherent TAAs and neoantigens (FIG. 1B), obviating the need to identify them and pair them with particular MHCs (e.g., HLAs). Such ACT strategies are suitable for generating therapeutic T cells against these lymphoma inherent antigens, because LMP1 signaling would enhance cell endogenous antigen presentation and co-stimulation, i.e., turning the lymphoma cells into hyperimmunogenic APCs.

ACT uses in vitro generated tumor antigen-reactive T cells to treat cancers. The strategy for ACT production has evolved over time, but has always involved complicated in vitro manipulations prior to the instant disclosure. Such manipulations include, for example, isolating tumor-reactive cytotoxic T lymphocytes (CTLs) from patients and subjecting them to extensive in vitro expansion/differentiation; introducing tumor-reactive TCRs into autologous T cells by means of gene transfer; or engineering T cells to express a chimeric antigen receptor specific for a tumor antigen. ACT therapies with TCR targeting a single TAA have limited efficacy, yet abundant autoimmune toxicity. As for CAR-T therapy, so far the most successfully targeted tumors are those derived from B cells due to their unique expression of the CD19 antigen (these CAR-T cells also eliminate patient's normal B cells, an unwanted but manageable toxicity). Still, a sizable fraction of patients fail in such therapy due to the escaping of epitope-loss variants. There has been little success for CAR-T therapy in solid tumors. Although CAR-T therapies targeting a single TAA or two TAAs simultaneously have been attempted, tumor escaping and on-target/off-tumor toxicity remain major problems. Thus, the CAR-T therapy for solid tumors is mainly limited by the ability to identify antigens (ideally multiple) that are specifically expressed on tumor cell surface, but not in normal cells. Neoantigens, which term is used interchangeably with "mutation-derived antigens," are ideal for this purpose; however, the vast majority of neoantigens in cancers are "private" events, i.e., events rarely shared in multiple patients. Thus, identifying such neoantigens and generating CARs against these antigens is not practical.

EBV-transformed B cells, often called lymphoblastoid cell lines (LCLs), are well-known for enhanced antigen presentation capacity and would present EBV latent antigens (viral antigens) that are also expressed in EBV-associated tumor cells. EBV-specific CTLs, generated in vitro by repetitive stimulation of autologous or donor-derived T cells with EBV-LCLs have been used in clinic to treat EBV-associated B cell lymphomas and were effective in about 50% of patients. This T cell preparation process typically takes 2-3 months, while the tumor is often aggressive and thus necessitates urgent treatment. Sometimes EBV-transformed B cells are additionally transduced to increase EBV latent antigens expression/presentation, including a truncated and signaling-dead form of LMP1. The use of the LMP1 mutant in that approach was based on the following rationale: LMP1, when expressed in lymphoma cells or other tumor cells, had been shown able to activate/enhance presentation of transduced model antigens, but restrict presentation of its own epitopes unless its signaling function is disabled. Contrary to this rationale, the present disclosure shows that it is because LMP1 signaling-induced massive cellular antigens dilute or mask LMP1-derived epitopes.

LMP1-expressing B cells have advantages over LCLs in the brevity of T cell production protocol. The production of cytotoxic T cells from LMP1-expressing B cells takes only about 11 days (including the time for preparation of LMP1-expressing B cells and subsequent generation of antigen-specific T cells), in sharp contrast to 2-3 months required by lymphoblastoid cell line (LCL)-based protocols.

In certain embodiments, the method can further comprise culturing the T cell with a B cell or vaccine (e.g., the B cell or vaccine as disclosed herein) under suitable conditions to allow proliferation of the T cell. The suitable conditions can include certain factors that promote or enhance the survival, proliferation, or differentiation of T cells. Exemplary factors include cytokines (e.g., IL-2, IL-1, IL-6, IL-12, or IL-18), anti-CD3 antibodies, anti-CD28 antibodies, phytohemagglutinin, calcium ionophores, inhibitors to cell death (e.g., FasL/Fas neutralizing antibodies), and cells that can facilitate T cell activation (e.g., macrophages or dendritic cells). In contrast to the traditional method of activating T cells using LCL, which generally takes 2-3 months, the method disclosed herein can take about 11 days for preparation of LMP1-B cells and subsequent generation of antigen-specific T cells. Accordingly, in certain embodiments, the T cell is cultured for a suitable length of time (e.g., about 3-5 days, 5-7 days, 3-7 days, or 7-14 days; equal to or less than 3, 5, 7, or 10 days; or, equal to or less than 1, 2, 3, or 4 weeks). The T cell can be co-cultured with the B cell during the entire length of time or a portion thereof. In certain embodiments, the B cell that is contacted with the T cell is replenished (e.g., every 2-3 days, 3-4 days, or 4-5 days). The factors can be added and withdrawn anytime in the course of the culture. For example, IL-2 may be added from day 3 onward.

In another embodiment, the present disclosure relates to vaccination strategy for treatment of cancer. LMP1-expressing autologous B cells/lymphoma cells are used as an "LMP1-cell vaccine," after irradiation, to activate/expand T cells in vivo to treat these lymphoma patients. Prior to the present disclosure, vaccination regimens mostly aimed at a single TAA have produced rare clinical benefit, partly due to the escaping of antigen/epitope-loss variants. Another known strategy to target multiple TAAs is to load dendritic cells (DCs) with tumor cell lysates. This strategy is currently under clinical testing, yet may encounter several obstacles. While the clinical efficacy of tumor neoantigen vaccination awaits further report, identification of tumor neoantigen is a laborious process, and the vast majority of these neoantigens are "private" events (rarely shared in multiple patients).

The vaccination strategies described herein utilize LMP1 signaling-induced cellular antigens expression, presentation, and co-stimulation to activate T cell immunity against a broad spectrum of TAAs and neoantigens in a simple and expeditious way. The target antigens of the vaccination strategy using LMP1-expressing primary B cells, as described herein, are LMP1 signaling-induced cellular antigens (including many TAAs) (FIG. 1A). By contrast, the vaccination strategy using LMP1-expressing lymphoma cells, as described herein, can generate anti-tumor T cells against lymphoma inherent TAAs and neoantigens (FIG. 1B). The use of LMP1-expressing primary and lymphoma cells for vaccination obviates the need to identify the specific antigens and pair them with particular MHCs (e.g., HLAs). Therefore, vaccination strategies described herein generates polyclonal cytotoxic T cells against lymphoma inherent TAAs and neoantigens. Such vaccination strategies are suitable for eliciting T cell responses to lymphoma inherent antigens, because LMP1 signaling would enhance cell endogenous antigen presentation and co-stimulation, i.e., turning the lymphoma cells into hyperimmunogenic APCs.

In another embodiment, LMP1 signaling in other lineages of cells (non-B cells) can be used to enhance cell endogenous antigen presentation and co-stimulation, and thus LMP1-expressing patient-derived tumor cells can be used to activate/expand T cells in both in vitro ACT strategies and in vivo vaccination strategies to treat the corresponding tumor patients. The target antigens of the ACT and vaccination strategies with LMP1-expressing tumor cells of non-B lineages, as described herein, include the tumor inherent TAAs and neoantigens.

In certain embodiments, the ACT and vaccination strategies described herein using LMP1-expressing B cells can be applied to non-EBV-associated cancers that share one or more TAAs with LMP1-expressing B cells. In some embodiments, the non-EBV-associated cancer may express one or more tumor-associated antigens (TAAs) that are also expressed by the LMP1-expressing B cells or LMP1-expressing non-B cells.

For both the ACT and vaccination strategies, the use of LMP1-expressing lymphoma cells may provide some advantages in that anti-tumor T cells against the lymphoma inherent TAAs and neoantigens can be generated, as LMP1 signaling would enhance cell endogenous antigen presentation and co-stimulation, i.e., turning the lymphoma cells into hyperimmunogenic APCs (see FIG. 1B). However, some lymphomas maybe suboptimal in co-stimulation function and may not be easily accessible, while autologous B cells (non-tumorous) would be intact in such function and easy to obtain from peripheral blood. Therefore, for lymphoma patients the choice of LMP1-expressing autologous B cells or LMP1-expressing lymphoma cells will be tailored to patient-specific conditions. For solid tumors, patient-derived cancer cells are easier to obtain and grow than normal cells of the same lineages and thus are preferred.

Both the ACT and vaccination strategies described herein fulfill several most desired features for effective cancer immunotherapy: (1) eliciting both cytotoxic CD4 and cytotoxic CD8 T cell responses; (2) targeting a large array of TAAs, and neoantigens when LMP1-expressing tumor cells are used; (3) being simple and fast. Of further note, efficient generation of cytotoxic anti-tumor CD4 cells represents a unique feature of the ACT and vaccination strategies described herein, considering that (i) recent work from us and others have shown great potential of cytotoxic CD4 cells in treating various cancers; (ii) these cells would be particularly important in fighting cancers that escape CD8 killing; (iii) a general approach for rapid generation of tumor antigen-specific cytotoxic CD4 cells was not available prior to the present invention.

In certain embodiments, cytotoxicity of T cells is examined using an in vitro killing assay. CD4$^+$ and CD8$^+$ T cells were isolated by Fluorescence-activated cell sorting (FACS) from CD19-cre; LMP1$^{flSTOP}$ mice on a CB6F1 background. The T cells were co-cultured with $4 \times 10^3$ target cells at various effector:target ratios for 4 hours in 96-well plates, followed by active Caspase-3 staining (BD) (He et al. J. Immunol. Methods 304: 43-59 (2005)). In all killing assays, effector-target mixtures in U-bottom 96-well plates were spun at 200 rpm for 2 min before moving to incubator, and cultures were stained with anti-CD19, anti-CD4, and anti-CD8 to identify target cells (B cells or lymphoma cells) and effector cells. Active Caspase-3 positive CD19⁺ cells represent apoptotic target cells. % specific killing=% apoptotic target cells of cultures with both effectors and targets–% apoptotic target cells of cultures with targets alone. As used herein, an effector of in vitro killing assay encompasses, but is not limited to, a cytotoxic CD4⁺ and/or CD8⁺ T cell, and a target of in vitro killing assay encompasses, but is not limited to, a LMP1-expressing B cell.

In certain embodiments, a B cell specific LMP1 transgene expression is enabled with CD19-cre. The CD19 promoter specifically directs Cre expression early in (starting at the pro-B stage) and continuing throughout B-lymphocyte development. A Cre cassette is inserted into the CD19 exon 2, functionally disrupting the gene. Homozygous mice are CD19-deficient, whereas heterozygous mice are phenotypically normal and can be used for specific deletion of floxed cassette from conditional alleles, leading to activation or inactivation of target genes, in B-lymphocytes. In another embodiment, a B cell encompasses a cell modified or derived from a B-lymphocyte. Yet another embodiment, a non-B cell encompasses, but is not limited to, a cell modified or derived from a solid tumor cell.

Detection of T cells specific to TAAs presented by LMP1-expressing B cells or non-B cells encompasses, but is not limited to, use of TAA-tetramers (or pentamers) in $C^{ERT2}L$ and CL mice as described infra. In some embodiment, tetramers (or pentamers) are made with H-2D$^b$, H-2K$^b$ and I-A$^b$. Predicted peptides loaded on B6 splenocytes or CpG-activated B cells (as antigen-presenting cells) are used to test T cells response by proliferation or cytokine assays. Confirmed tetramers are used to monitor the corresponding antigen-specific T cells in mice under therapeutic studies to characterize/optimize "LMP1-cell vaccine" and ACT approaches.

In some embodiments, LMP1-A20 lymphoma cell vaccine and LMP1-B cell vaccine are compared for their efficacies in treating A20 lymphoma-bearing mice using the method described below. Yet in another embodiment, vaccination efficacies with or without antibody-mediated pre-depletion of CD4⁺ and CD8⁺ T cells may be compared to demonstrate the contribution of CD4⁺ and CD8⁺ T cells in the tumor control. In some embodiments, vaccination efficacy can be tested with a poorly immunogenic tumor cell. Poorly immunogenic tumor cells encompass, but are not limited to, A20 lymphoma cells and B16 melanoma cells.

In another embodiment, the ACT or vaccination strategy described herein can be administered with an immune co-stimulation therapy and/or an immune checkpoint targeting therapy as a part of a combination therapy. An immune checkpoint targeting therapy encompasses, but is not limited to, anti-PD1 and/or -CTLA4.

In some embodiments, T cells can be expanded on LMP1-expressing cells under suitable conditions. When co-cultured with LMP1-expressing B cells in vitro, naïve T cells (CD4⁺ or CD8⁺) from wild-type mice become activated, differentiate into cytotoxic effectors and expand well (CD8⁺ T cell expansion can be enhanced by addition of IL-2 from day-3 onward). These expanded T cells can be used to treat lymphoma-bearing mice, after preconditioning the mice with irradiation.

In some embodiments, LMP1-expressing cells can be irradiated to abrogate their ability to proliferate. Any effective type of radiation may be used. According to other embodiments, any effective method to prevent proliferation of these cells may be used.

In yet another embodiment, both ACT and vaccination strategies described herein can be validated and optimized in preclinical cancer model. Preclinical cancer model encompasses, but is not limited to, lymphoma and melanoma models. In some embodiment, both ACT and vaccination strategies described herein can be validated and optimized in preclinical cancer model in combination with checkpoint blockade.

In some embodiment, human T cells can be primed with a LMP1-expressing autologous cell. The LMP1-expressing autologous cell encompasses, but is not limited to, a LMP1-expressing B cell, a LMP1-expressing lymphoma cell, and a LMP1-expressing melanoma cell.

LMP1 NCBI Gene ID No. is 3783750. Mouse CD40 NCBI Gene ID No. is 21939. Human CD40 NCBI Gene ID No. is 958.

In describing and claiming the instant application, the following terminology will be used in accordance with the definitions set forth below.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing," and "comprising" are interchangeable and one of skill in the art is cognizant that these terms are open ended terms.

As used herein, the term "antigen" is defined as a molecule that provokes an immune response. This immune response may involve either antibody production, or the activation of specific immunologically competent cells, or both. An antigen can be derived from organisms, subunits of proteins/antigens, killed or inactivated whole cells or lysates. Exemplary organisms include but not limited to Epstein-Barr virus (EBV) and cells infected by EBV. Any macromolecules, including virtually all proteins or peptides, can serve as antigens. Furthermore, antigens can be derived from recombinant or genomic DNA. In certain embodiments, an antigen includes a fragment of a protein that elicits an immune response.

As used herein, the term "LMP1" refers to Epstein-Barr virus (EBV) latent membrane protein 1. In a particular embodiment, LMP1 is a 100% identical to the previously known polypeptide sequences (GenBank Accession No. YP_401722). In another embodiment, LMP1 has the amino acid sequence of SEQ ID NO: 1. In further embodiment, LMP1 is a polypeptide with a sequence identity ranging from 70% to 80%, from 81% to 85%, from 86% to 90%, from 91% to 95%, from 96% to 100%, or 100% to SEQ ID NO. 1. In other embodiments, LMP1 is a polypeptide with a sequence identity of at least 75, 80, 85, 90, 95, 96, 97, 98 or 99% to SEQ ID NO. 1.

(LMP1 polypeptide sequence from GenBank Accession No. YP_401722)

```
                                   SEQ ID NO: 1
MEHDLERGPPGPRRPPRGPPLSSSLGLALLLLLLALLFWLYIVMSDWTGG

ALLVLYSFALMLIIIILIIFTFRRDLLCPLGALCILLLMITLLLIALWNL

HGQALFLGIVLFIFGCLLVLGIWIYLLEMLWRLGATIWQLLAFFLAFFLD

LILLIIALYLQQNWWTLLVDLLWLLLFLAILIWMYYHGQRHSDEHHHDDS
```

-continued

LPHPQQATDDSGHESDSNSNEGRHHLLVSGAGDGPPLCSQNLGAPGGGPD

NGPQDPDNTDDNGPQDPDNTDDNGPHDPLPQDPDNTDDNGPQDPDNTDDN

GPHDPLPHSPSDSAGNDGGPPQLTEEVENKGGDQGPPLMTDGGGGHSHDS

GHGGGDPHLPTLLLGSSGSGGDDDDPHGPVQLSYYD.

The term "LMP1 signaling-induced cellular antigen" herein refers to a cellular antigen whose expression is induced and/or enhanced by LMP1 signaling, and encompasses, but is not limited to, Tumor-Associated Antigens (TAAs), a group of non-mutated cellular antigens recognizable by T cells in certain tumors. Exemplary LMP1 signaling-induced cellular antigens include, but are not limited to, Cdkn1a/p21 (GenBank Accession No.: NP_001104569), Birc5/Survivin (GenBank Accession No.: NP_033819), Epha2 (GenBank Accession No.: NP_034269), and Kif20a (GenBank Accession No.: NP_001159878).

(Cdkn1a/p21 polypeptide sequence from GenBank
Accession No.: NP_001104569)
                                          SEQ ID NO: 2
MSNPGDVRPVPHRSKVCRCLFGPVDSEQLRRDCDALMAGCLQEARERWNF

DFVTETPLEGNFVWERVRSLGLPKVYLSPGSRSRDDLGGDKRPSTSSALL

QGPAPEDHVALSLSCTLVSERPEDSPGGPGTSQGRKRRQTSLTDFYHSKR

RLVFCKRKP (Birc5/Survivin polypeptide sequence from GenBank
Accession No.: NP_033819)
                                          SEQ ID NO: 3
MGAPALPQIWQLYLKNYRIATFKNWPFLEDCACTPERMAEAGFIHCPTEN

EPDLAQCFFCFKELEGWEPDDNPIEEHRKHSPGCAFLTVKKQMEELTVSE

FLKLDRQRAKNKIAKETNNKQKEFEETAKTTRQSIEQLAA (Epha2 polypeptide sequence from GenBank Accession
No.: NP_034269)
                                          SEQ ID NO: 4
MELRAVGFCLALLWGCALAAAAAQGKEVVLLDFAAMKGELGWLTHPYGKG

WDLMQNIMDDMPIYMYSVCNVVSGDQDNWLRTNWVYREEAERIFIELKFT

VRDCNSFPGGASSCKETFNLYYAESDVDYGTNFQKRQFTKIDTIAPDEIT

VSSDFEARNVKLNVEERMVGPLTRKGFYLAFQDIGACVALLSVRVYYKKC

PEMLQSLARFPETIAVAVSDTQPLATVAGTCVDHAVVPYGGEGPLMHCTV

DGEWLVPIGQCLCQEGYEKVEDACRACSPGFFKSEASESPCLECPEHTLP

STEGATSCQCEEGYFRAPEDPLSMSCTRPPSAPNYLTAIGMGAKVELRWT

APKDTGGRQDIVYSVTCEQCWPESGECGPCEASVRYSEPPHALTRTSVTV

SDLEPHMNYTFAVEARNGVSGLVTSRSFRTASVSTNQTEPPKVRLEDRST

TSLSVTWSIPVSQQSRVWKYEVTYRKKGDANSYNVRRTEGFSVTLDDLAP

DTTYLVQVQALTQEGQGAGSKVHEFQTLSTEGSANMAVIGGVAVGVVLLL

VLAGVGLFIHRRRRNLRARQSSEDVRFSKSEQLKPLKTYVDPHTYEDPNQ

AVLKFTTEIHPSCVARQKVIGAGEFGEVYKGTLKASSGKKEIPVAIKTLK

AGYTEKQRVDFLSEASIMGQFSHHNIIRLEGVVSKYKPMMIITEYMENGA

LDKFLREKDGEFSVLQLVGMLRGIASGMKYLANMNYVHRDLAARNILVNS

NLVCKVSDFGLSRVLEDDPEATYTTSGGKIPIRWTAPEAISYRKFTSASD

VWSYGIVMWEVMTYGERPYWELSNHEVMKAINDGFRLPTPMDCPSAIYQL

-continued

MMQCWQQERSRRPKFADIVSILDKLIRAPDSLKTLADFDPRVSIRLPSTS

GSEGVPFRTVSEWLESIKMQQYTEHFMVAGYTAIEKVVQMSNEDIKRIGV

RLPGHQKRIAYSLLGLKDQVNTVGIPI (Kif20a polypeptide sequence from GenBank
Accession No.: NP_001159878)
                                          SEQ ID NO: 5
MSHRILSPPAGLLSDEDVVDSPILESTAADLRSVVRKDLLSDCSVISASL

EDKQALLEDTSEKVKVYLRIRPFLTSELDRQEDQGCVCIENTETLVLQAP

KDSFALKSNERGVGQATHKFTFSQIFGPEVGQVAFFNLTMKEMVKDVLKG

QNWLIYTYGVTNSGKTYTIQGTSKDAGILPQSLALIFNSLQGQLHPTPDL

KPLLSNEVIWLDSKQIRQEEMKKLSLLIGGLQEEELSTSVKKRVHTESRI

GASNSFDSGVAGLSSTSQFTSSSQLDETSQLWAQPDTVPVSVPADIRFSV

WISFFEIYNELLYDLLEPPSHQHKRQTLRLCEDQNGNPYVKDLNWIHVRD

VEEAWKLLKVGRKNQSFASTHMNQQSSRSHSIFSIRILHLQGEGDIVPKI

SELSLCDLAGSERCKHQKSGERLKEAGNINTSLHTLGRCIAALRQNQQNR

SKQNLIPFRDSKLTRVFQGFFTGRGRSCMIVNVNPCASTYDETLHAAKFS

ALASQLVHAPPVHLGIPSLHSFIKKHSPQVGPGLEKEDKADSDLEDSPED

EADVSVYGKEELLQVVEAMKALLLKERQEKLQLETQLREETCNEMVEQMQ

QREQWCSERLDNQKELMEELYEEKLKTLKESLTTFYQEQIQERDEKIEEL

ETLLQEAKQQPAAQQSGGLSLLRRSQRLAASASTQQFQEVKAELEQCKTE

LSSTTAELHKYQQVLKPPPPAKPFTIDVDKKLEEGQKNIRLLRTELQKLG

QSLQSAERACCHSTGAGKLRQALTNCDDILIKQNQTLAELQNNMVLVKLD

LQKKAACIAEQYHTVLKLQGQASAKKRLGANQENQQPNHQPPGKKPFLRN

LLPRTPTCQSSTDSSPYARILRSRHSPLLKSPFGKKY

In some embodiments, T cells specific to TAAs presented by LMP1-expressing cells can be identified with TAA-tetramers in $C^{ERT2}L$ and CL mice on, but not limited to, CB6F1 background. In another embodiment, TAA loaded on B6 splenocytes or CpG-activated B cells can be used to test T cell response by proliferation and cytokine assays.

The term "LMP1-cell vaccine" described herein is defined as a cell, upon LMP1 expression, capable of processing and presenting LMP1 signaling-induced cellular antigens/TAAs, as well as individual tumor specific TAAs and neoantigens. LMP1-cell vaccine induces cytotoxic T cell responses against above described antigens.

The term "antigen-presenting cell" is any of a variety of cells capable of displaying, acquiring, and/or presenting at least one antigen or antigenic fragment on its cell surface. In general, an antigen-presenting cell (APC) can be any cell that induces and/or enhances an immune response against an antigen or antigenic composition. According to certain embodiments, a cell that displays or presents an antigen normally or preferentially with a class II major histocompatibility (MHC-II) molecule or complex to an immune cell is a professional APC. In some cases, the immune cell to which an APC displays or presents an antigen is a CD4+ or a CD8+ T cell. Full activation of naïve T cells can be achieved by an antigen displayed by an APC in the form of a peptide bound to an MHC, which provides specificity to the response, and a co-stimulatory signal, which is antigen nonspecific and facilitates the development of an effective immune response of adaptive immunity. T cell co-stimulation increases T cell proliferation, differentiation and survival. Activation of T cells without co-stimulation may lead to T cell anergy, T cell deletion or the development of immune tolerance. Additional molecules expressed by the APC or other immune cells that may aid or enhance an immune response include secreted molecules, such as cytokines and cytotoxic molecules.

The term "MHC" refers to "major histocompatibility antigen." In humans, the MHC genes are known as HLA ("human leukocyte antigen") genes. Although there is no consistently followed convention, some literature uses HLA to refer to HLA protein molecules, and MHC to refer to the genes encoding the HLA proteins. As such, the terms "MHC" and "HLA" are used interchangeably herein. The HLA system in humans has its equivalent in the mouse, i.e., the H2 system. The most studied HLA genes are the nine so-called classical MHC genes: HLA-A, HLA-B, HLA-C, HLA-DPA1, HLA-DPB1, HLA-DQA1, HLA-DQB1, HLA-DRA, and HLA-DRB1. In humans, the MHCs include at least three regions: Class I, II, and III. The A, B, and C genes belong to MHC class I, whereas the six D genes belong to class II. MHC class I molecules are made of a single polymorphic chain containing 3 domains (alpha 1, 2 and 3), which associates with beta 2 microglobulin at cell surface. Class II molecules are made of 2 polymorphic chains, each containing 2 domains (alpha 1 and 2, and beta 1 and 2). Class I MHC molecules are expressed on virtually all nucleated cells. Peptide fragments presented in the context of class I MHC molecules are recognized by CD8$^+$ T lymphocytes (traditionally called cytotoxic T lymphocytes or CTLs). CD8$^+$ T lymphocytes frequently mature into cytotoxic effectors which can lyse cells bearing the stimulating antigen. Class II MHC molecules are expressed primarily on activated lymphocytes and professional APCs. CD4$^+$ T lymphocytes (traditionally called helper T lymphocytes or HTLs) are activated with recognition of a unique peptide fragment presented by a class II MHC molecule, usually found on an APC, like a macrophage, dendritic cell or B cell. CD4$^+$ T lymphocytes proliferate and secrete cytokines that either support an antibody-mediated response through the production of IL-4 or support a cell-mediated response through the production of IL-2 and IFN-gamma, or acquire direct killing activity (cytotoxicity).

The term "immune co-stimulatory molecule" refers to molecules on APCs or T cells that provide a non-antigen-specific signal for T cell proliferation and functional differentiation. Representative immune co-stimulatory molecules include, but are not limited to, CD80/B7-1, CD86/B7-2, CD70, CD27, OX40 ligand, OX40, 4-1BB ligand, 4-1BB, and GITR. Accordingly, "immune co-stimulation therapies" include without limitation agonistic antibodies that specifically bind an immune co-stimulatory molecule.

As used herein, the term "cytokine" is defined as growth, differentiation or chemotropic factors secreted by immune or other cells, whose action is on cells of the immune system, such as, but not limited to, T cells, B cells, NK cells and macrophages or other cell types, such as endothelial cells, hematopoietic cells, etc. Representative cytokines include, but are not limited to, the group consisting of IFN-γ, TNF-α, IL-2 and IL-17.

The term "sequence identity" or "sequence homology" of two sequences when used herein relates to the number of positions with identical nucleotides or amino acids divided by the number of nucleotides or amino acids in the shorter of the sequences, when the two sequences are aligned. In particular embodiments, the sequence identity is from 70% to 80%, from 81% to 85%, from 86% to 90%, from 91% to 95%, from 96% to 100%, or 100%. In certain embodiments, the sequence identity is at least 80, 81, 82, 83, 84, 85, 86, 87, 88, 89, 90, 91, 92, 93, 94, 95, 96, 97, 98, or 99%.

The term "cancer" as used herein is defined as a hyper-proliferation of cells whose unique trait—loss of normal controls—results in unregulated growth, lack of differentiation, local tissue invasion, and metastasis. Examples include, but are not limited to, melanoma, hepatocarcinoma, leukemia, lymphoma, retinoblastoma, astrocytoma, glioblastoma, neuroblastoma, sarcoma, lung, breast, uterine, pancreatic, prostate, renal, bone, testicular, uterine, ovarian, cervical, gastrointestinal, brain, colon, or bladder cancer.

In the context of cancer treatment, immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target (e.g. a LMP1 signaling-induced cellular antigen, a lymphoma inherent TAA, or a tumor neoantigen). Various effector cells include CD8$^+$ T cells, CD4$^+$ T cells and NK cells. In one aspect of immunotherapy for treatment of cancer is ACT as described herein. In another aspect of immunotherapy for treatment of cancer is vaccination strategy as described herein.

As used herein, the term "cytotoxic T cell (CTL)" refers to T lymphocytes that can kill cells expressing a MHC-presented antigen such as cells infected by viruses or transformed cancer cells. Herein the cytotoxic T cells include CD8$^+$ T cells (the traditionally referred CTLs or CD8$^+$ CTLs) and a subtype of CD4$^+$ T cells (CD4$^+$ CTLs) that have direct killing activity as described in the instant disclosure. CTLs have specificity for peptide antigens that are presented in association with proteins encoded by the MHC genes and which are expressed on the surfaces of cells. CTLs lyse cells infected with microbes (e.g., such as viruses), inducing and promoting the destruction of intracellular microbes. In certain embodiments, CTLs lyse cancer cells.

In some embodiments, T cells can be expanded on LMP1-expressing cells under suitable conditions. The term "suitable conditions" as used herein comprises co-culturing of T cells with LMP1-expressing cells, which may be replenished every 4-5 days. IL-2 may be added from day 3 onward.

The terms "cell," "cell line," and "cell culture" as used herein include progeny, which are any and all subsequent generations. It is understood that all progeny may not be identical due to deliberate or inadvertent mutations.

The term "B cell" refers to a type of lymphocyte, developed in bone marrow, that circulates in the blood and lymph. Upon encountering a particular foreign antigen, B cells differentiate into a clone of plasma cells that secrete a specific antibody and a clone of memory cells that differentiate into plasma cells making the antibody upon re-encountering the antigen.

The term "naïve B cell" refers to a B cell that has not been exposed to a foreign antigen so that it has not committed differentiation into a clone of memory or plasma cells.

The term "neoplastic B cell" refers to a B cell that undergoes an abnormal pattern of growth.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

As used herein, the term "expression vector" refers to an exogenous vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide. The expression vector, as used herein, lacks at least 50%, 55%, 60%, 65%, 70%, 75%, 80%, 85%, 90%, 91%, 92%, 93%, 94%, 95%, 96%, 97%, 98%, 99% or 100% of an EBV genome, thereby incapable of replicating EBV viral genome.

The term "host cell" means any cell type that is susceptible to transformation, transfection, transduction, or the like with a nucleic acid construct or expression vector comprising a polynucleotide. The term "host cell" encompasses any progeny of a parent cell that may not be identical to the parent cell due to mutations that occur during replication.

As used herein, the term "viral vector" encompasses vector DNA/RNA as well as viral particles generated thereof. Viral vectors can be replication-competent, or can be genetically disabled so as to be replication-defective or replication-impaired. The term "viral particle" refers to the viral genome as well as a protein coat around the viral genome, referred to herein as the "capsid". In certain embodiments, the viral particle also includes an envelope of lipids that surrounds the protein coat. The viral genome comprises the nucleotide sequence that is located between the LTRs in the expression vector used for the production of the viral vector particles. A variety of viral vectors, such as an adenoviral vector, an adeno-associated viral vector, a lentiviral vector, and a retroviral vector, known in the art can be modified to express or carry a nucleotide sequence.

Non-viral vectors include, but are not limited to liposomes and lipoplexes, polymers and peptides, synthetic particles and the like. In certain aspects a liposome or lipoplex has a neutral, negative or positive charge and can comprise cardiolipin, anisamide-conjugated polyethylene glycol, dioleoyl phosphatidylcholine, or a variety of other neutral, anionic, or cationic lipids or lipid conjugates. A vector can be complexed to cationic polymers (e.g., polyethylenimine (PEI)), biodegradable cationic polysaccharide (e.g., chitosan), or cationic polypeptides (e.g., atelocollagen, poly lysine, and protamine).

The term "transfection" or "transduction" as used herein refers to a process by which exogenous nucleic acid is transferred or introduced into the host cell. A "transfected" or "transduced" cell is one which has been transfected or transduced with exogenous nucleic acid. The cell includes the primary subject cell and its progeny.

The term "plurality" refers to two or more of anything, such as cells or antigens. For the purposes of the present application, the terms "a", "an" or "the" refers to one or more of anything, such as a cell or the cell or an antigen or the antigen. For the purpose of the present application, a plurality of anything may be homogenous or heterogeneous. For the purposes of the present application, the term "homogenous" refers to a plurality of identical anything, such as cells or antigens. For the purposes of the present application, the term "heterogeneous" refers to a plurality of anything in which there are least two different types of anything, such as cells or antigens.

The term "exogenous" as used herein with reference to nucleic acid and a particular cell refers to any nucleic acid that does not originate from that particular cell as found in nature. Thus, a non-naturally-occurring nucleic acid is considered to be exogenous to a cell once introduced into the cell. Nucleic acid that is naturally occurring also can be exogenous to a particular cell. For example, an entire chromosome isolated from a cell of subject X is an exogenous nucleic acid with respect to a cell of subject Y once that chromosome is introduced into Y's cell.

The term "nucleic acid" or "polynucleotide" refers to deoxyribonucleic acids or ribonucleic acids and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994))

The term "promoter" refers to a nucleic acid sequence, usually found upstream (5') to a coding sequence, which directs transcription of a nucleic acid sequence into mRNA. The promoter or promoter region typically provide a recognition site for RNA polymerase and the other factors necessary for proper initiation of transcription. As contemplated herein, a promoter or promoter region includes variations of promoters derived by inserting or deleting regulatory regions, subjecting the promoter to random or site-directed mutagenesis, etc. The activity or strength of a promoter may be measured in terms of the amounts of RNA it produces, or the amount of protein accumulation in a cell or tissue, relative to a promoter whose transcriptional activity has been previously assessed.

The term "expression cassette" relates particularly to a nucleic acid molecule and a region of a nucleic acid molecule, respectively, containing a regulatory element or promoter being positioned in front of the coding region, a coding region and an open reading frame, respectively, as well as a transcriptional termination element lying behind the coding region. The regulatory element and the promoter, respectively, residing in front of the coding region, can be a constitutive, i.e., a promoter permanently activating the transcription (e.g. MSCV promoter), or a regulatable promoter, i.e. a promoter which can be switched on and/or off. The coding region of the expression cassette can be a continuous open reading frame as in the case of a cDNA having a start codon at the 5' end and a stop codon at the 3' end. The coding region can consist of a genomic or a newly combined arrangement of coding exons and interspersed non-coding introns. However, the coding region of the expression cassette can consist of several open reading frames, separated by so called IRES (Internal Ribosome Entry Sites). In particular, as used herein, the expression cassette comprises a nucleic acid sequence encoding a polypeptide with sequence identity ranging from 70% to 80%, from 81% to 85%, from 86% to 90%, from 91% to 95%, from 96% to 100%, or 100% to SEQ ID NO. 1.

The phrase "operably linked" refers to the functional spatial arrangement of two or more nucleic acid regions or nucleic acid sequences. For example, a promoter region may be positioned relative to a nucleic acid sequence such that transcription of the nucleic acid sequence is directed by the promoter region. Thus, the promoter region is "operably linked" to the nucleic acid sequence.

As used herein, the term "autologous" is meant to refer to any material derived from the same subject to whom it is later to be re-introduced into the subject.

As used herein, the term "polypeptide" is defined as a chain of amino acid residues, usually having a defined sequence. As used herein the term polypeptide is interchangeable with the terms "peptides" and "proteins."

As used herein, the term "treating" includes prophylaxis of the specific disorder or condition, or alleviation of one or more symptoms associated with a specific disorder or condition and/or preventing or eliminating the symptoms. As used herein an "effective" amount or a "therapeutically effective amount" of a pharmaceutical refers to a nontoxic but sufficient amount of the pharmaceutical to provide the desired effect. For example one desired effect would be the prevention or treatment of breast cancer. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

As used herein, the term "in vivo" refers to a process taking place inside a living subject. The term "in vitro" refers to a process taking place outside a living subject.

The term "proliferative capacity" refers to the ability of cells to undergo cell division. The proliferative capacity of cells may be measured by any method known in the art including, but not limited to, the enumeration of cells before and after stimulation with a suitable growth factor, fluorescent dye assays, incorporation of BrdU in the DNA of proliferating cells, incorporation of radio-labeled analogues such as 3H-thymidine into the DNA of proliferating cells and/or the detection of cellular markers of proliferation.

"A subject" encompasses, but is not limited to, a mammal, e.g. a human, a domestic animal or a livestock including a cat, a dog, a cattle and a horse. As used herein the term "patient" without further designation is intended to encompass any warm blooded vertebrate domesticated animal (including for example, but not limited to livestock, horses, cats, dogs and other pets) and humans.

"Surgical resection" encompasses, but is not limited to, a surgical procedure to remove an abnormal tissue, wherein a normal surrounding tissue may be removed at the same time. An abnormal tissue includes but is not limited to a tumor.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the treatment combination in treating the conditions or disorders described herein.

The term "solid tumor" refers to an abnormal mass of tissue. In certain embodiments, the mass of tissue does not contain cysts or liquid areas. Solid tumors may be benign or malignant. Examples of solid tumors are sarcomas, carcinomas. Leukemias and lymphomas generally do not form solid tumors. In certain embodiments, melanoma, gastric cancer, and nasopharyngeal carcinoma form solid tumors.

It is understood by those of ordinary skill in the art, that the term "immune checkpoints" means a group of molecules on the cell surface of CD4 and CD8 T cells or other cells, such as tumor cells or other immunoregulatory cells. These molecules effectively serve as "brakes" to down-modulate or inhibit an anti-tumor immune response. Immune checkpoint molecules include, but are not limited to, Programmed Death 1 (PD-1), Cytotoxic T-Lymphocyte Antigen 4 (CTLA-4), B7-H1 (also known as PDL1), and LAG3, which directly inhibit immune cells. Immunotherapeutic agents which can act as immune checkpoint inhibitors useful in the methods of the present application, include, but are not limited to, anti-PD1, anti-B7-H1, anti-CTLA-4 (ipilimumab) and anti-LAG3.

Furthermore, in accordance with the present disclosure there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, New York (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R.I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

The following examples are provided to further elucidate the advantages and features of the present application, but are not intended to limit the scope of the application. The examples are for illustrative purposes only.

EXAMPLES

Materials and Methods

Mice

C57BL/6J (B6), CD19-cre, CIITA$^{-/-}$, CD40$^{-/-}$, Foxp3$^{DTR/GFP}$ and YFP$^{flSTOP}$ (all on a B6 background) were obtained from the Jackson Laboratory. Rag2$^{-/-}$ common γchain$^{-/-}$ (Rag2$^{-/-}$γc$^{-/-}$) mice were bred in our mouse colony or purchased from Taconic. LMP1$^{flSTOP}$ allele on a BALB/c background has been described previously (B. Zhang et al., Immune surveillance and therapy of lymphomas driven by Epstein-Barr virus protein LMP1 in a mouse model. Cell 148, 739 (Feb. 17, 2012)). Foxp3$^{DTR/GFP}$;

CD19-cre; LMP1$^{flSTOP}$ (Foxp3$^{DTR/GFP}$; CL) mice on a (C57BL/6×BALB/c) F1 (CB6F1) background were generated by crossing CD19-cre; Foxp3$^{DTR/GFP}$ to LMP1$^{flSTOP}$ mice. Only male Foxp3$^{DTR/GFP}$; CL mice were used in experiments. CD40$^{+/-}$; CD19-cre mice were crossed with CD40$^{+/-}$; LMP1$^{flSTOP}$ mice to generate CD40$^{-/-}$; CL mice and their corresponding controls. All mice were bred and maintained in animal facilities under specific pathogen-free conditions. All animal experiments were conducted according to protocols approved by the DFCI Institutional Animal Care and Use Committee.

Flow Cytometry

Lymphoid single-cell suspensions were stained with the following monoclonal antibodies specific for CD3c (145-2C11), CD4 (L3T4), CD8 (53-6.7), CD19 (1D3), CD25 (PC61.5), CD40 (3/23), CD43 (S7), CD69 (H1.2F3), CD70 (FR70), CD80 (16-10A1), CD86 (GL1), 4-1BBL (TKS-1), OX40L (RM134L), Fas (Jo2), H-2Kb (AF6-88.5), I-Ab (AF6-120.1), ICAM-1 (3E2), TCRb (H57-597), TCR Vb5 (MR9-4), TCR Vb11 (RR3-15), TCR Vb12 (MR11-1), TFN-g (XMG1.2), Granzyme B (GzmB, NGZB), Perforin (eBioOMAK-D), CD107a (1D4B), FasL (MFL3), TRAIL (N2B2), Foxp3 (FJK-16s), Eomes (Dan11mag), T-bet (4B10), GATA-3 (TWAJ) and RORgt (Q31-378) from BD Biosciences, Biolegend or eBioscience. Topro3 (Invitrogen) or eFluor 506 (eBioscience) was used to exclude dead cells. Intracellular staining for GzmB, perforin, Foxp3, Eomes, T-bet, GATA-3 and RORgt was done with the Foxp3 staining buffer set (eBioscience). Intracellular staining for GzmB and IFN-g was conducted using the IC Fixation/Permeabilization buffer (eBioscience). TCR VP repertoire was analyzed with the mouse Vβ TCR screening panel (BD Biosciences) according to the manufacturer's instructions. All samples were acquired on a FACSCanto II (BD Biosciences), and analyzed by FlowJo software (Tree Star). Fluorescence-activated cell sorting (FACS sorting) was performed using a FACSAria II (BD Biosciences). In all T cell sorting experiments, CD1d tetramer (NIH tetramer facility) was employed to exclude natural killer T cells.

Retroviral Constructs and Transduction

LMP1 cDNA was cloned into the MSCV-IRES-GFP or MSCV-Puro retroviral vector to generate MSCV-LMP1-IRES-GFP or MSCV-LMP1-Puro. To generate a retrovirus expressing the signaling-defective LMP1 mutant LMP1l m, amino acids FWLY(38-41) of the transmembrane domain 1 (TM1) of LMP1 were altered to AALA by QuikChange site-directed mutagenesis (Stratagene), and the resultant mutant was cloned into the MSCV-IRES-GFP or MSCV-Puro retroviral vector. CD43-depleted (by using anti-CD43 microbeads from Miltenyi Biotec) splenic B cells were activated in vitro by 20 μg/ml lipopolysaccharide (LPS, Sigma) for 24 hrs, infected with retroviruses, and continually cultured in the presence of LPS. For B cells transduced with GFP-carrying retroviruses, at 48 or 72 hrs post-infection the cells were extensively washed and then used in downstream experiments (GFP$^+$ indicates successfully transduced cells). For B cells transduced with Puro-carrying retroviruses, at 24 hrs post-infection the cells were selected with Puromycin (6 μg/ml; Sigma) for 18 hrs, followed by extensive wash and recovery in fresh medium for 1 day before using in downstream experiments.

In Vitro Killing Assay

Various target cells were labeled with CellTrace Violet (Invitrogen) before use. CD4 or CD8 T cells were purified from the bone marrow (BM) or spleen of mice by FACS sorting. The T cells were then co-cultured with 2×10$^3$ target cells at different effector:target ratios for 4 hrs (on LMP1- expressing B cells/lymphoma cells and corresponding control cells) or 6 hrs (on CD40-activated B cells and resting B cells) in 96-well round-bottomed plates, followed by active Caspase-3 staining (BD Biosciences) (B. Zhang et at, Immune surveillance and therapy of lymphomas driven by Epstein-Barr virus protein LMP1 in a mouse model. Cell 148, 739 (Feb. 17, 2012); L. He et al., A sensitive flow cytometry-based cytotoxic T-lymphocyte assay through detection of cleaved caspase 3 in target cells. Journal of immunological methods 304, 43 (September 2005)). For blocking assay, the target cells were pre-incubated with anti-IA/IE (M5/114.15.2) blocking antibody or isotype control rat IgG2b (both at 10 μg/ml; Biolegend) for 20 min at 37° C., whereas the CD4 T cells were pre-incubated with Fas-ligand neutralizing fusion protein rmFas-Fc or isotype control human IgG1 (both at 10 μg/ml; R&D Systems) under the same conditions. In all killing assays, effector-target mixtures in 96-well plates were spun down at 200 rpm for 2 min prior to the incubation at 37° C., and cultures were stained for CD4 or CD8 to exclude effector cells and analyzed for active Caspase-3 levels in CellTrace-labeled target cells. Active Caspase-3$^+$CellTrace$^+$ cells represent apoptotic target cells. % specific killing=% apoptotic target cells of cultures with both effectors and targets–% apoptotic target cells of cultures with targets alone.

T Cell Proliferation Assay for MHC Restriction

CD43-depleted splenic B cells were isolated from wild-type (WT) or CIITA$^{-/-}$ mice (both on a C57BL6 background) and activated by anti-CD40 antibody (HM40-3, eBioscience) at 1 μg/ml for 48 hrs. CD4 effector T cells (excluding GFP$^+$ regulatory T cells (Tregs)) from the BM of adult Foxp3$^{DTR/GFP}$; CL mice or CD4 T cells primed in vitro by LMP1-expressing B cells were sorted and stained with CellTrace (Invitrogen), followed by a 6 hrs incubation in fresh RPMI media to ensure the T cells were at rest before co-culture with target cells. The CD4 T cells (1×10$^5$ cells) were subsequently co-cultured with target cells, CD40-activated WT or CIITA$^{-/-}$ B cells (1×10$^5$ cells), in 96-well U-bottom plate for 4 days, followed by staining with Topro3, anti-TCRβ, -CD4 and -CD19 and FACS analysis of CellTrace dilution in CD4 cells.

LMP1 Localization Analysis

LMP1 or LMP1$^{TM1m}$ cDNA was each subcloned into the pCAG-GFP vector (Addgene, #11150) to obtain C-terminally GFP-tagged constructs. The plasmids (pCAG-LMP1-GFP, pCAG-LMP1$^{TM1m}$-GFP or vector control pCAG-GFP) were then electroporated into mouse lymphoma B cells (line 775) (B. Zhang et al., An oncogenic role for alternative NF-kappaB signaling in DLBCL revealed upon deregulated BCL6 expression. Cell reports 11, 715 (May 5, 2015)). 24 hrs after electroporation, the cells were counterstained with the DNA-specific fluorescent dye Hoechst 33342 (blue, Sigma) and imaged with fluorescence microscopy.

Gene Expression Profiling

B cells were isolated from spleens of YFP$^{flSTOP/+}$ and LMP$^{flSTOP}$/YFP$^{flSTOP}$ mice by CD43 depletion using magnetic-activated cell sorting (Miltenyi Biotec) and treated with TAT-Cre as previously described (S. B. Koralov et al., Dicer ablation affects antibody diversity and cell survival in the B lymphocyte lineage. Cell 132, 860 (Mar. 7, 2008)). At day 2 post-treatment, total RNA was extracted from the cells with TRIzol reagent (Invitrogen) according to manufacturer's specifications, followed by microarray analysis at the Molecular Biology Core Facility at DFCI, using GeneChip Mouse Gene 2.0 ST arrays (Affymetrix).

In Vitro Generation of Cytotoxic CD4 T Cells on LMP1-Expressing B Cells

Sorted CD4 T cells from the spleens of naïve B6 mice were plated in 12-well plates at $1.5 \times 10^6$ per well with irradiated (500 Rad) LMP1$^+$ or LMP1$^{TM1m+}$ B cells at a 1:1 ratio. Five days later, the CD4 T cells were re-stimulated with $0.75 \times 10^6$ of the same target B cells for an additional 2 days. All cells were cultured in RPMI 1640 medium (Gibco) supplemented with 10% fetal bovine serum (Sigma), 100 IU/ml penicillin (Gibco), 10 mM HEPES (Corning), 1× nonessential amino acids (Corning), 1 mM sodium pyruvate (Gibco) and 50 μM β-mercaptoethanol (Sigma), and without addition of any growth factors or cytokines.

Blockade of Co-Stimulatory Ligands During LMP1$^+$ B Cell-Driven Cytotoxic T Cell Production Irradiated LMP1-expressing B cells were pre-incubated with blocking antibodies against CD70 (FR70, rat IgG2b), OX40L (RM134L, rat IgG2b) and/or 4-1BBL (TKS-1, rat IgG2a), or the corresponding isotype controls (all at 10 μg/ml; Biolegend), for 50 min at 37° C. Splenic CD4 ($1 \times 10^6$) or CD8 cells ($0.5 \times 10^6$) sorted from naïve B6 mice were subsequently co-cultured with the target B cells at 1:1 ratio in 24-well plates. The CD8 T cells were harvested for FACS analysis after 3 days of co-culture, whereas the CD4 T cells were re-stimulated at day 5 with $0.5 \times 10^6$ of the same target B cells for an additional 2 days, followed by FACS analysis.

Statistical Analysis

Statistical significance was determined by unpaired two-tailed Student's t test, except where indicated; a p value<0.05 was considered significant (ns, not significant; *P<0.05, P<0.01, *P<0.001, and ****P<0.0001).

Figures 2A, 2B:
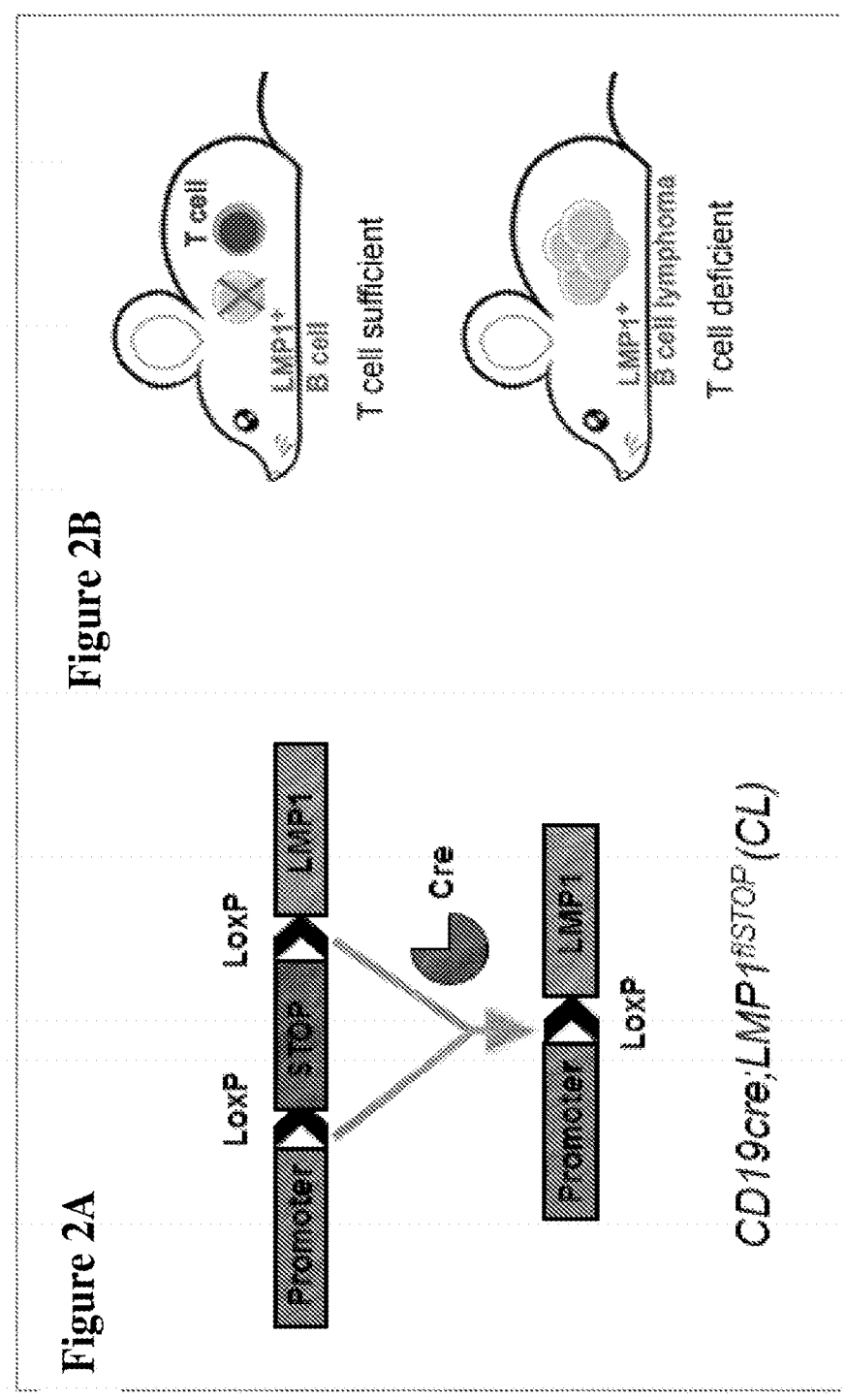
FIG. 2A is a schematic diagram showing an expression cassette of LMP1 used in generating CD19-cre; LMP1$^{flSTOP}$ (CL) transgenic mice.
FIG. 2B is a schematic diagram demonstrating the role of LMP1 in the surveillance and transformation of LMP1-expressing (EBV-infected) B cells.

Example 1. Generation and Characterization of a B Cell Specific LMP1 Transgenic Mouse Model LMP1 coding sequence derived from the EBV B95-8 strain, preceded by a loxP-flanked Neo$^r$-STOP cassette, was placed into Rosa26 locus to generate a conditional LMP1 knockin allele, LMP1$^{flSTOP}$, which allows expression of LMP1 through excision of a transcriptional/translational STOP cassette via Cre/loxP-mediated recombination (FIG. 2A). The LMP1$^{flSTOP}$ strain was generated from BALB/c-derived embryonic stem (ES) cells. Splenic B cells isolated from LMP1$^{flSTOP}$ mice expressed LMP1 following treatment with TAT-Cre and proliferated in cell culture, whereas TAT-Cre treated wild-type B cells died over time. The induction of LMP1 was accompanied by the upregulation of CD95/Fas. Subsequently, Fas was used as a reporter for LMP1 expression in B cells.

To generate B cell specific LMP1 transgenic mouse model, the LMP1$^{flSTOP}$ (BALB/c) strain was bred with CD19-cre (C57BL/6) strain. Homozygous CD19-cre mice were crossed with homozygous or heterozygous LMP1$^{flSTOP}$ or BALB/c mice to produce CD19-cre; LMP1$^{flSTOP}$ mice (hereafter referred as "CL") or CD19-cre/+ control mice (hereafter referred to as "C"), all on a CB6F1 background (F1 offspring of a cross between C57BL/6× BALB/c). CL mice expressed LMP1 transgene specifically in B cells. Analysis of CL mice revealed that LMP1-expressing B cells were eliminated by T cells, similar to EBV-infected B cells in humans; T cell depletion resulted in rapid, fatal B cell proliferation and lymphomagenesis in the mice, resembling EBV-driven malignancies in immunosuppressed patients (FIG. 2B). These experiments indicate a central role for LMP1 in the surveillance and transformation of EBV-infected B cells in vivo.

Figures 3A, 3B:
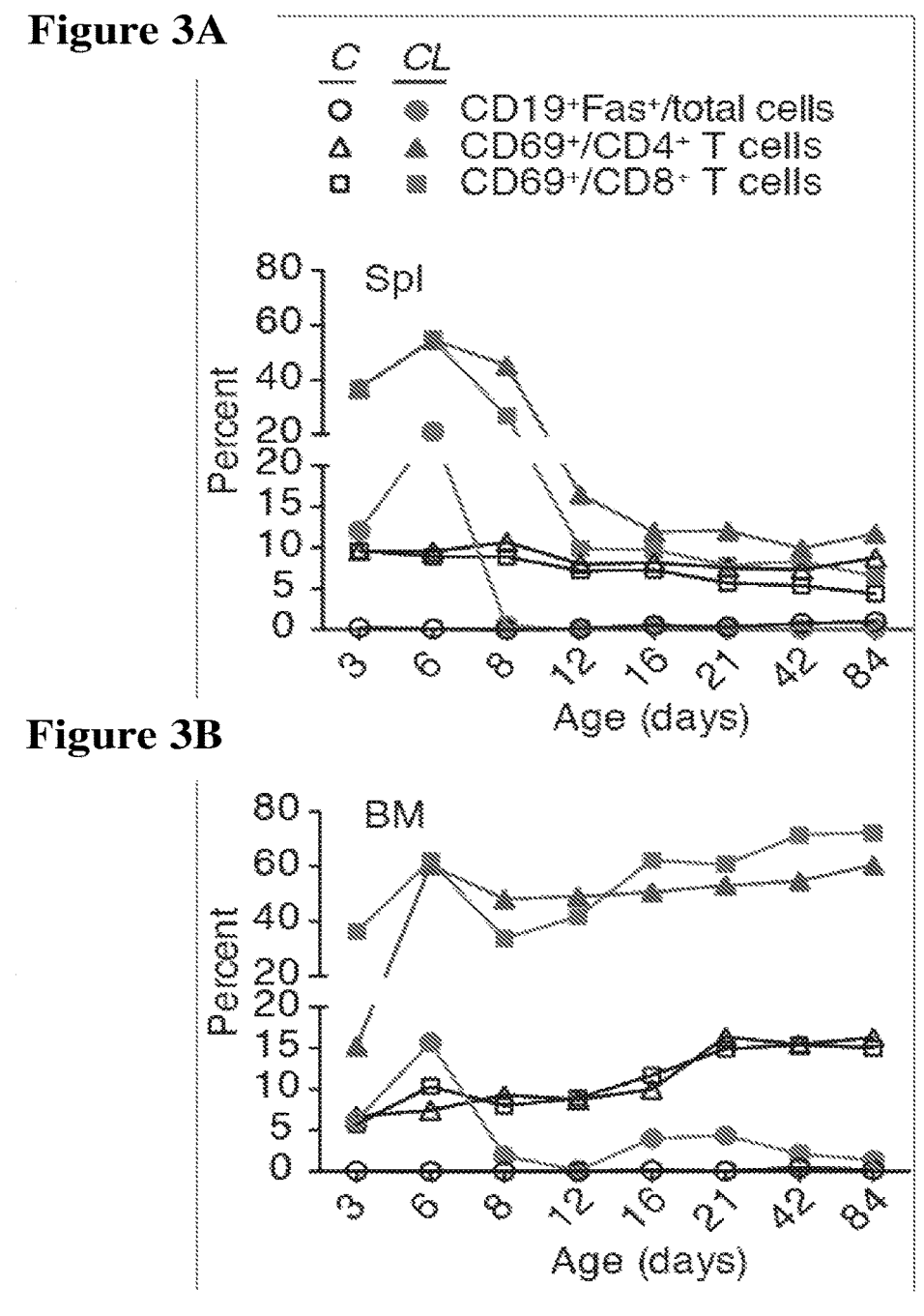
FIG. 3A is a graph showing dynamics of LMP1-expressing B cells (CD19$^+$Fas$^+$; Fas is induced by LMP1 signaling and consequently used as a reporter for LMP1 expression in B cells) and activated (CD69$^+$) CD4 and CD8 T cells, analyzed by FACS, in the spleen of CL mice compared to those in CD19-cre/+ control ('C') mice. The respective mean values of at least three mice of each genotype, at each time point are plotted.
FIG. 3B is a graph showing dynamics of LMP1-expressing B cells and activated (CD69+) CD4 and CD8 T cells, analyzed by FACS, in the bone marrow (BM) of CL mice compared to those in CD19-cre/+ control ('C') mice. The respective mean values of at least three mice of each genotype, at each time point are plotted.

Example 2. Both CD4 and CD8 T Cells Develop Cytotoxic Response to LMP1-Expressing B Cells The detailed time course and nature of immune surveillance in CL mice were investigated. Analysis of the dynamics of LMP1-expressing B cell and T cell responses revealed a peak T cell response against LMP1-expressing B cells on days 6-8 after birth, followed by rapid elimination of LMP1-expressing B cells (FIGS. 3A and 3B). T cells contracted afterwards, but long-term memory formed and persisted, and continued to eliminate newly arising LMP1-expressing B cells in the bone marrow (BM, the primary organ for B cell development). Accordingly, a small population of LMP1-expressing B cells was detected in the BM, but not in the spleen, of adult mice (FIGS. 3A and 3B).

Figure 4:
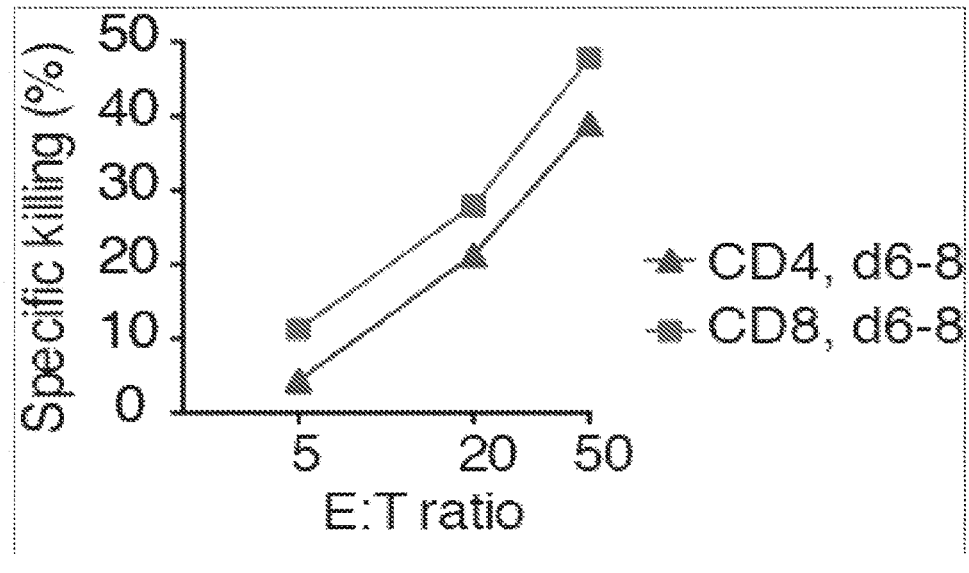
FIG. 4 is a graph showing cytolytic activity of CD4$^+$ and CD8$^+$ T cells to LMP1-expressing B cells. CD4 and CD8 T cells from day 6-8 CL mice kill LMP1-expressing lymphoma cells, upon co-culture for 4 hours. E:T ratio, effector to target cell ratios.
Figures 5A, 5B:
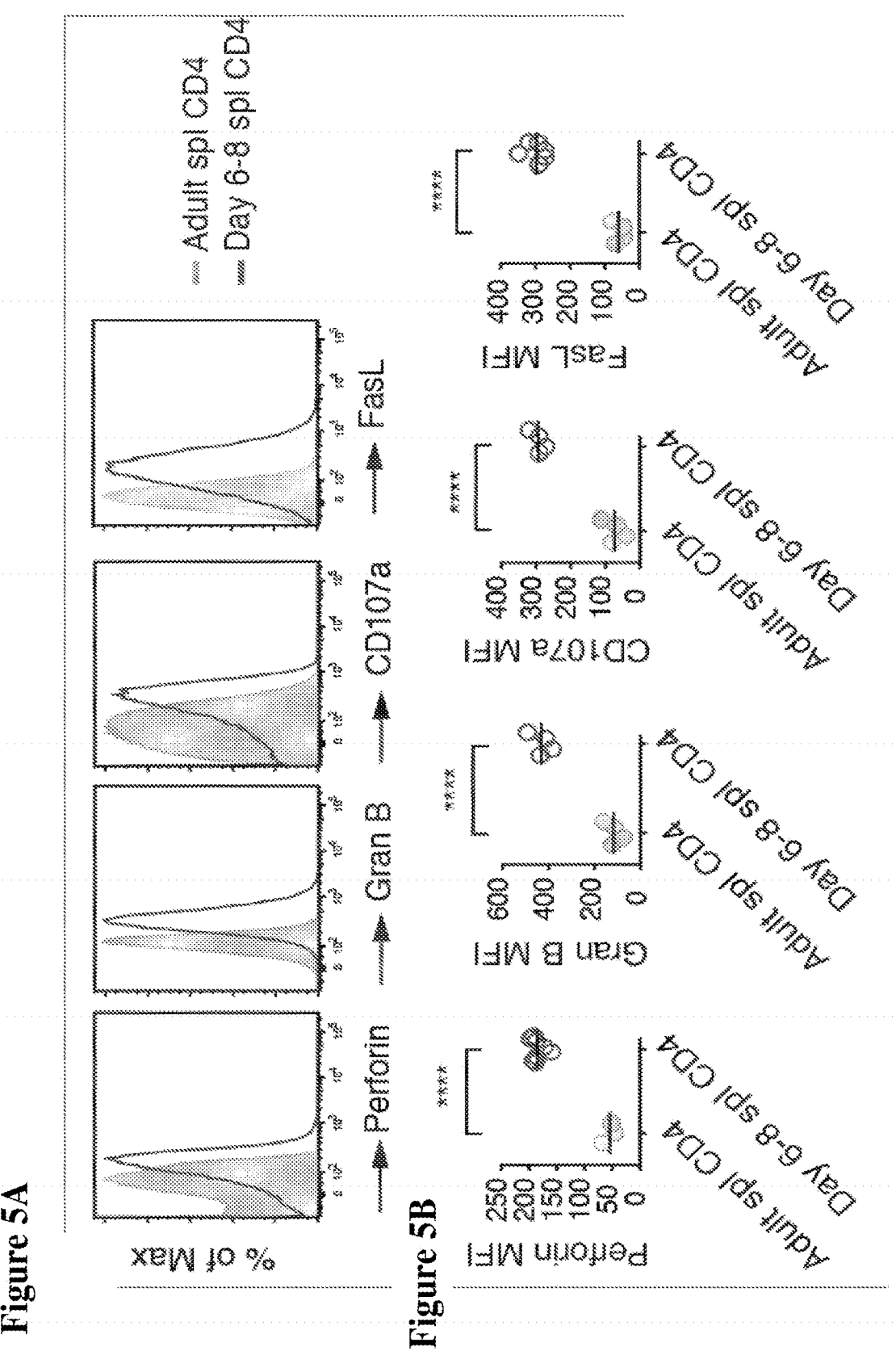
FIG. 5A shows FACS analysis of the indicated effector molecules in primary CD4 T cells isolated from day 6-8 CL mice spleen, compared to primary CD4 T cells from adult CL spleen, demonstrating tumor-killing T cells express key cytotoxic molecules.
FIG. 5B shows mean fluorescence intensities (MFI) of the indicated effector molecules detected as in the FIG. 5A FACS analysis.
Figures 5C, 5D:
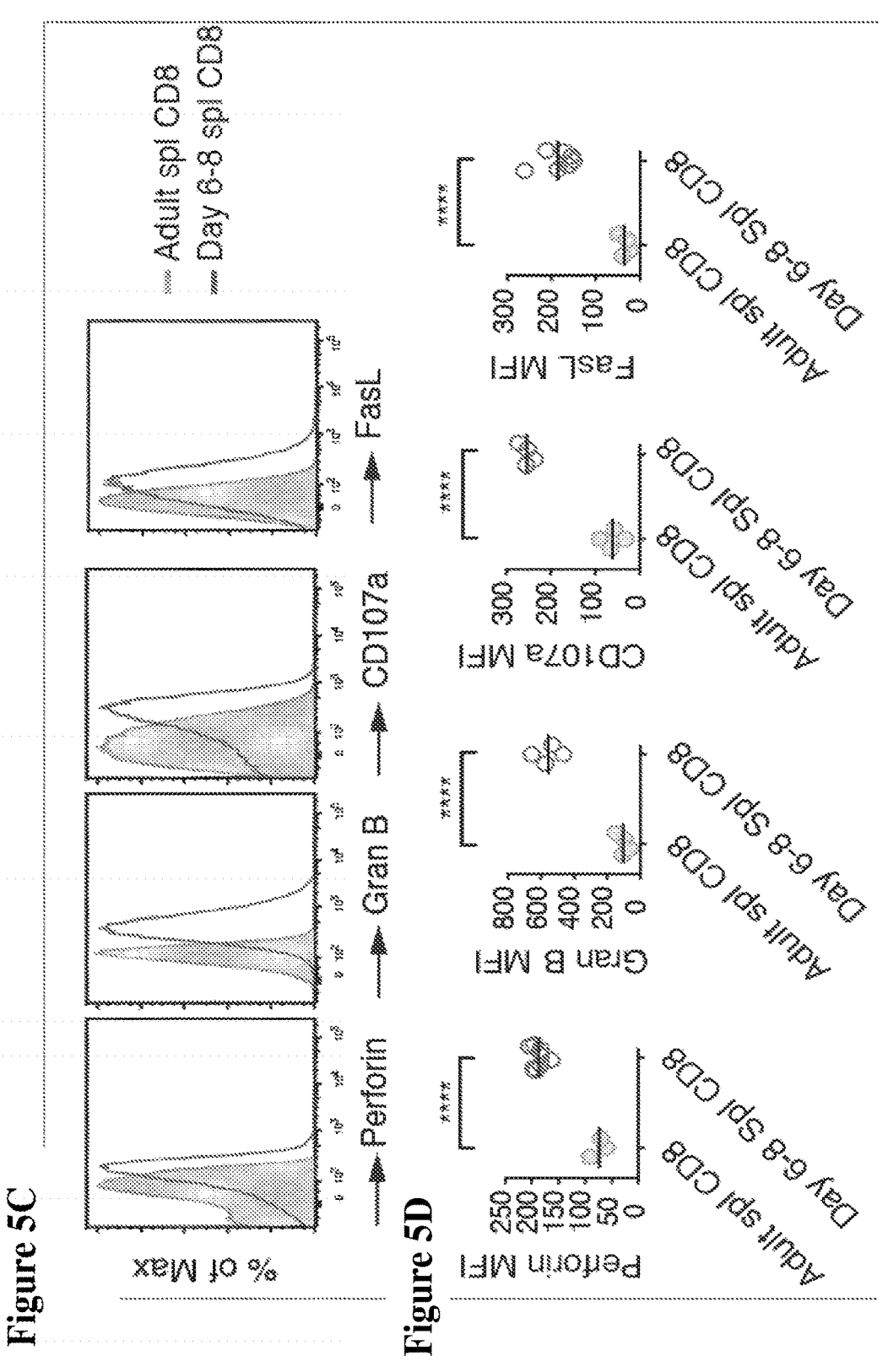
FIG. 5C shows FACS analysis of the indicated effector molecules in primary CD8 T cells isolated from day 6-8 CL mice spleen, compared to primary CD8 T cells from adult CL spleen, demonstrating tumor-killing T cells express key cytotoxic molecules.
FIG. 5D shows mean fluorescence intensities (MFI) of the indicated effector molecules detected as in the FIG. 5C FACS analysis.

Particularly striking was the high level of cytotoxic activity by CD4 cells which had similar cytotoxic function as CD8 cells. CD4 and CD8 cells from the BM and spleen of day 6-8 CL mice displayed potent killing activity on LMP1-expressing lymphoma cells (derived from T cell-deficient CL mice) ex vivo (FIG. 4). Remarkably, CD4 cells isolated from day 6-8 CL mice expressed perforin, granzyme B (GzmB), and CD107a, at levels similar to those of the CD8 cells (FIGS. 5A-D). In addition, these cells expressed high levels of Fas ligand (FasL) but not TRAIL (FIGS. 5A-D and data not shown), suggesting that they kill LMP1-expressing B cells through perforin-granzyme as well as FasL mediated pathways. Yet, given that LMP1-expressing B cells remain controlled in mice deficient for Fas but not in mice deficient for perforin, the perforin-granzyme pathway appears to be the predominant killing mechanism of these cytotoxic T cells. Overall, our data demonstrate that LMP1 expression by B cells induces potent cytotoxic CD4 and CD8 T cell-mediated immunity.

Figures 6A, 6B:
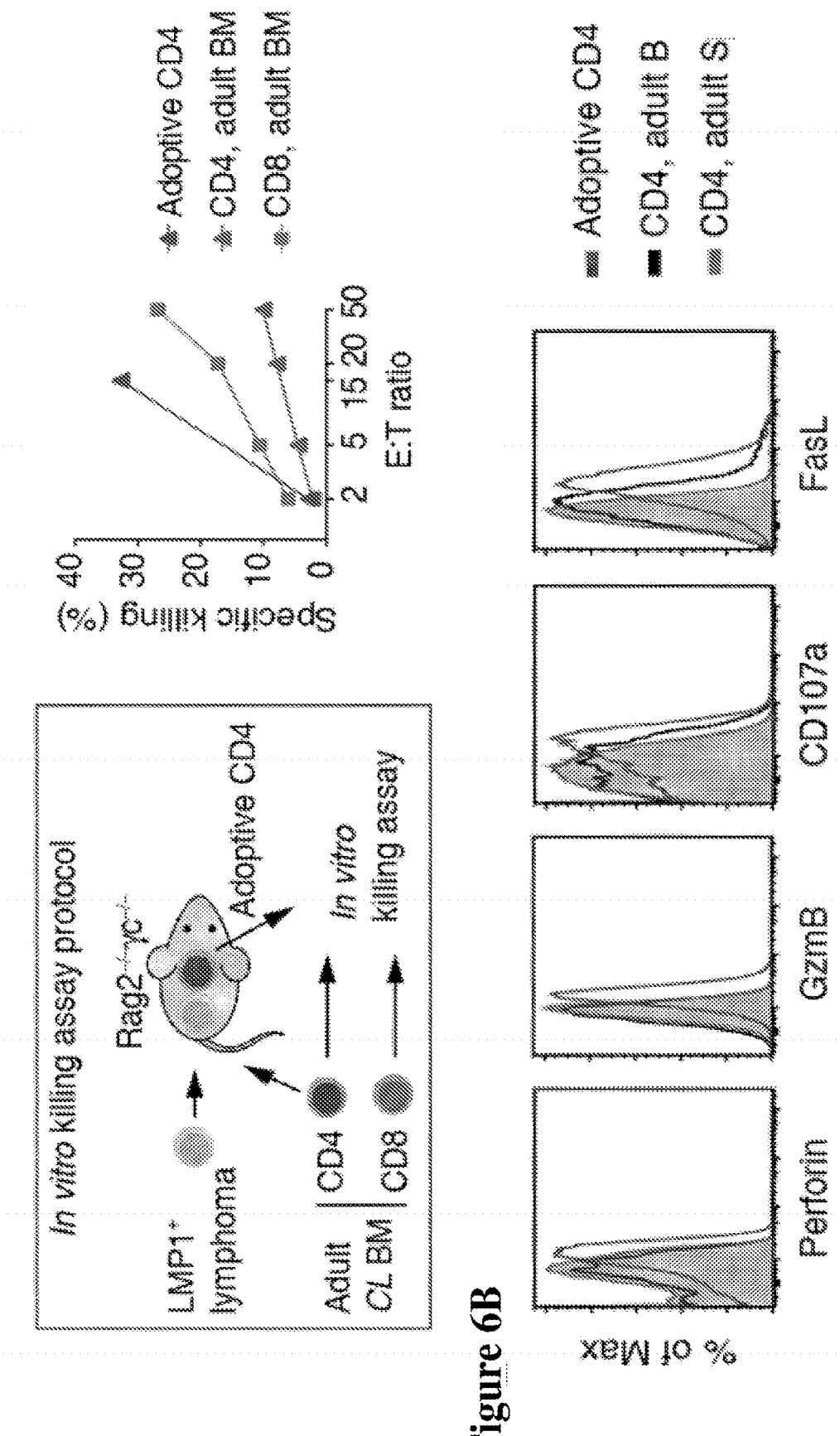
FIG. 6A is a graph showing cytotoxicity of the indicated T cells assayed on LMP1-expressing lymphoma cells as targets. CD4 and CD8 T cells were from adult (day 42-84) CL mice BM; the adoptive CD4 T cells were those initially isolated from adult CL mice BM, adoptively transferred (along with LMP1-expressing lymphoma cells) into Rag2$^{-/-}$ γc$^{-/-}$ recipients, and then recovered from the latter. Representative data from three independent experiments are shown. All mice used here are on a (C57BL/6×BALB/c) F1 (CB6F1) background, while the lymphoma cells are on a C57BL/6×BALB/c mixed background.
FIG. 6B is a representative series of graphs showing the flow cytometry analysis of the indicated effector molecules in the adoptive CD4 cells compared to primary CD4 cells from adult CL mice BM (chronic state) and spleens (negative control).

Although CD4 and CD8 cells in the BM of adult CL mice remain an activated state (CD69$^+$), these CD4 cells exhibited little cytotoxicity, in contrast to CD8 cells from the same mice (FIG. 6A). Nevertheless, when the CD4 cells were co-transferred with LMP1-expressing lymphoma cells into lymphopenic hosts, they exhibited superior anti-tumor activity relative to that of the CD8 cells, and their antitumor activity remained intact in the presence of antibodies blocking IFNγ and TNFα. Remarkably, CD4 cells that were recovered from the adoptive hosts displayed potent killing activity ex vivo (FIG. 6A), associated with expression of cytotoxic molecules—perforin, granzyme B, CD107a and FasL, in sharp contrast to the donor cells prior to transfer (FIG. 6B).

Figure 6C:
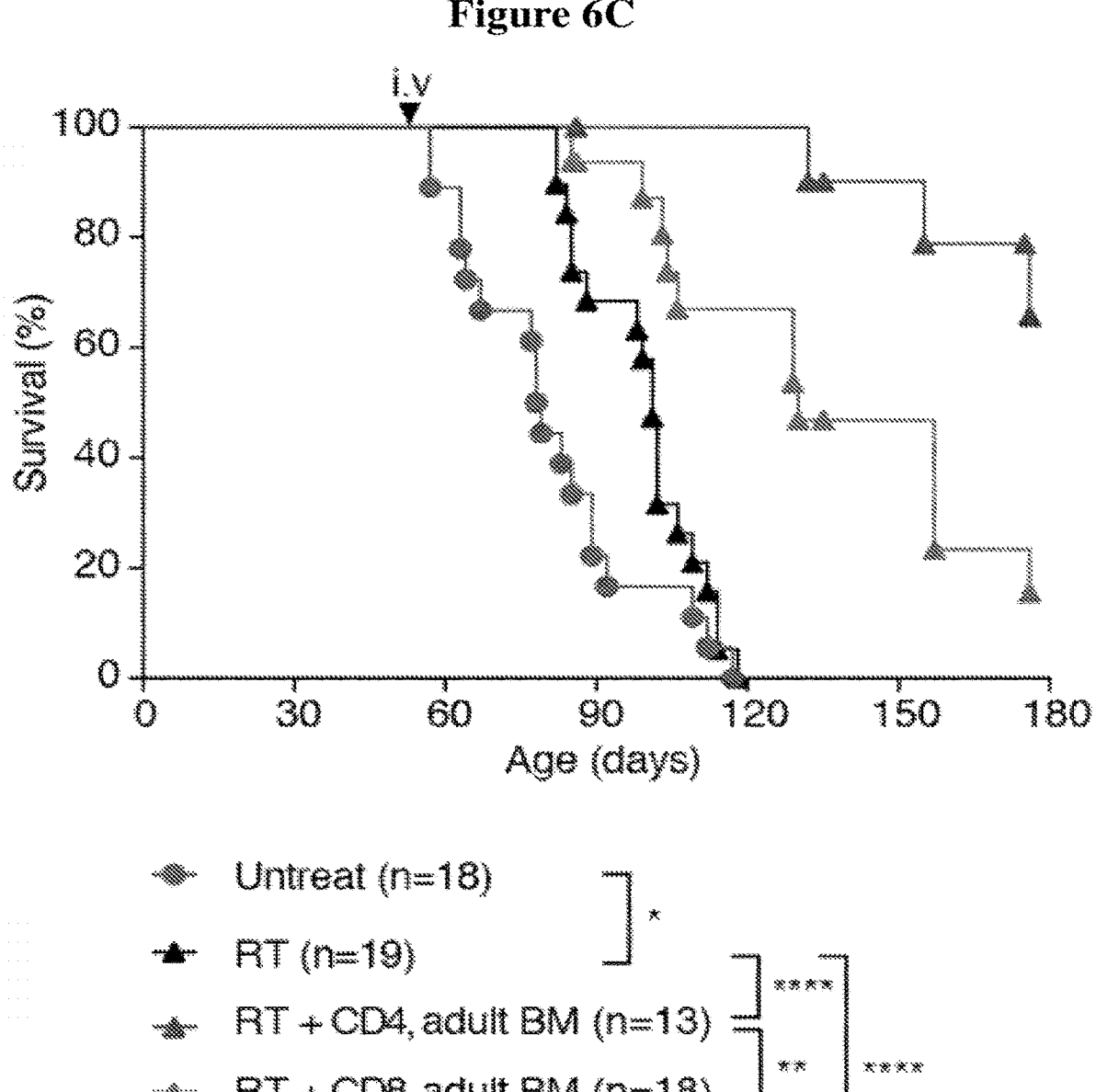
FIG. 6C is a set of survival curves showing the therapeutic efficacies of adoptive CD4 and CD8 cells in combination with radiation therapy (RT) in mice bearing aggressive LMP1-driven primary lymphomas. TCRβ$^{-/-}$δ$^{-/-}$ CL mice on a C57BL/6×BALB/c mixed background at 8-week old were treated with 500 Rad of irradiation. One day later, some mice were further treated (by intravenous injection) with the indicated T cells isolated from CL mice on a CB6F1 background at the dose of 1×10$^6$ cells/recipient. Survival curves were compared using the log-rank test.

The finding that, upon co-transfer with LMP1-expressing lymphoma cells, chronic state CD4 cells regain cytotoxicity and mediate superior antitumor activity relative to that of their CD8 counterparts, prompted us to test and compare these CD4 and CD8 cells for their therapeutic efficacy in LMP1-driven primary lymphomas. Considering that the heavy tumor burden in these mice may establish an immunosuppressive environment and thereby impede the expansion and function of adoptive T cells, we pre-treated the mice with radiation therapy (RT) to reduce the tumor burden and create a lymphopenic condition favorable for adoptive T cell expansion and function, followed by transfer of a single dose ($1 \times 10^6$/recipient) of CD4 or CD8 cells. We found that RT alone moderately improved survival of tumor-bearing mice. The combination with adoptive CD8 cells further prolonged mice survival, and CD4 cells displayed even stronger antitumor activity than the CD8 cells (FIG. 6C). Thus, CD4 cells, upon developing into cytotoxic effectors, can be superior to CD8 cells in tumor control, as demonstrated in this primary lymphoma model.

Figure 7A:
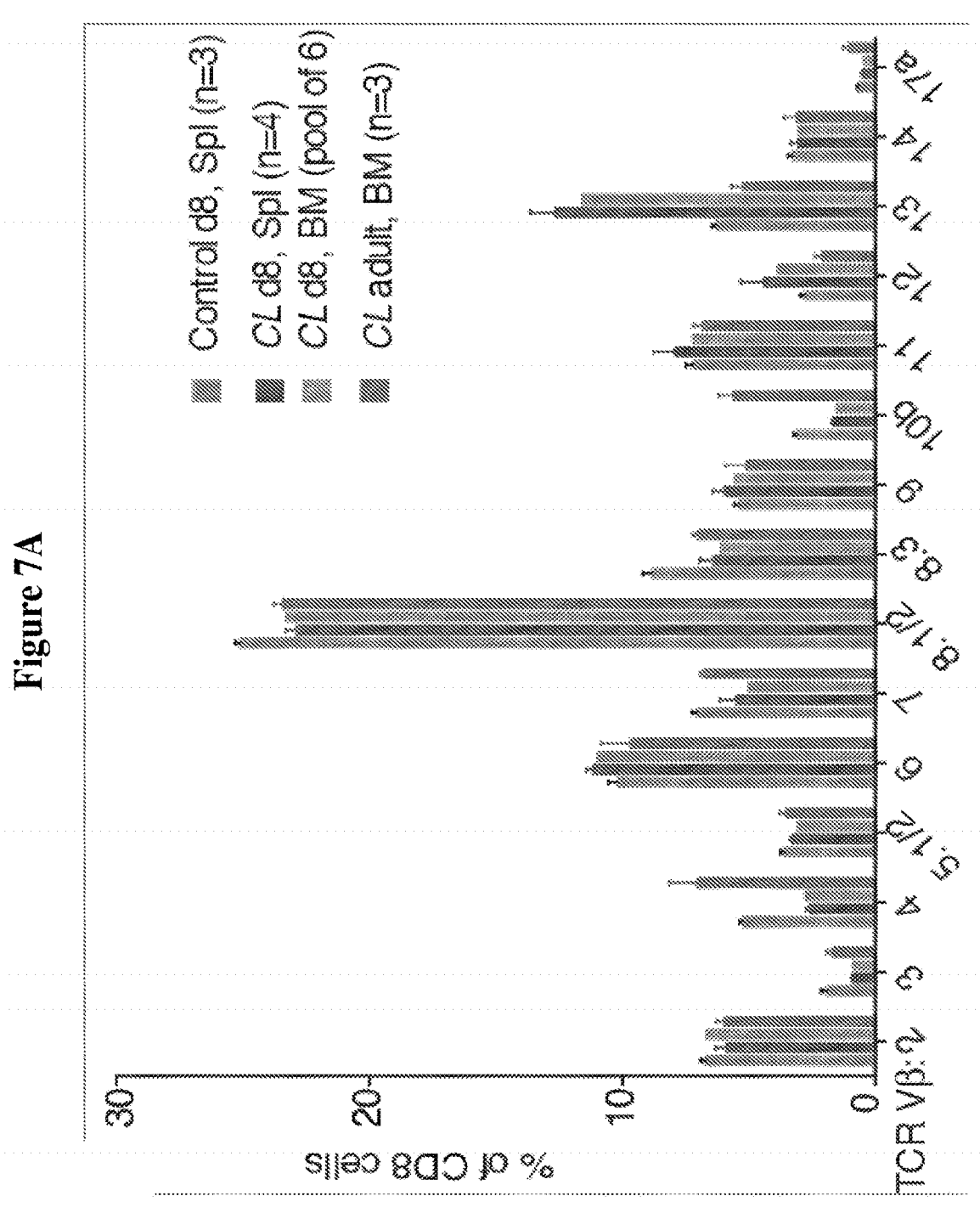
FIG. 7A is a bar graph showing TCR Vβ chains in CD8 T cells from the indicated mice that were stained with a panel of monoclonal antibodies for the indicated TCR Vβ chains. These Vβ specific antibodies collectively detected 85-95% of TCRs in all the samples. Control d8, day 8 old CD19-cre/+ mice. Data are shown as mean±SEM.
Figures 7B, 7C:
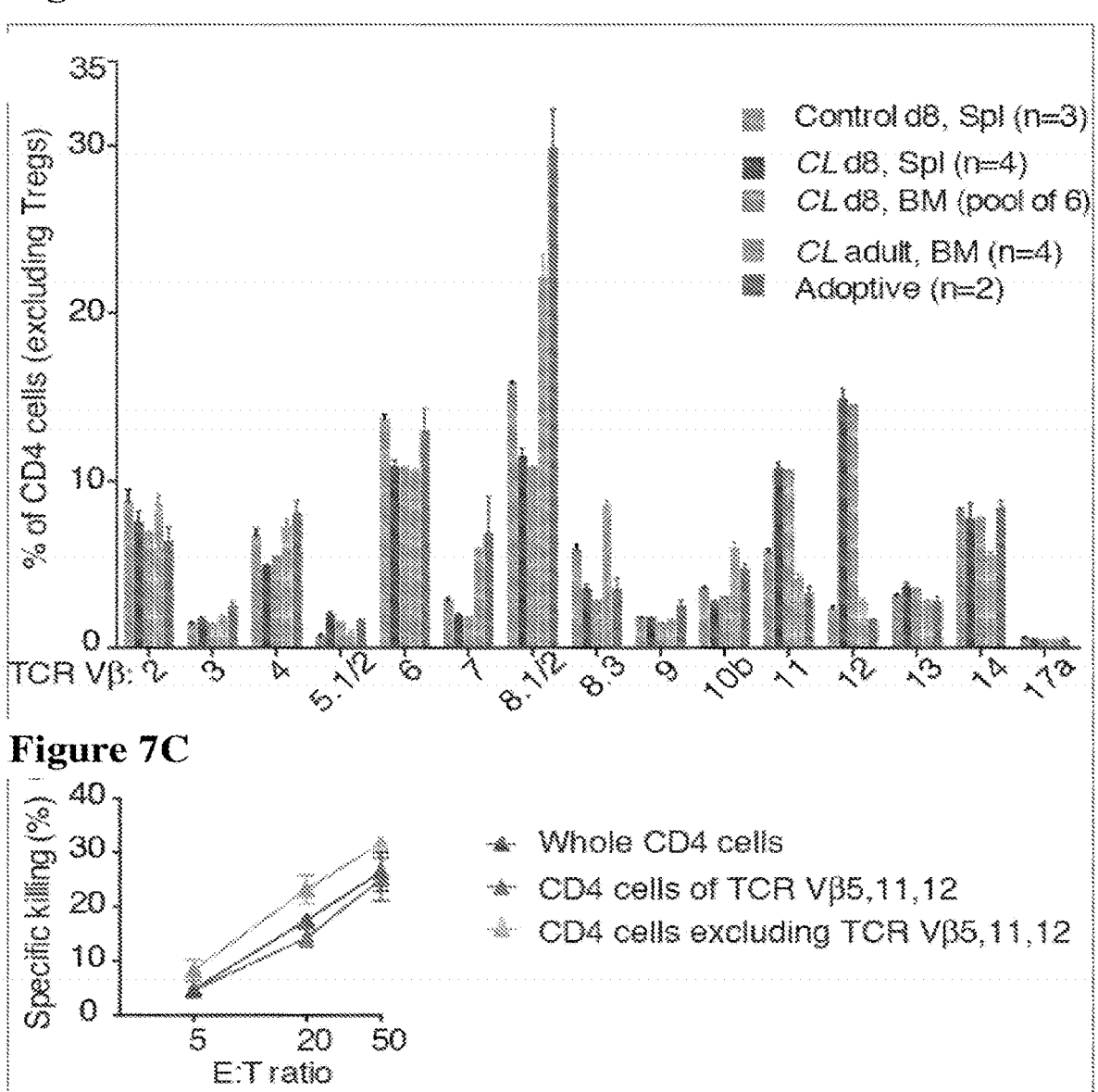
FIG. 7B is a bar graph showing TCR Vβ chains in CD4 T cells (excluding CD25$^+$Foxp3$^+$ Tregs) from the indicated mice that were stained with a panel of monoclonal antibodies for the indicated TCR Vβ chains. These Vβ specific antibodies collectively detected 85-95% of TCRs in all the samples. Control d8, day 8 old CD19-cre/+ mice; the adoptive CD4 T cells were those initially isolated from adult CL mice BM, adoptively transferred (along with LMP1-expressing lymphoma cells) into Rag2$^{-/-}$γc$^{-/-}$ recipients, and then recovered from the latter. Data are shown as mean±SEM.
FIG. 7C is a graph showing in vitro killing activity of the indicated CD4 T cells from day 6-8 CL mice, assayed on LMP1-expressing lymphoma cells. Data are shown as mean±SEM of duplicates. Representative data from two independent experiments are shown. CL and control mice used here are on a CB6F1 background.

Example 3. CD4 and CD8 T Cells Mount a Polyclonal Response to LMP1-Expressing B Cells To assess the diversity of T cells involved in the immune response, we assessed the TCR Vβ repertoire on CD4 (excluding CD25$^+$Foxp3$^+$ Tregs) and CD8 cells from day 6-8 CL mice (these cells have high killing activity and express the effector memory marker CD44), in comparison with those from control mice (CD19-cre/+). We also examined T cells from the BM of adult CL mice, in which CD4 cells exhibit minimum killing activity, while CD8 cells retain good killing activity (the majority of these CD4 and CD8 cells are antigen-specific). CD8 cells from day 6-8 and adult CL mice displayed polyclonal VPs (day 6-8 CL mice showed a modest increase in Vβ13, while in adult CL mice Vβ13 levels were similar to those in control mice; FIG. 7A). CD4 cells from day 6-8 CL mice also displayed a grossly polyclonal response, though a few Vβ TCRs (Vβ5, –11 and –12) showed variable degrees of enrichment compared to those in control mice (FIG. 7B). By in vitro killing assay, CD4 cells bearing Vβ5, –11 and –12 TCRs displayed similar killing activity as cells carrying the other TCRs (FIG. 7C), indicating that the killing activity of CD4 cells in CL mice is not associated with restricted TCR Vβ chains, and making it unlikely that the response is mediated by a superantigen. In the BM of adult CL mice, the frequencies of the Vβ5, –11 and –12 TCRs had diminished to levels comparable to those seen in control mice, while Vβ8.1/8.2 TCRs were skewed at this chronic stage (FIG. 7B). Upon adoptive transfer, CD4 cells from the BM of adult CL mice carried over their broad TCR repertoire (FIG. 7B), but they had regained killing activity (FIG. 6). The further skewing of Vβ8.1/8.2 TCRs might be due to their dominance in the donor cells (FIG. 7B). These observations reiterate that the killing activity of the T cells is not associated with restricted TCR Vβ chains. Overall, these data indicate that both CD4 and CD8 T cells mount a polyclonal response to LMP1-expressing B cells.

Figure 8:
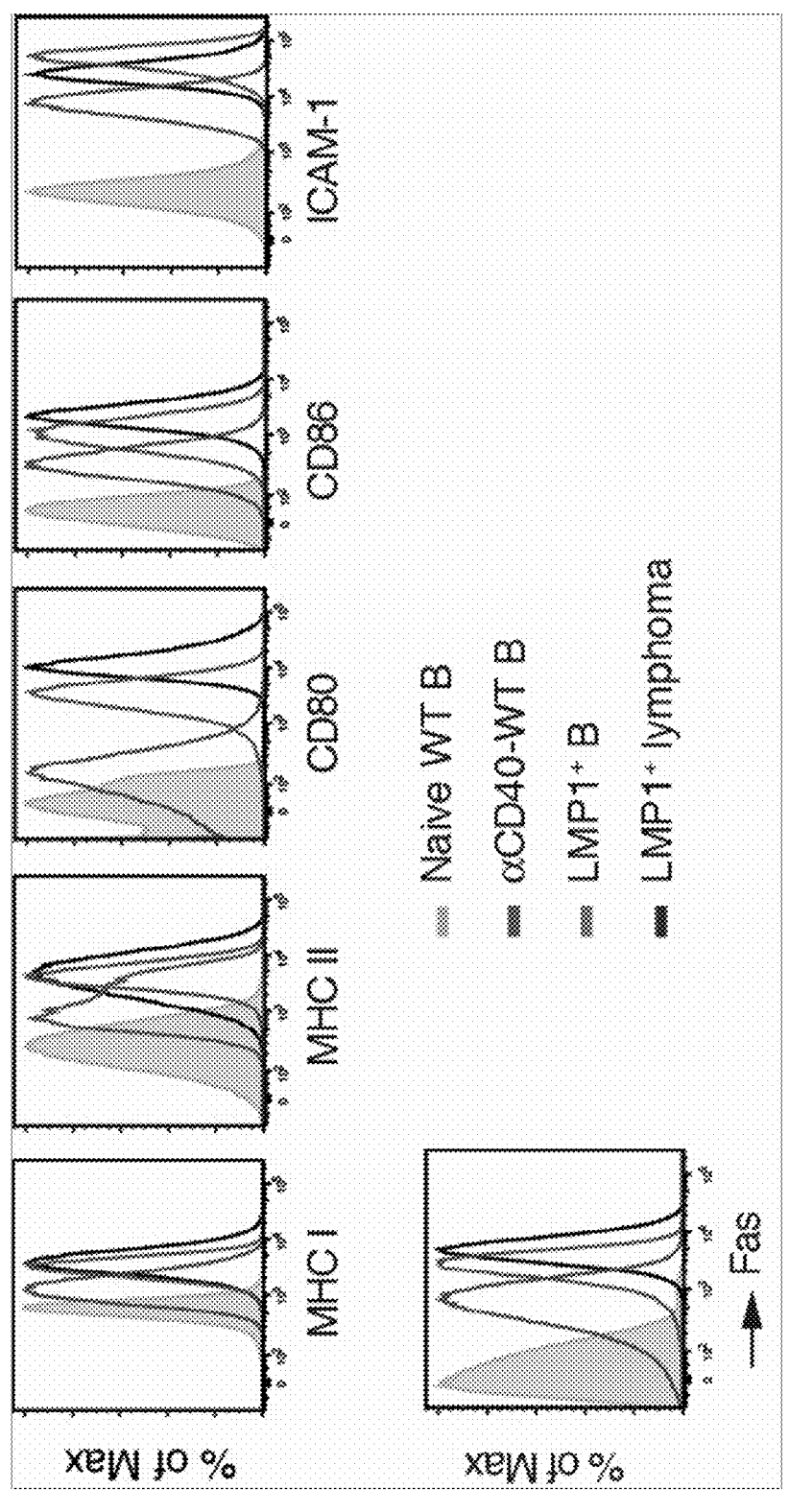
FIG. 8 shows FACS analysis of naïve B cells, CD40-activated B cells from wild-type (WT) mice, LMP1-expressing lymphoma B cells and B cells from LMP1$^{flSTOP}$ mice treated with TAT-Cre to turn on LMP1 expression in vitro (LMP1-expressing B cells).

Example 4. T Cells Recognize CD40-Activated B Cells that Lack LMP1 Expression LMP1 has been characterized as a functional analog of constitutively active CD40, which is a major co-stimulatory receptor for the functional maturation of antigen-presenting cells (APCs). We found that, similar as activation of CD40, LMP1 expression in B cells resulted in upregulation of key proteins critical for the induction of a productive T cell response, including MHC-I, MHC-II, CD80/B7-1, CD86/B7-2 and ICAM-1 (many of these molecules were even higher than those in CD40-activated B cells (FIG. 8). These would presumably lead to enhanced antigen presentation and co-stimulation, including presentation of endogenous antigens (Rowe et al., 1995; Schultze et al., 1995; Schultze et al., 1997; Smith et al., 2009).

Figures 9A, 9B:
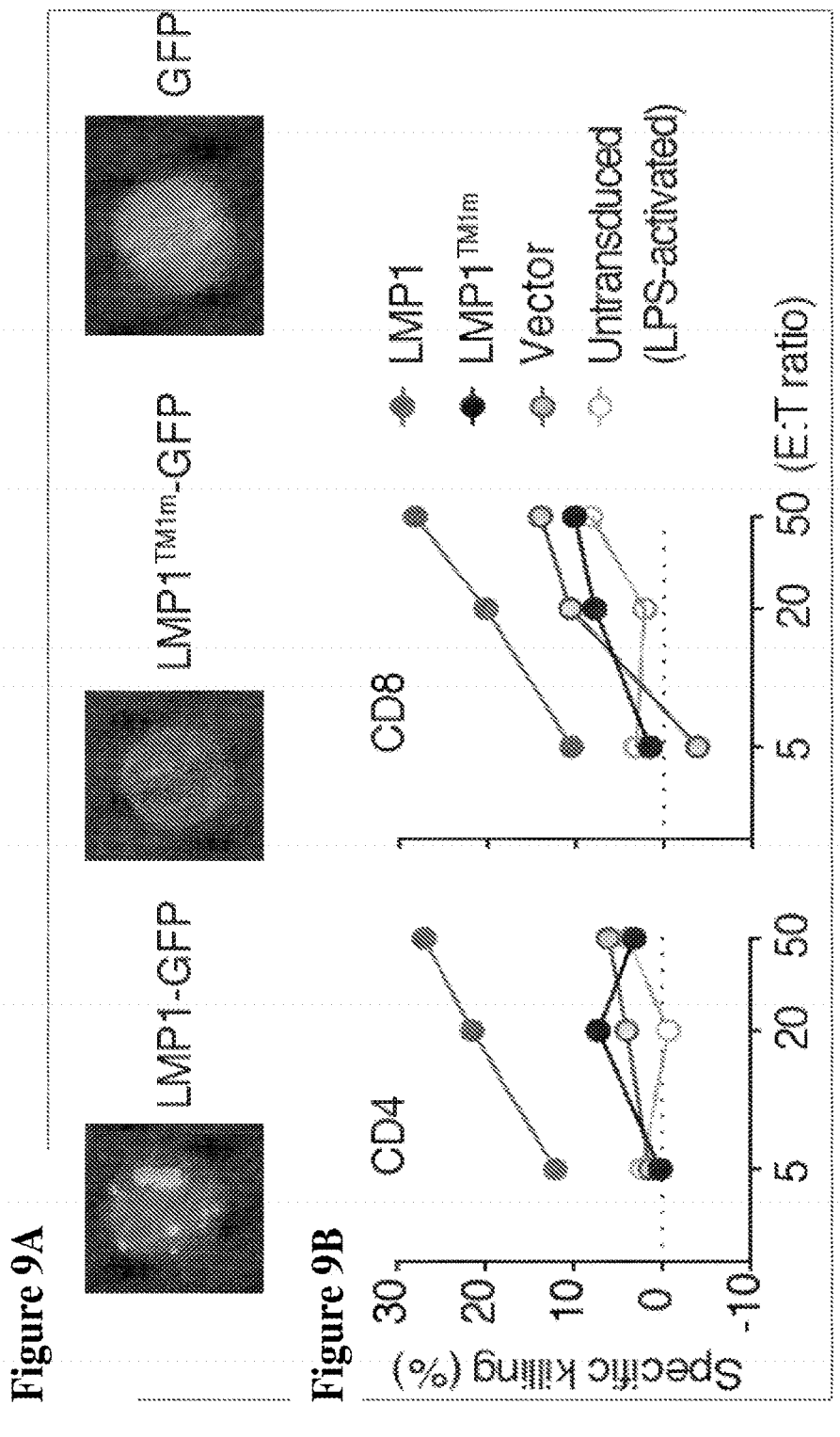
FIG. 9A shows fluorescent microscopy imaging of B cells expressing LMP1-GFP fusion, LMP1$^{TM1m}$-GFP fusion or GFP, respectively. Note that wild-type LMP1 aggregates into large complexes on cell membrane, while the mutant LMP1$^{TM1m}$ loses its ability to aggregate.
FIG. 9B is a pair of graphs showing CD4 T cells (left panel) and CD8 T cells (right panel) from day 6-8 CL mice assayed for killing activity on B cells (from WT B6 mice) transduced with retroviral vectors expressing wild-type LMP1 or a signaling-dead mutant LMP1$^{TM1m}$. B cells untransduced or transduced with the empty vector as controls.

To determine if LMP1 signaling-induced B cell hyper-immunogenicity is essential for the T cell response, we constructed an LMP1 mutant in which amino acids FWLY (38-41) of transmembrane domain 1 (TM1) were changed to AALA (referred to as LMP1$^{TM1m}$): this abolishes LMP1 clustering and signaling (Yasui et a, 2004) (FIG. 9A) and presumably its immune-stimulatory function (Smith et al., 2009). In an in vitro killing assay, cytotoxic CD4 and CD8 T cells from day 6-8 CL mice efficiently recognized and killed B cells expressing wild-type LMP1 but not B cells expressing the signaling-dead mutant LMP1$^{TM1m}$, or the vector-transduced or untransduced control B cells (the latter cells are in fact LPS-activated B cells) (FIG. 9B). Thus, T cell recognition of LMP1-expressing B cells requires LMP1 signaling, which renders the B cells highly immunogenic.

Figure 10A:
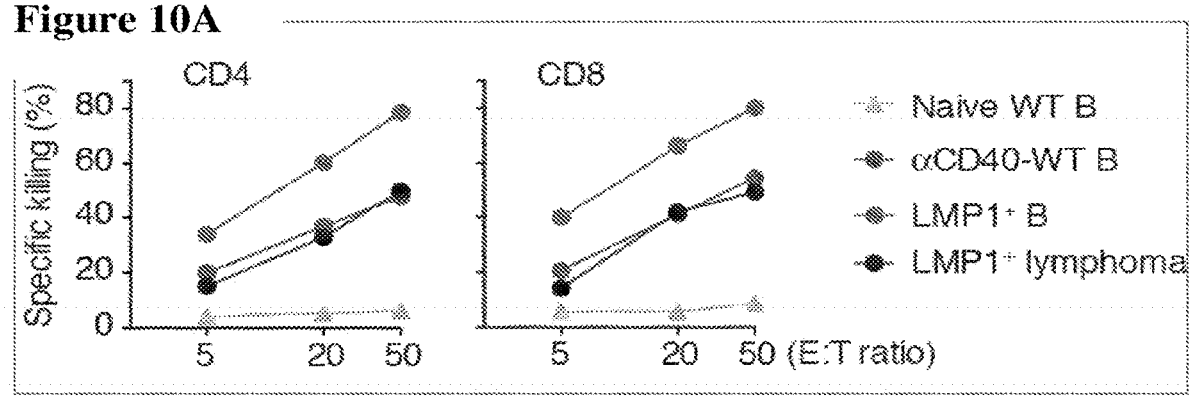
FIG. 10A is a pair of graphs showing that CD4 and CD8 T cells from day 6-8 CL mice lyse LMP1-expressing B cells/lymphoma cells as well as anti-CD40 pretreated WT B cells, but not naïve B cells.
Figure 10B:
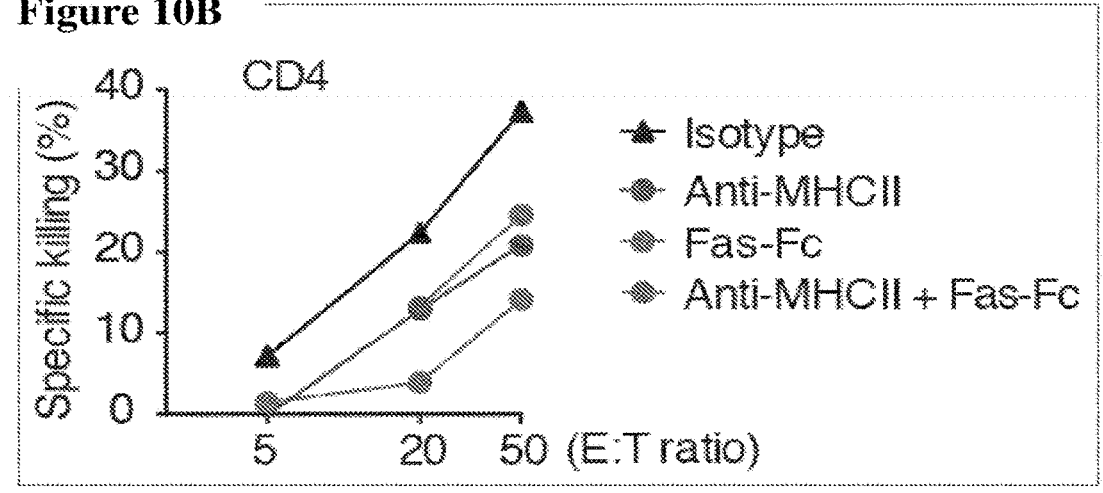
FIG. 10B is a graph showing the results of an in vitro killing assay performed with CD4 T cells from day 6-8 CL mice on CD40-activated WT B cells (from B6 mice), in the presence of Fas-Fc (to block FasL-mediated killing) and/or MHCII blocking antibody.

Because LMP1 is a functional analog of constitutively active CD40, and because LMP1 and CD40 both activate the immunogenicity of B cells and possibly enhance endogenous antigen presentation (see above), we tested whether primed T cells from CL mice recognize CD40-activated wild-type (WT) B cells via the cellular antigens that they share with LMP1-expressing B cells. We found that cytotoxic CD4 and CD8 T cells from day 6-8 CL mice lysed WT B cells that were pre-activated with anti-CD40, but not resting (naïve) B cells (FIG. 10A). These data suggest that B cells with LMP1 signaling provide endogenous antigens to be targeted by cytolytic T cells. The CD4 T cell killing activity of CD40-activated WT B cells was suppressed by blocking recognition of MHC class II (FIG. 10B). Killing could also be decreased by blocking the FasL-Fas apoptotic pathway (CD40-activated B cells express Fas, as do LMP1-expressing B cells (FIG. 8)), and blocking both MHC-II and FasL led to a more substantial reduction in the killing activity (FIG. 10B). These data suggest that cytotoxic T cells target LMP1-expressing B cells by recognizing self-peptide/MHC complex and exert their cytolytic activity by perforin-granzyme and FasL-Fas dependent pathways.

Unambiguous evidence that the T cells in CL mice recognize self-peptide/MHC complexes was obtained by analyzing the proliferative responses of CD4 effector/memory T cells (excluding Foxp3$^+$ Tregs which are known to be self-reactive) on CD40-activated B cells, derived from WT versus CIITA$^{-/-}$ (lacking MHC-II expression) mice. A significant fraction of the effector/memory CD4 cells proliferated vigorously on CD40-activated WT B cells in an MHC-II restricted manner (FIG. 11).

Figure 11:
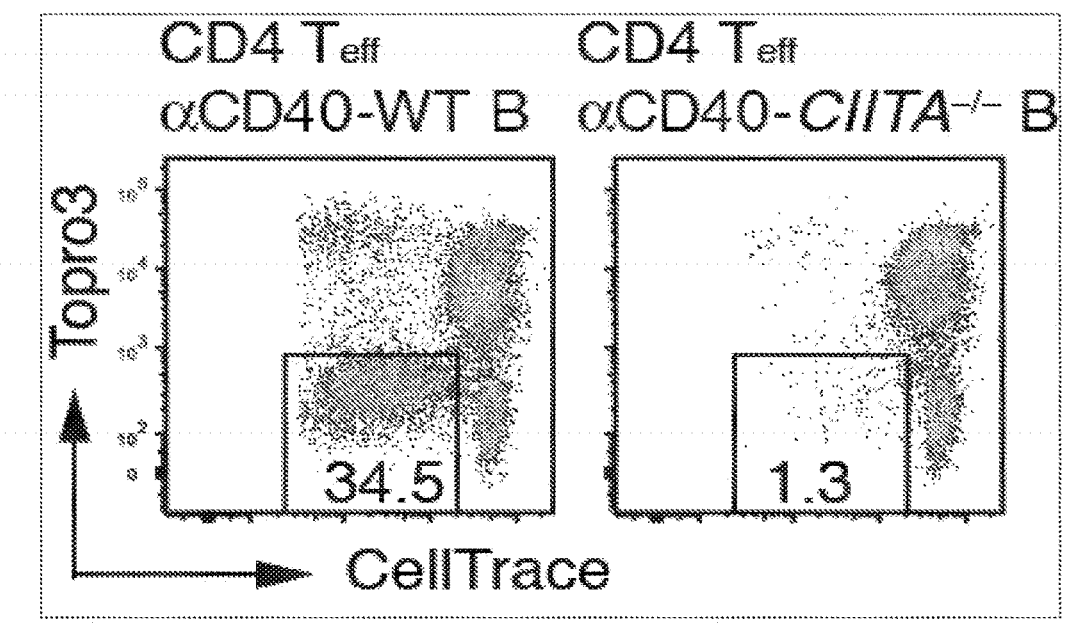
FIG. 11 shows FACS analysis of CD4$^+$ effector/memory T cells (excluding Tregs) from Foxp3$^{GFP}$; CL male mice that recognize and proliferate on CD40-activated WT B cells in an MHC-II restricted manner.

Together, our data indicate that T cells recognize and lyse LMP1-expressing B cells via cellular antigens, some of which are also presented on WT B cells that are activated through the analogous CD40 pathway (FIGS. 10-11). Because the cytotoxic T cells from CL mice do not lyse resting B cells (FIG. 10A) nor WT B cells activated by LPS (through a pathway unrelated to LMP1 signaling; FIG. 9B), it appears that cellular antigens induced by LMP1 signaling, rather than common B cell antigens, are the main targets of T cells. Given that the TCR repertoire during the acute phase of the immune response is very diverse (similar to that in naïve mice) and that there is no clonal deletion of any Vβ TCR afterwards (FIG. 7A-C), it can be inferred that the T cells target a large number of LMP1 signaling-induced cellular antigens, but not a superantigen. At present, we cannot exclude the involvement of LMP1-derived peptides in the T cell response in CL mice. However, such response might be too small to be detectable with our previous peptide screening assay.

Example 5. LMP1 Induces Immune Surveillance Independent of CD40 Signaling

Figures 12A, 12B, 12C:
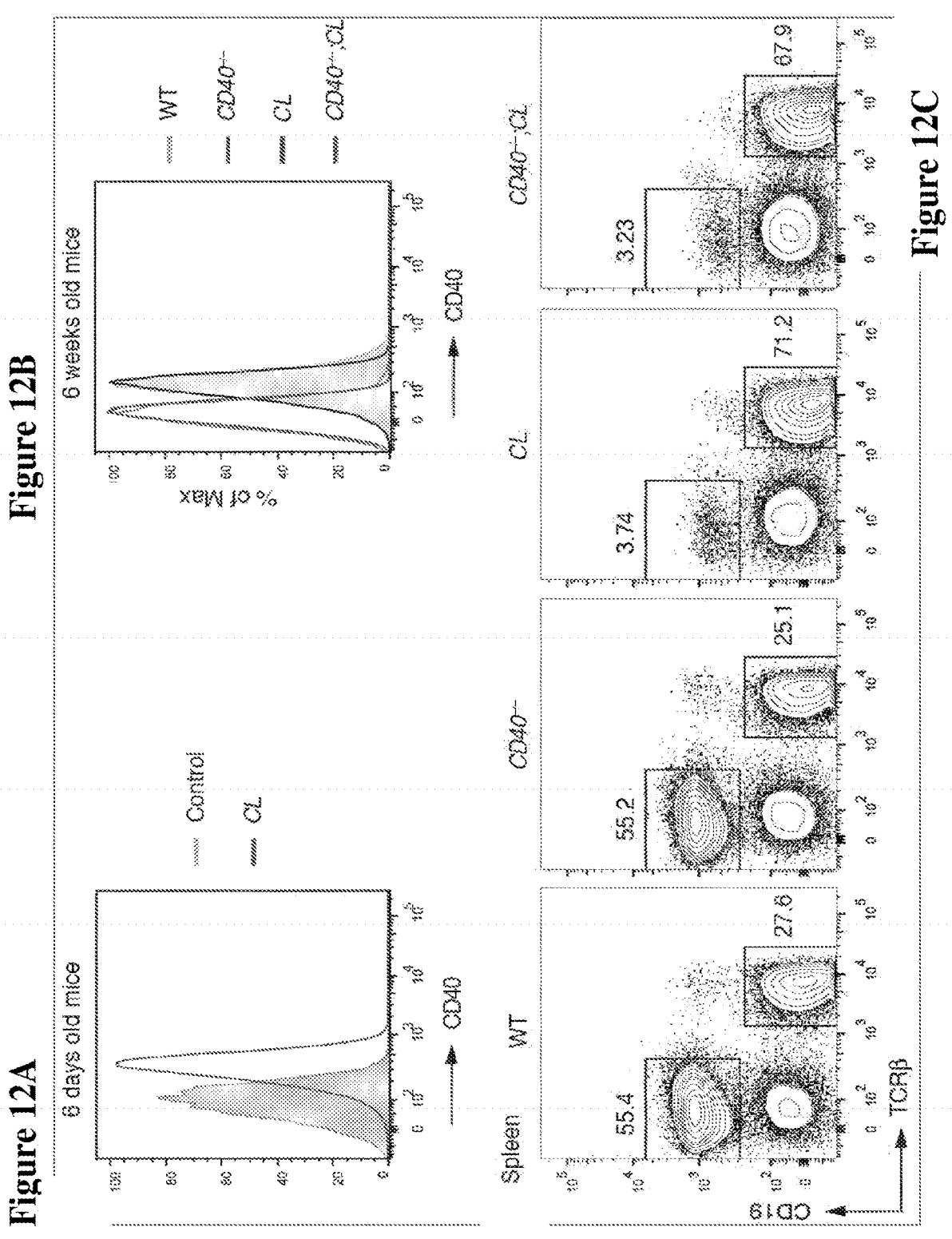
FIG. 12A shows FACS analysis of CD40 expression on LMP1-expressing B cells from a 6-day old CL mouse, compared to that on B cells from a littermate control (CD19-cre/+). Note that LMP1 signaling in B cells upregulates CD40.
FIG. 12B shows FACS analysis of CD40 expression on B cells from the indicated mice at 6 weeks old. Note that the B cells in CL and CD40$^/$; CL mice represent residual B cells (which do not express LMP1) after clearance of LMP1-expressing B cells.
FIG. 12C shows FACS analysis of B cells and T cells in spleens of the indicated mice at 6 weeks old.
Figure 12D:
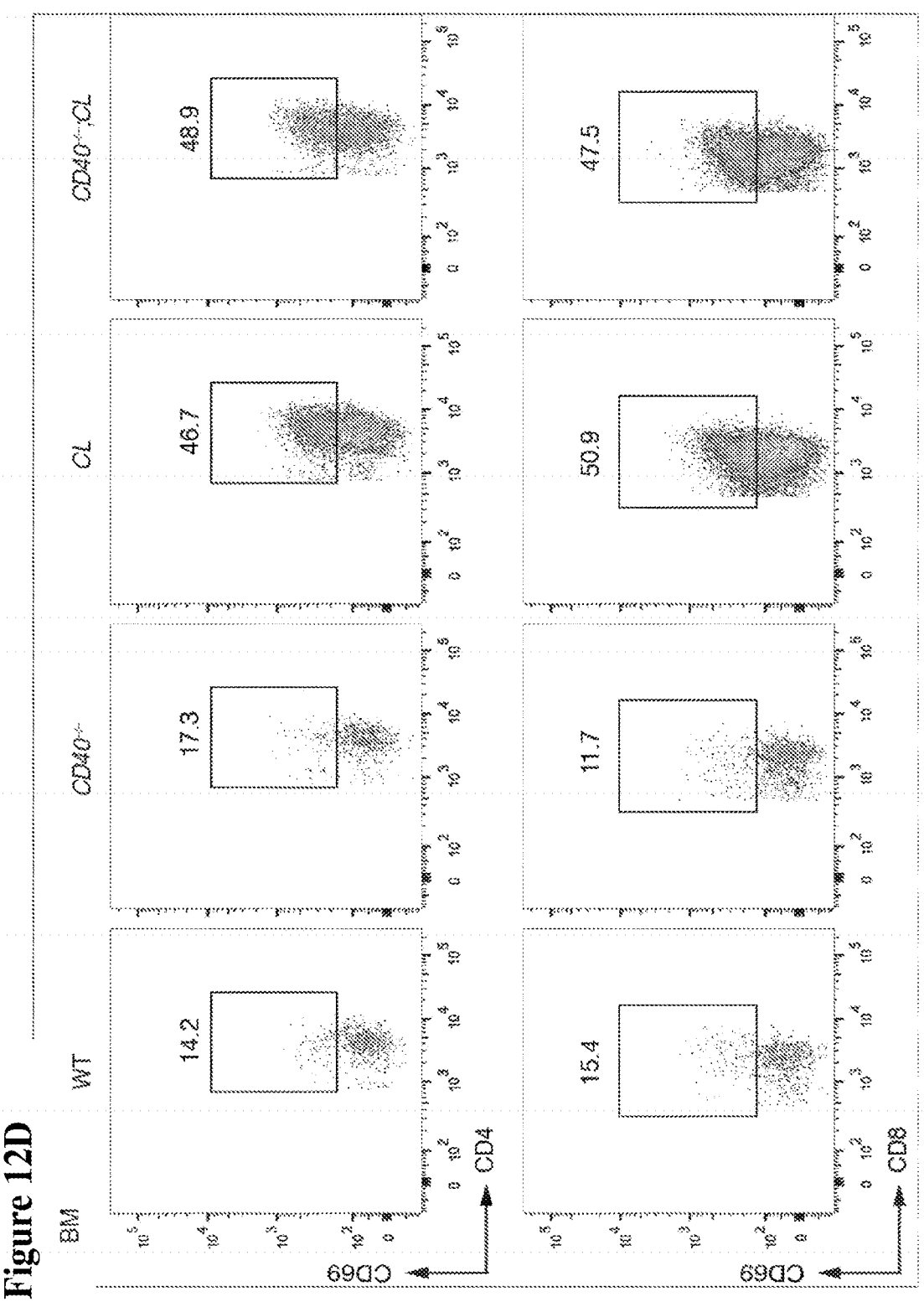
FIG. 12D shows FACS analysis of activation marker CD69 on CD4 and CD8 T cells from the BM of the indicated mice at 6 weeks old. Data in (A-D) represent 2-3 mice analyzed for each genotype.

Although LMP1 signaling and constitutive CD40 activation enhanced cellular antigen presentation as well as co-stimulation to a certain degree, immune surveillance was only seen in mice whose B cells expressed LMP1, but not in mice whose B cells expressed an LMP1-CD40 fusion protein (LMP1 transmembrane region fused to the intracellular signaling domain of CD40, thereby making CD40 pathway constitutively active; both mouse models used the same gene expression strategy, namely knocking-in to the Rosa26 locus) (Homig-Holzel et al., 2008; Zhang et al., 2012). These results suggest that the LMP1 signaling domain is distinct from that of CD40, in its ability to induce immune surveillance. However, considering that LMP1 signaling in B cells upregulates CD40 expression (FIG. 12A), we addressed the possibility that LMP1 induces immune surveillance by potently amplifying CD40 signaling by breeding CL mice to a CD40$^{-/-}$ background. Comparing CL mice on a CD40-null versus -WT background indicated that LMP1-expressing B cells were efficiently eliminated by activated CD4 and CD8 T cells irrespective of CD40 status (FIG. 12B-D). In other words, LMP1 induces immune surveillance independent of CD40 signaling.

Figure 13C:
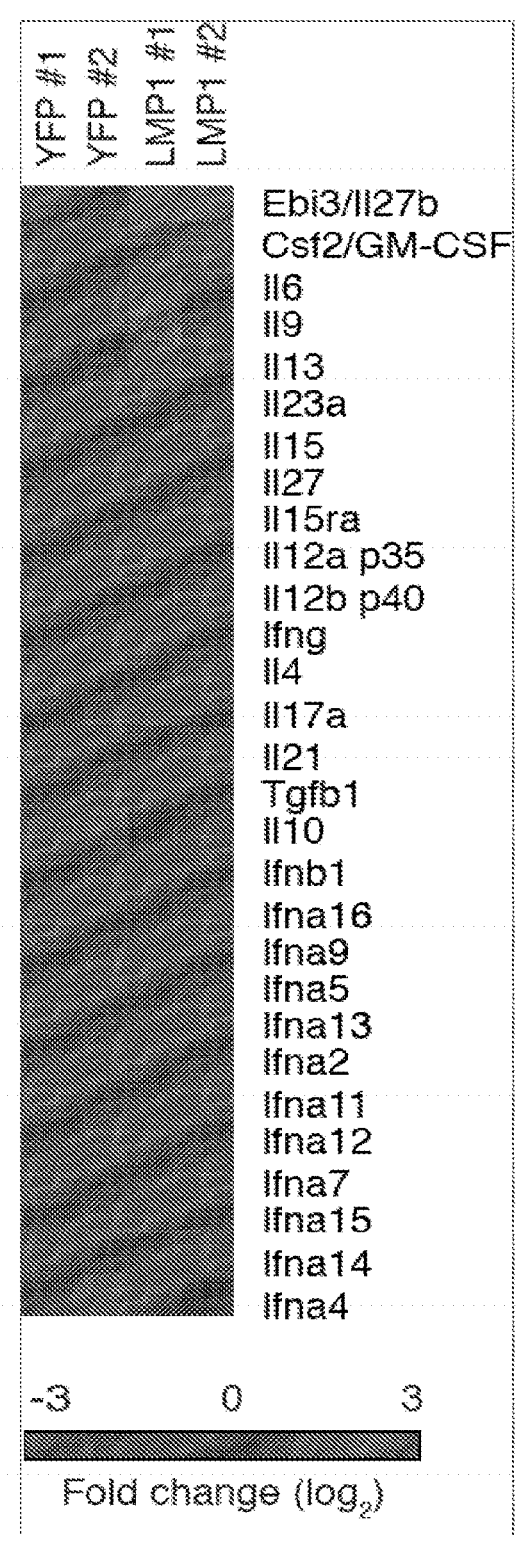
FIG. 13C is a heat map showing cytokine genes expressed in LMP1-expressing B cells compared to control B cells. Splenic B cells from LMP1$^{flSTOP}$/YFP$^{flSTOP}$ and YFP$^{flSTOP/+}$ mice (both on a CB6F1 background) were treated with TAT-Cre to generate LMP1-expressing B cells and YFP control B cells. All treated B cells were collected at day 2 post-treatment for array analysis. Mean-centered log$_2$ gene expression ratios are depicted by color scale.

Example 6. LMP1-B Cells Drive Cytotoxic T Cells Via Co-Stimulation by CD70, OX40L and 4-1BBL We next sought to uncover the molecular mechanisms via which LMP1 signaling induces potent cytotoxic T cell responses. While CD8 T cells inherently develop cytotoxic capacity upon priming with antigens and various co-stimulatory signals, CD4 T cells are multipotential yet uniquely polarized towards the cytotoxic phenotype in our system, we thus focused on identifying co-stimulatory molecules that were expressed on LMP1-expressing B cells and able to induce the cytotoxic differentiation of CD4 cells. Recently, similar granzyme/perforin-featured cytotoxic CD4 T cells have been described, whose differentiation is fully dependent on the T-box transcription factor Eomesodermin (Eomes), but not on the Th1 polarizing T-bet (Curran et al., 2013; Qui et al., 2011; Swain et al., 2012). Furthermore, systemic activation of 4-1BB and/or OX40 co-stimulatory pathways (by agonist antibodies) induces high levels of Eomes in antigen-primed CD4 cells, which then drives their cytotoxic differentiation (Curran et al., 2013; Qui et al., 2011). Systemic CD27 activation also induces Eomes expression in CD4 cells (Curran et al., 2013). Our data show that LMP1-expressing B cells express greatly enhanced levels of 4-1BB ligand (4-1BBL), OX40 ligand (OX40L) and CD70 (CD27 ligand), compared to control B cells (FIG. 13A-B). Proinflammatory cytokines, including IL27 and IL15, may also play a supportive role in cytotoxic CD4 cell generation (Curran et al., 2013). However, with the exception of the gene for the IL27 subunit β, the other cytokine genes were only marginally, if at all, induced in LMP1-B cells (FIG. 13C).

Figure 14A:
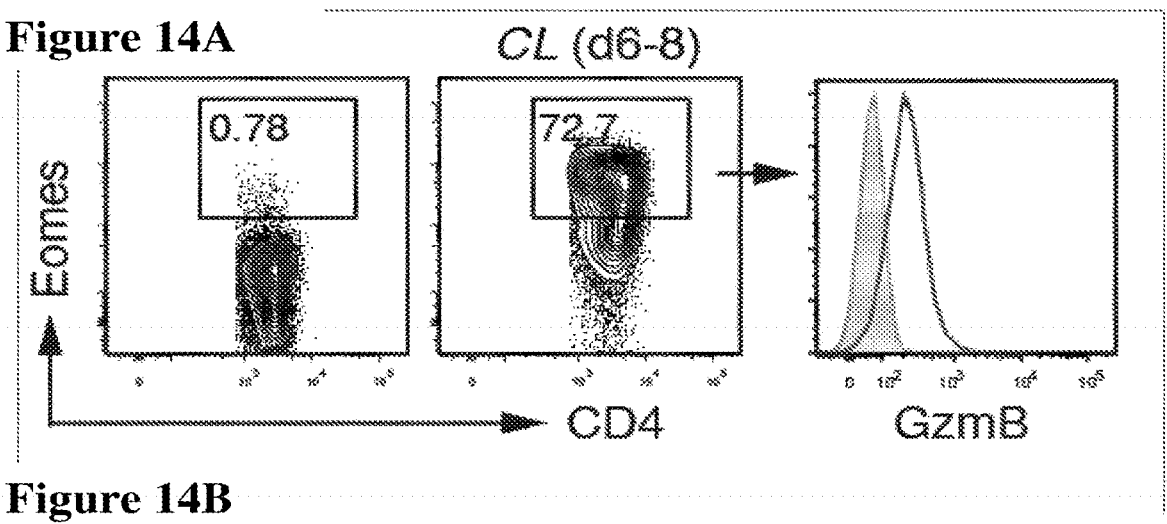
FIG. 14A shows FACS analysis of Eomes and GzmB expression in CD4 T cells from day 6-8 CL mice and WT control (ctr) mice. GzmB levels in Eomes$^+$ CD4 cells from CL mice were compared to that in total CD4 cells from control mice and shown on the right.
Figure 14B:
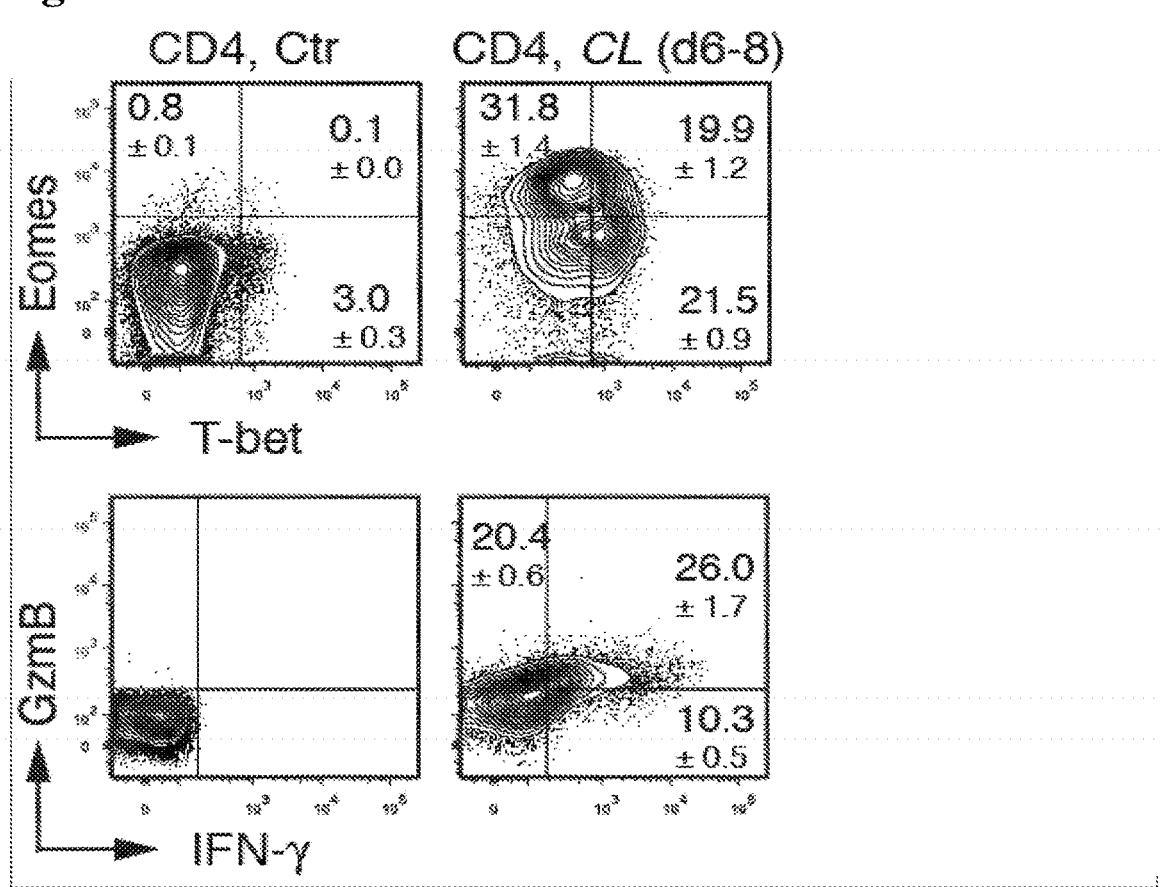
FIG. 14B shows FACS analysis of Eomes vs. T-bet (upper panel) and GzmB vs. IFN-γ (lower panel) in CD4 T cells from day 6-8 CL mice and WT control (ctr) mice. The frequencies (mean±SEM) of indicated populations are shown within the gates.
Figures 14C, 15A, 15B:
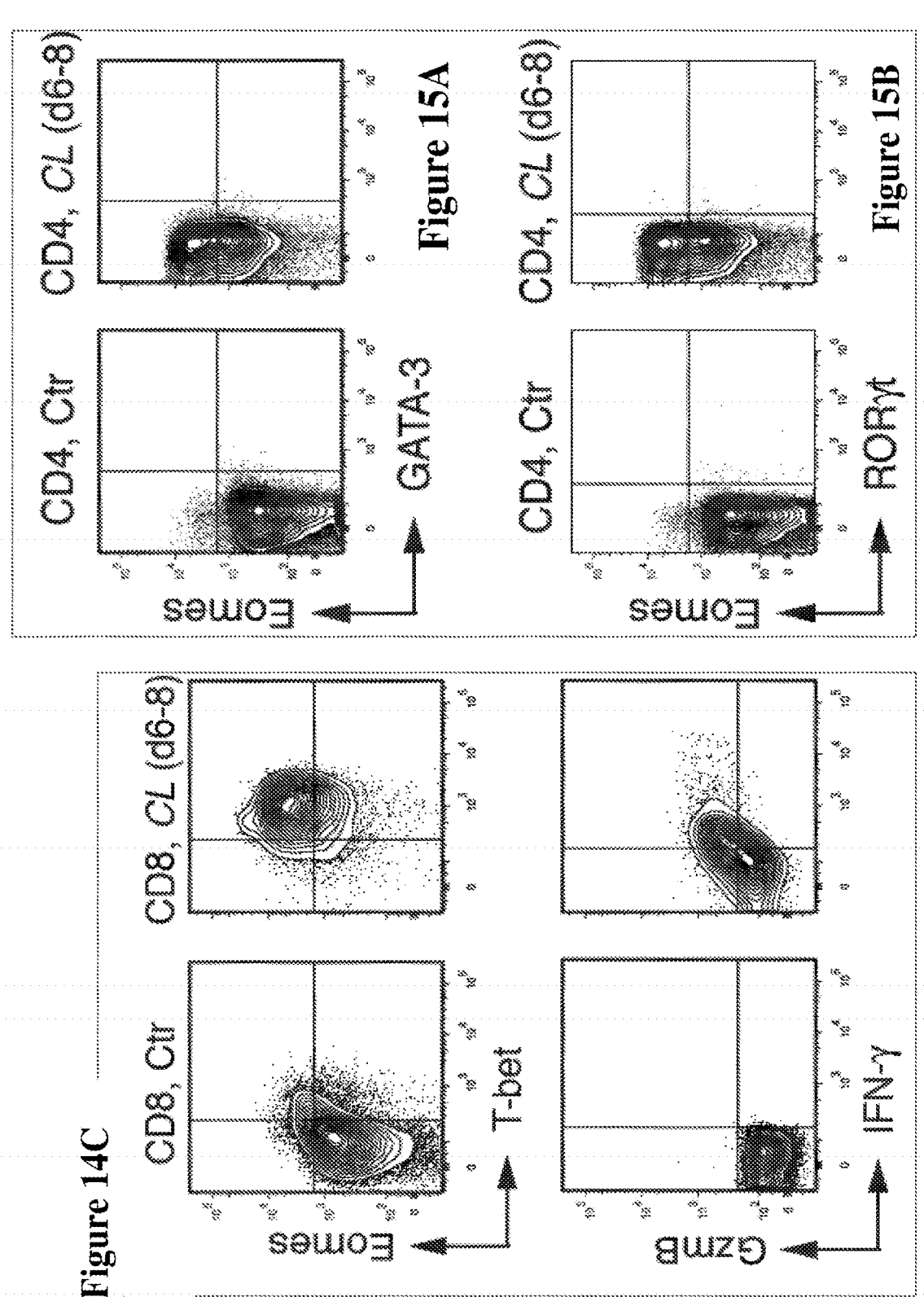
FIG. 14C shows FACS analysis of Eomes vs. T-bet (upper panel) and GzmB vs. IFN-γ (lower panel) in CD8 cells from day 6-8 CL mice and WT control (ctr) mice. Data in (A-C) are representative of 3-4 mice of each group (all on a CB6F1 background), analyzed in two independent experiments.
FIG. 15A shows FACS analysis of Eomes vs. GATA-3 in CD4 cells from day 6-8 CL mice and WT control (ctr) mice. Data are representative of 3-4 mice of each group (all on a CB6F1 background), analyzed in two independent experiments.
FIG. 15B shows FACS analysis of Eomes vs. RORγt in CD4 cells from day 6-8 CL mice and WT control (ctr) mice. Data are representative of 3-4 mice of each group (all on a CB6F1 background), analyzed in two independent experiments.

Consistent with the plausible roles of 4-1BB and OX40 (and also CD27) pathways in inducing Eomes-Granzyme program in T cells, high levels of Eomes and GzmB were expressed in a major population of CD4 cells in day 6-8 CL mice (FIG. 14A). Systemic 4-1BB activation is known to result in selective expression of Eomes, without T-bet expression (Curran et al., 2013), while simultaneous activation of 4-1BB and OX40 induces both Eomes and T-bet in CD4 cells (Qui et al., 2011). Because LMP1-B cells express ligands for both pathways, we also examined T-bet expression in the CD4 cells: analysis of Eomes and T-bet expression by CD4 cells from CL mice revealed three populations of effector cells-Eomes$^+$T-bet$^-$, Eomes$^+$T-bet$^+$, and Eomes$^-$T-bet$^+$—in sharp contrast to CD4 cells from control naïve mice (FIG. 14B). Furthermore, CD4 cells from CL mice expressed GzmB and/or IFN-γ, in contrast to those from control naïve mice (FIG. 14B). GzmB expression depends on Eomes (but not T-bet) (Curran et al., 2013; Qui et al., 2011), while IFN-γ is mainly driven by T-bet (Swain et al., 2012); thus, our FACS analyses revealed three subtypes of effector CD4 cells in CL mice: (i) Eomes/GzmB-featured cytotoxic cells (similar to those described in (Curran et al., 2013)); (ii) T-bet/IFN-γ featured Th1 cells (Swain et al., 2012); (iii) a population that displayed features of both the cells described in (i) and (ii) (these cells were similar to the 'cytotoxic CD4 Th1 cells' described in (Qui et al., 2011)). CD4 cells from CL mice exhibited no expression of GATA3 or RORγt (FIG. 15A-B), indicating no commitment towards the Th2 or Th17 subsets. The co-stimulation pathways may similarly affect CD8 cells (Curran et al., 2013; Qui et al., 2011), but in contrast to their CD4 counterparts, the CD8 cells in day 6-8 CL mice developed into a single, nearly uniform population, that was Eomes$^+$T-bet$^+$GzmB$^+$IFN-γ$^+$ (FIG. 14C).

The finding that LMP1$^+$ B cells efficiently present cellular antigens, and simultaneously provide high levels of co-stimulatory ligands (4-1BBL, OX40L and CD70) that are implicated in cytotoxic T cell programming, suggests that these B cells may suffice, as an APC system, to induce CTL responses to cellular antigens. Indeed, we found that upon a short period (7 days) of co-culture with LMP1$^+$ B cells in vitro (without addition of any exogenous cytokine), a sizable fraction of CD4 T cells from naïve WT mice was activated/ expanded; this effect depended on LMP1 signaling in B cells, as CD4 cells failed to expand on LMP1$^{TM1m}$-expressing B cells (FIG. 16A). A sizable fraction of CD4 cells activated/expanded by LMP1-B cells turned on the Eomes and/or T-het programs (FIG. 16B), developed cytotoxicity (FIG. 16C), and recognized CD40-activated WT B cells in an MHC-II dependent manner (FIG. 16D).

Figure 16H:
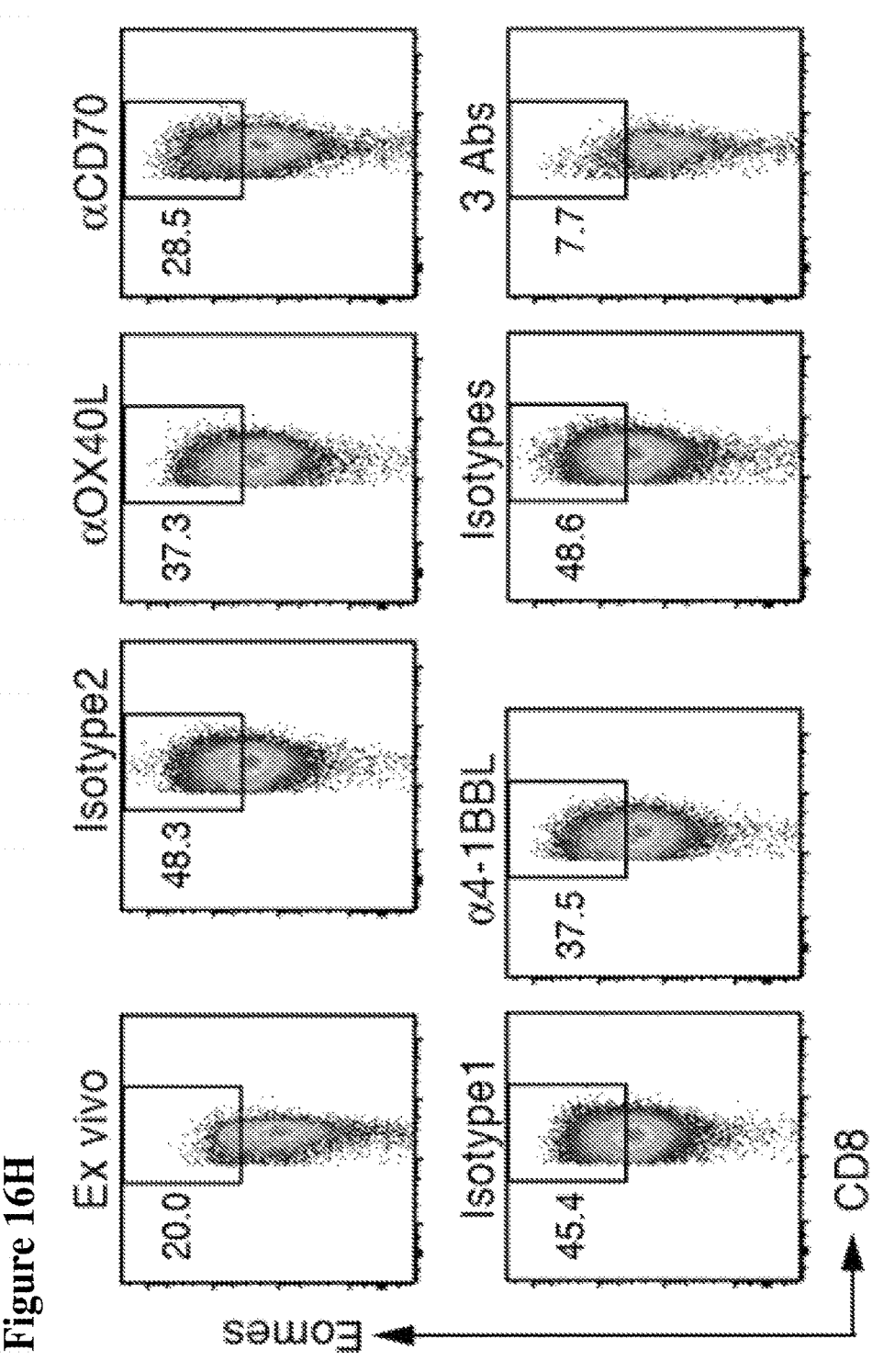
FIG. 16H shows FACS analysis of Eomes expression in CD8 cells either freshly isolated from naïve B6 mice, or after co-culturing for 3 days with LMP1-B cells in the presence of the indicated blocking antibodies or corresponding isotype controls. Representative data from one of triplicate wells are shown, with the frequency of Eomes$^+$ cells in the gate.
Figure 16I:
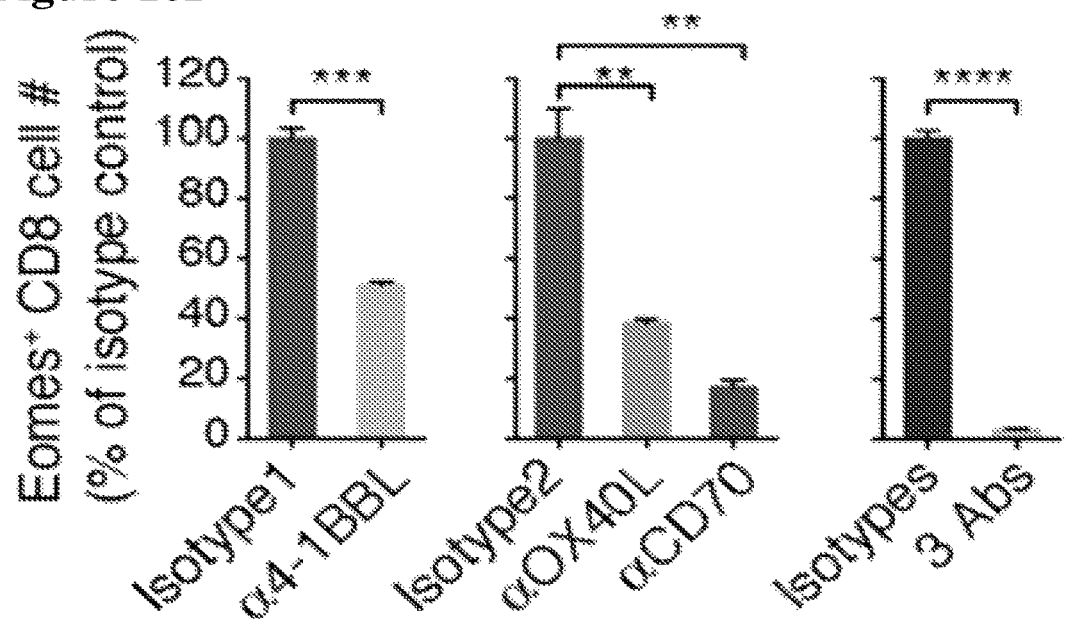
FIG. 16I shows numbers (mean±SEM) of Eomes$^+$ CD8 cells recovered from culture wells treated with the indicated blocking antibodies relative to those from corresponding isotype control treated wells.
Figure 16J:
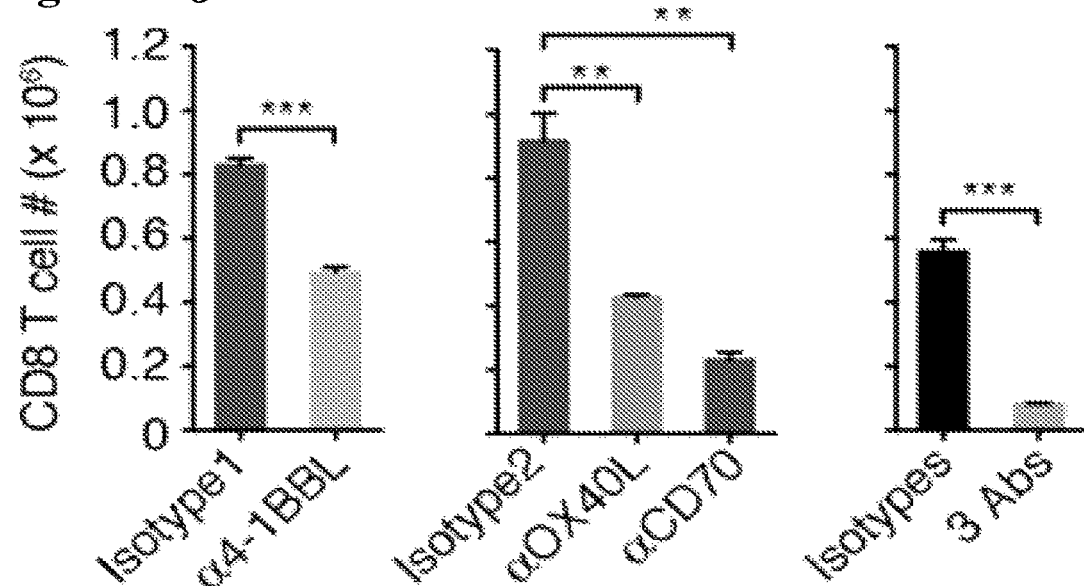
FIG. 16J shows numbers (mean±SEM) of recovered CD8 cells after co-culturing for 3 days with LMP1$^+$ B cells in the presence of the indicated blocking antibodies or corresponding isotype controls. The cell culture was begun with 0.5× 10$^6$ purified CD8 T cells in triplicate wells of 24-well plates.

This in vitro system provided unique opportunities for assessing the roles of 4-1BBL, OX40L and CD70 in the LMP1$^+$ B cell-driven cytotoxic T cell generation. In this system, we observed that, when co-cultured with LMP1$^+$ B cells, CD4 cells gave rise to an optimal Eomes$^+$ population on day 7, while CD8 cells readily differentiated into Eomes$^+$ by day 3. With use of antibody-mediated blocking in culture, we found that 4-1BBL blockade did not alter the fraction of CD4 cells with the Eomes$^+$ phenotype (FIG. 16E), or the absolute number of Eomes$^+$ CD4 cells (FIG. 16F); OX40L blockade led to a slight reduction in the fraction of Eomes$^+$ cells, but a significant decrease in the number; and CD70 blockade caused an even more severe reduction of the fraction and total number of Eomes$^+$ CD4 cells (FIGS. 16E, 16F, and 16G). With regard to their CD8 counterparts, blocking OX40L and CD70 each reduced the frequency and number of the Eomes$^+$ population, to an extent similar to that seen with CD4 cells; however, 4-1BBL blockade also reduced the frequency and significantly decreased the number of Eomes$^+$ CD8 cells (FIGS. 16H, 16I, and 16J), in sharp contrast to the lack of effect seen with the CD4 cells. Furthermore, blocking all three co-stimulatory ligands altogether almost completely abrogated the generation of Eomes$^+$ CD8 cells (FIGS. 16H, 16I, and 16J). Together, these results demonstrate that LMP1-expressing B cells drive the differentiation and expansion of CD4 CTLs via CD70 and OX40L mediated co-stimulation, and of CD8 CTLs via CD70, OX40L, as well as 4-1BBL. CD70 has a more pronounced role in the generation of both types of CTLs.

Overall, our findings indicate that LMP1 signaling turns B cells into highly immunogenic APCs, by enhancing endogenous antigen presentation and potent co-stimulation (via CD70, OX40L and 4-1BBL), and drives cytotoxic CD4 and CD8 T cell responses. The target antigens appear to comprise a large array of LMP1 signaling-induced cellular antigens (see schematic in FIG. 1A).

Example 7. A Novel Concept: LMP1 Signaling Induces Potent Tumor Immunity Mediated by CD4$^+$ and CD8$^+$ Cytotoxic T Cells Against Wide Range of TAAs Our findings presented herein show that LMP1 signaling activates B cells to present cellular antigens and simultaneously provide co-stimulatory signals through CD70, OX40 ligand and 4-1BB ligand, resulting in the induction of cytotoxic CD4 and CD8 T cells that kill LMP1-expressing B cells. This work provides a mechanism whereby T cells can recognize and eliminate EBV-infected or transformed cells via cellular as well as viral antigens.

The polyclonal TCRs on reactive T cells in CL mice indicate that diverse cellular antigens are being targeted. This raises the question of why the virus would evolve a strategy to induce host immune surveillance that target broad cellular antigens. Perhaps, this is favorable for long-term virus-host coexistence. EBV rapidly drives B cell proliferation and transformation, during which LMP1 turns on multiple cellular oncogenic pathways. Meanwhile, LMP1 signaling renders infected cells highly immunogenic, by efficient presentation of viral antigens and LMP1 signaling-induced cellular antigens, and strong co-stimulation for the differentiation of cytotoxic CD8 and CD4 cells (and also Th1 type CD4 cells). Consequently, a much larger TCR repertoire and multiple arms of effector cells are recruited in the immune response, which enables rapid elimination of EBV/LMP1-expressing B cells, and prevents deadly lymphoproliferation and lymphomagenesis. B cells harboring dormant virus are spared, allowing the virus to persist in the host, and efficiently spread in the human population.

Cytotoxic T cells recognize LMP1$^+$ B cells (and LMP1-driven lymphoma cells) through diverse cellular antigens, which appear mainly induced by LMP1 signaling. Because LMP1 is the key oncoprotein for EBV-driven tumorigenesis (Kaye, et al. (1993) Proc Natl Acad Sci USA. 90(19):9150-54), the cellular antigens induced by LMP1 and recognized by T cells would be TAAs belonging to the subgroup of "overexpression antigens" (Coulie et al. (2014) Nat Rev Cancer 14(2):135-46). Our studies presented herein lead us to raise a novel concept: signaling by the Epstein-Barr virus LMP1 protein induces potent tumor immunity mediated by CD4$^+$ and CD8$^+$ cytotoxic T cells against wide range of TAAs. The underlying molecular processes are illustrated in a schematic model in FIG. 1A: In B cells, constitutive LMP1 signaling induces massive cellular gene expression. This leads to upregulation of antigen processing, presenting function (MHCs), strong co-stimulation signals (B7-1, B7-2, ICAM-1, and particularly CD70, OX40L and 4-1BBL), and induced and/or enhanced expression of certain cellular antigens (including a wide range of TAAs). Presentation of these antigens and simultaneous co-stimulations drive activation and cytotoxic differentiation of CD4$^+$ and CD8$^+$ T cells specific to these antigens.

Example 8. T Cell Responses to Exemplary TAAs

Some of the T cell targets presented by LMP1-expressing B cells were also induced in normal B cells upon constitutive CD40 signaling. By microarray, ~2,120 genes were upregulated >2 folds in LMP1-expressing B cells, and ~50% of those genes were also upregulated in CD40-activated B cells. These aberrantly expressed LMP1 signaling-induced cellular antigens included many known TAAs. A few of such TAAs were chosen to demonstrate that LMP1 signaling-induced cellular antigens, particularly TAAs, were indeed T cell target antigens (Table 1). Their potential epitopes bound to MHC-I H-2D$^b$ were either known from literature (for Survivin) or predicted through IEDB (www.immuneepitope.org). Tetramers or Pentamers loaded with a Survivin epitope peptide (ATFKNWPFL) were obtained from the NIH Tetramer Facility or ProImmune Ltd., respectively.

TABLE 1

Examples of LMP1 signaling-induced cellular
genes known as immunogenic TAAs

| | mRNA fold changes relative to naive B cells | |
| --- | --- | --- |
| Gene | LMP1-B | CD40-B |
| p21 | 16.3 | 2.7 |
| Survivin | 7.8 | 3.4 |
| Epha2 | 4.9 | 0.9 |
| Kif20a | 3.9 | 6.9 |

Figure 17:
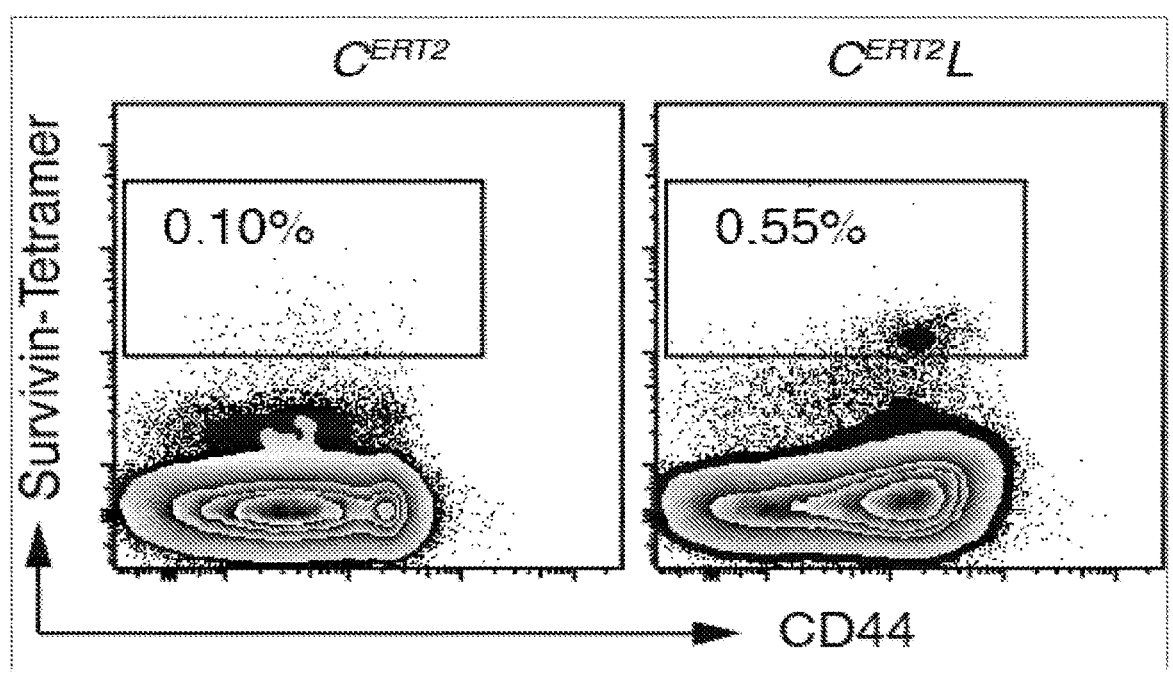
FIG. 17 is a representative flow cytometry analysis that shows detection of specific T cell response to a TAA expressed by LMP1-expressing B cells. CD8 T cells reactive to a Survivin-derived epitope were detected by MHC-I H-2D$^b$ tetramers bearing the Survivin$_{20-28}$ epitope peptide in CD19-cre$^{ERT2}$; LMP1$^{fiSTOP}$ (C$^{ERT2}$L) and CD19-cre$^{ERT2}$ (C$^{ERT2}$) control mice at day 5 following Tamoxifen treatment (to turn on LMP1 expression initially in a small fraction of B cells). The frequencies of Survivin-tetramer$^+$ CD8 T cells are shown within the gates. All mice are on a CB6F1 background.

For detection of TAA-specific T cell response, we used the CD19-cre$^{ERT2}$; LMP1$^{flSTOP}$ (C$^{ERT2}$L) model system. The inducible C$^{ERT2}$L system allows for LMP1 expression to be turned on initially in a small fraction of B cells upon Tamoxifen treatment, thus mimicking primary EBV infection (Yasuda et al., 2013). Flow cytometry analysis with the Survivin-Tetramers (or pentamers) clearly identified a population of CD8 T cells in C$^{ERT2}$L mice which peaked at day 5 after Tamoxifen treatment, but not in treated control mice (FIG. 17 and data not shown). Of note, these T cells have low/medium affinity to the Survivin peptide/MHC complex, as expected for T cells specific to TAAs (Blankenstein et al., 2012); the detection of a small population of T cells recognizing a single Survivin epitope is consistent with the finding that LMP1-expressing B cells elicit polyclonal T cell responses and further strengthens our prediction that wide range of LMP1 signaling-induced cellular antigens/TAAs are targeted by T cells.

Figure 18A:
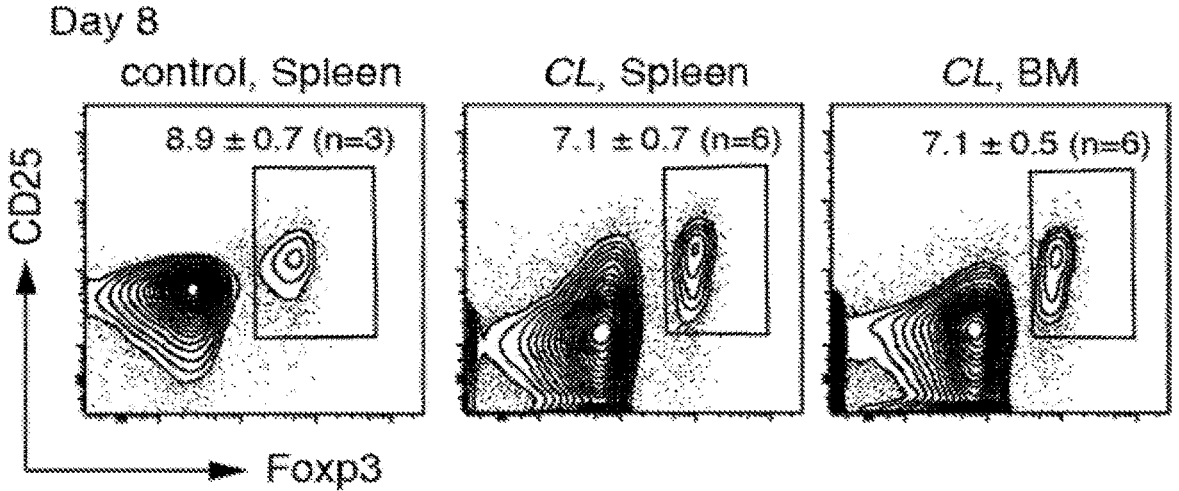
FIG. 18A shows analysis of the frequency of CD4 Tregs (CD25$^+$Foxp3$^+$) in the CD4 T cell compartment in day-8 old CL and control (CD19-cre/+) mice. The percentage (average±SEM) of CD4 Tregs in CD4$^+$ T cells is shown above the gate.
Figure 18B:
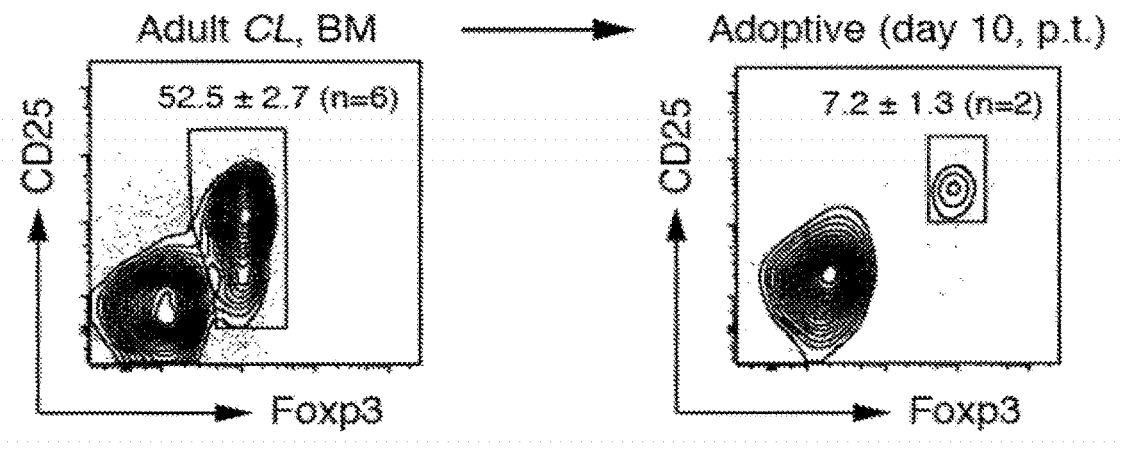
FIG. 18B shows analysis of the frequency of CD4 Tregs in the CD4$^+$ T cells in adult (day 42-84) CL mice BM (left panel) or in recipient mice transplanted with adult CL mice BM CD4$^+$ T cells and LMP1$^+$ lymphoma cells (right panel). CD4$^+$ T cells were recovered from recipients at day 10 post-transfer for FACS analysis.
Figure 18C:
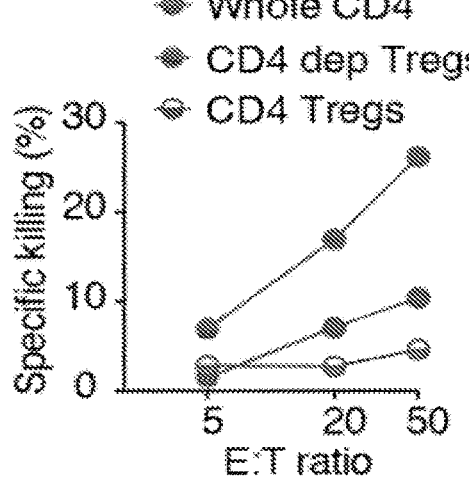
FIG. 18C shows direct killing activity of the indicated T cells isolated from adult Foxp3$^{DTR/GFP}$; CL male mice (on a CB6F1 background), assayed using LMP1$^+$ lymphoma cells as targets. CD4 dep Tregs, CD4 T cells depleted of Tregs.
Figure 18D:
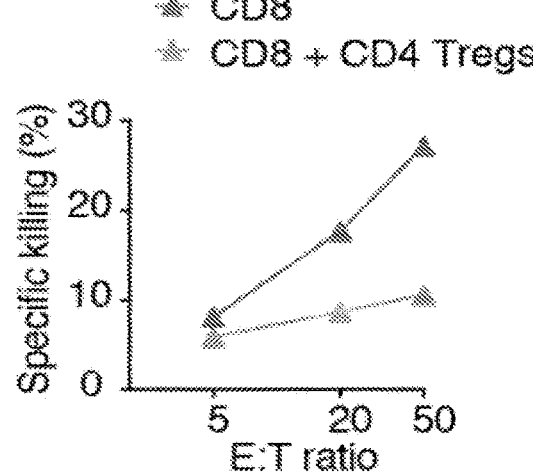
FIG. 18D shows direct killing activity of the CD8 T cells isolated from adult Foxp3$^{DTR/GFP}$; CL male mice (on a CB6F1 background), with or without addition (at 1:1 ratio) of CD4 Tregs from the same mice, assayed using CD40-activated WT B cells (on a B6 background) as targets.

Example 9. Control of Cellular Antigen-Specific T Cells by CD4 Tregs Leads to Immune Homeostasis The broadly autoreactive cytotoxic T cells ensure rapid elimination of LMP1-expressing B cells, but may also damage other host tissues. Importantly, after clearing the first wave of LMP1-expressing B cells, the immune system returns to a homeostatic state, as observed in adult CL mice in which the newly developing LMP1-expressing B cells are under constant surveillance. To understand how the homeostatic state is reached/maintained, we interrogated the role of CD4 Tregs, which are critical players in peripheral tolerance. We found that the frequency of CD4 Tregs was inversely correlated with the killing activity of bulk CD4 cells from CL mice: during the acute phase (day 6-8) of the immune response, CD4 cells displayed a high killing activity (FIG. 4) and a low frequency (~7%) of Tregs (FIG. 18A), whereas during the chronic phase (in adult CL mice BM), CD4 cells exhibited minimum killing activity (FIG. 6) and a strikingly high frequency (~50%) of Tregs (FIG. 18B, left panel); moreover, when co-transferred with LMP1-expressing lymphoma cells into lymphopenic hosts, chronic phase CD4 cells regained killing activity (FIG. 6), and also displayed a sharp decrease of CD4 Tregs (FIG. 18B, right panel). In vitro studies provided direct evidence that CD4 Tregs control the cytotoxicity of CD4 and CD8 effectors in the chronic state: CD4 cells from the BM of adult CL mice exhibited pronounced cytotoxicity on LMP1-expressing B cells, but only after removing CD4 Tregs (FIG. 18C), whereas killing of CD40-activated WT B cells by CD8 cells was suppressed by adding CD4 Tregs to the cell culture (FIG. 18D). Thus, chronic state CD4 Tregs control the autoreactive effector T cells, allowing the effector cells to continuously eliminate newly arising LMP1-expressing B cells, but preventing the destruction of self tissues.

Figure 19A:
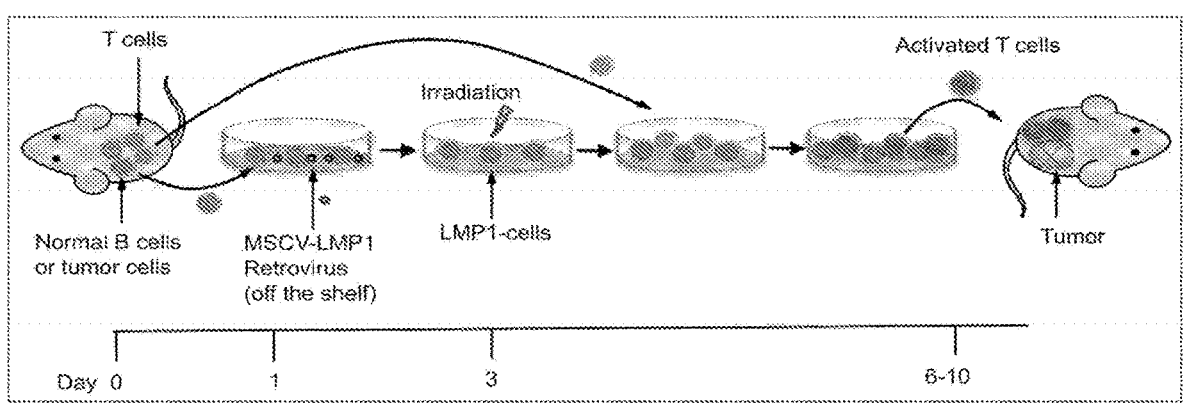
FIG. 19A shows a scheme depicting the use of LMP1-expressing cells to activate/expand T cells for adoptive cell transfer (ACT) therapy for cancers.

Example 10. Use of LMP1-Expressing Cells for Adoptive Cell Transfer (ACT) Therapy Based on the concept that LMP1 expression in primary or lymphoma B cells induces cellular antigen expression and presentation, and elicits cytotoxic T cell responses against LMP1 signaling-induced cellular antigens (including many TAAs), lymphoma inherent TAAs, and neoantigens (FIGS. 1A and 1B), patient-derived primary or lymphoma B cells, upon LMP1 expression, could be used (after irradiation) to activate and expand autologous or donor-derived T cells for ACT to treat EBV-associated B cell lymphomas in immunocompetent hosts and immunosuppressed hosts (e.g., post-transplant and AIDS patients). The EBV-infected lymphoma cells express LMP1, and thus would present the same array of antigens on the surface as the antigens recognized by the infused T cells. The ACT strategy described herein could be similarly applied to EBV-unrelated B cell lymphomas by generating T cells targeting shared LMP1 signaling-induced TAAs, lymphoma inherent TAAs, and neoantigens, thereby eliciting anti-tumor cellular immunity. Other lineages (i.e., non-B lineage) of cells (e.g., tumor cells) expressing LMP1 could also be used in the ACT strategy described herein (FIG. 19A).

Figure 19B:
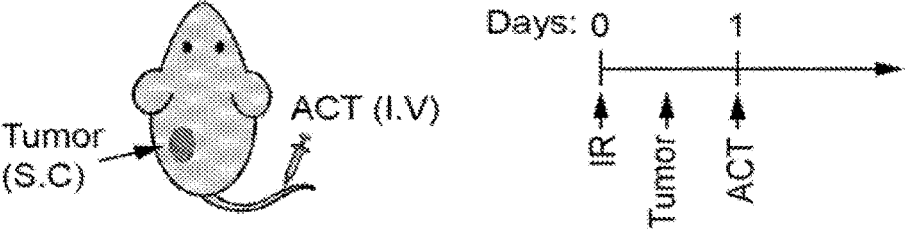
FIG. 19B shows a scheme of ACT in which CD8 and/or CD4 T cells primed by LMP1-expressing B cells are used to treat tumor-bearing mice. Before tumor implantation, mice receive 600 Rad of total body irradiation to create a lymphopenic condition favorable for adoptive T cell expansion.
Figure 19C:
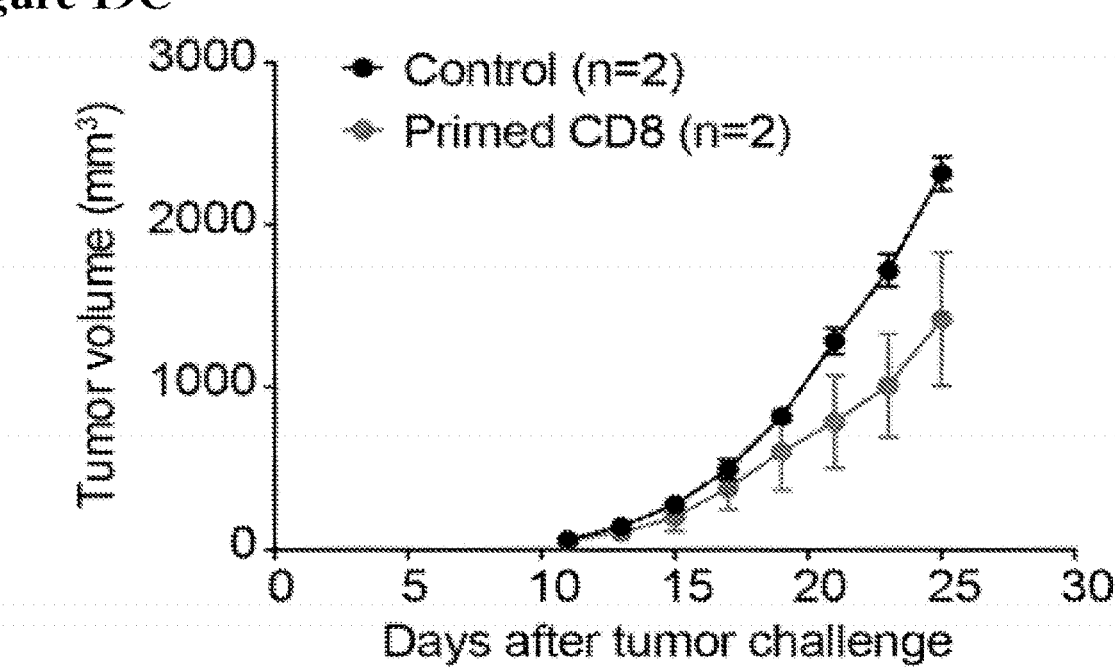
FIG. 19C is a graph showing that ACT of CD8 T cells primed by LMP1-expressing B cells delays tumor (A20) growth. Control mice received no ACT. Error bars represent means±SEM.
Figure 19D:
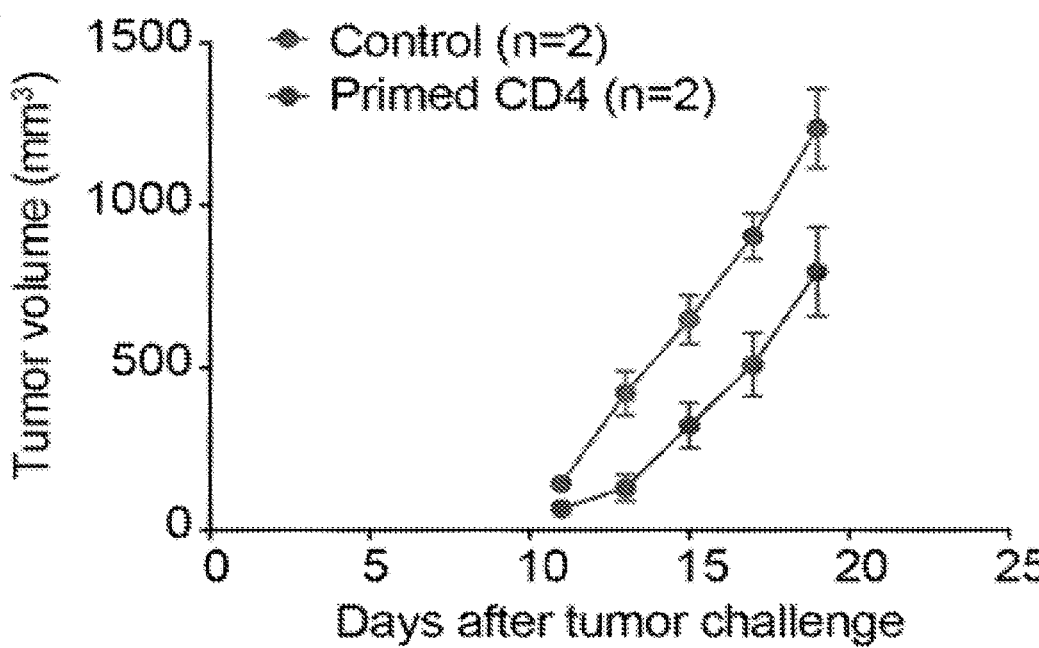
FIG. 19D is a graph showing that ACT of CD4 T cells primed by LMP1-expressing B cells delays tumor (A20) growth. Control mice received no ACT. Error bars represent means±SEM.

To demonstrate use of LMP1-expressing cells for ACT, syngeneic wild-type BALB/c mice were treated with a single dose of irradiation (IR at 600 Rad; to create a lymphopenic condition favorable for adoptive T cell expansion), followed by transplantation of the A20 lymphoma cells ($3 \times 10^5$ cells) on the same day. One day later, $3 \times 10^6$ CD8 T cells primed by LMP1-expressing B cells for 3 days in culture, or $3 \times 10^6$ CD4 T cells primed by LMP1-expressing B cells for 7 days in culture, were administered intravenously to the mice (FIG. 19B). A single dose of CD8 T cells (containing ~50% of Eomes$^+$ cytotoxic effectors) reduced the growth of the A20 lymphoma (FIG. 19C). Similarly, a single dose of CD4 T cells (containing ~10% of Eomes$^+$ cytotoxic effectors) reduced the growth of the A20 lymphoma (FIG. 19D). These results demonstrated that expressing LMP1 in B cells could produce therapeutic T cells against the A20 tumor (through shared TAAs).

Example 11. "LMP1-Cell Vaccine" for Cancer Therapy

Based on the concept that LMP1 expression in primary or lymphoma B cells induces cellular antigens expression, presentation and elicits cytotoxic T cell responses against LMP1 signaling-induced cellular antigens (including many TAAs), lymphoma inherent TAAs, and neoantigens (FIGS. 1A and 1B), LMP1-expressing autologous primary or lymphoma B cells could be used as a "LMP1-cell vaccine" to prime T cells in vivo to treat EBV-associated B cell lymphomas in immunocompetent hosts. The EBV-infected lymphoma cells express LMP1, and thus would present the same array of antigens on the surface as the antigens presented by the LMP1-cell vaccine. Therefore, the T cells activated by the vaccine would exhibit cytotoxicity to the EBV-infected lymphoma cells. The vaccination strategy described herein could be similarly applied to EBV-unrelated B cell lymphomas by eliciting anti-tumor T cell immunity in vivo against shared LMP1 signaling-induced TAAs, lymphoma inherent TAAs, and neoantigens. Other lineages (i.e., non-B lineage) of cells (e.g., tumor cells) expressing LMP1 could also be used for generating LMP1-cell vaccines as described herein (FIG. 20A).

To demonstrate use of a "LMP1-cell vaccine" for cancer therapy in vivo, poorly immunogenic A20 lymphoma and B16-F10 melanoma cell lines were chosen.

A20 lymphoma cells were transduced with wild-type LMP1 or the signaling-dead mutant LMP1$^{TM1m}$ (as control). Syngeneic BALB/c mice were transplanted with $4 \times 10^5$ live A20 lymphoma cells subcutaneously (S.C). Following the transplantation, the mice were vaccinated with A20 cells expressing LMP1 or LMP1$^{TM1m}$ at various time points ($1 \times 10^6$ irradiated cells/S.C.) (FIG. 20B). Vaccination with A20 lymphoma cells expressing wide-type LMP1 markedly delayed A20 lymphoma growth (FIG. 20C).

Figures 20D, 20E:
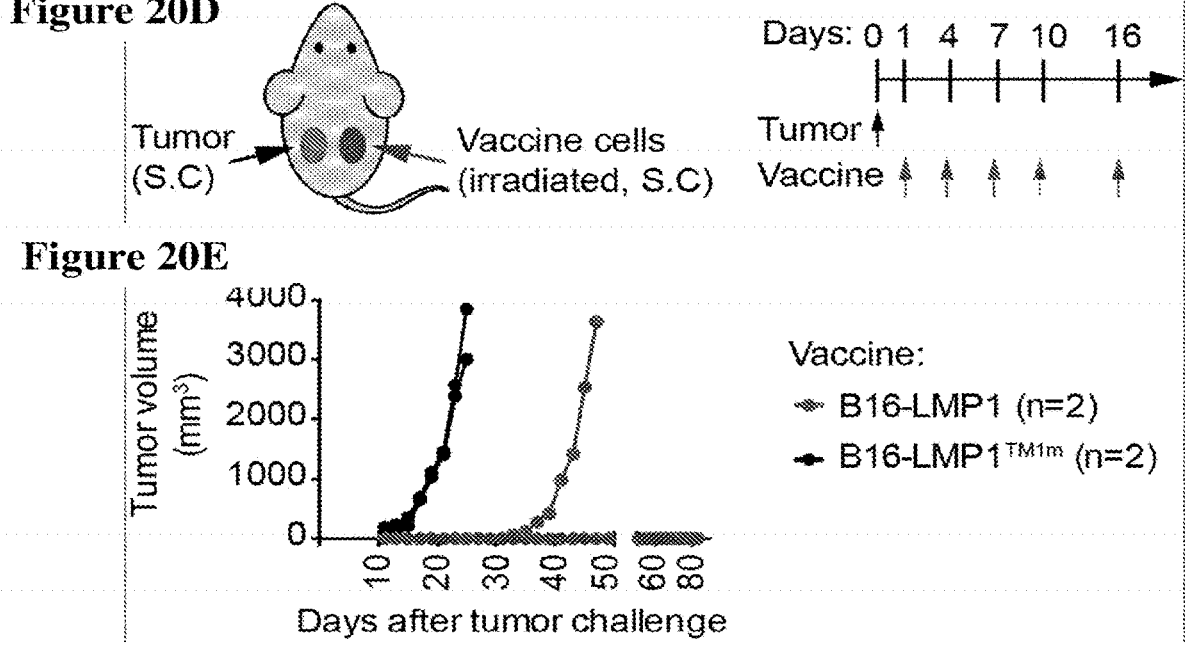
FIG. 20D shows a vaccination scheme in which tumor cells (B16-F10) are transduced to express LMP1 and used as vaccine to treat the unmodified (parental) tumor (melanoma).
FIG. 20E is a graph showing that vaccination with LMP1-expressing B16-F10 melanoma cells markedly delays tumor (melanoma) growth. B16-F10 cells expressing the signaling-dead mutant LMP1$^{TM1m}$ or transduced with the empty vector serve as control vaccine.

B16-F10 melanoma cells were transduced with LMP1, LMP1$^{TM1m}$ or vector control. Syngeneic C57BL6 mice were transplanted with $1 \times 10^5$ live B16-F10 melanoma cells subcutaneously. Following the transplantation, the mice were vaccinated with B16-F10 cells expressing LMP1, LMP1$^{TM1m}$ or vector control at various time points ($1 \times 10^6$ irradiated cells/S.C.) (FIG. 20D). Vaccination with B16-F10 cells expressing wild-type LMP1 markedly delayed or abrogated B16-F10 melanoma tumor growth (FIG. 20E).

These results demonstrated that expressing LMP1 in otherwise poorly immunogenic A20 and B16 tumor cells could turn them into a powerful therapeutic vaccine against the respective unmodified (parental) tumors.

---

The invention claimed is:

1. A method of treating a subject having a B cell cancer or melanoma, the method comprising administering to the subject a LMP1-cell vaccine comprising an isolated neoplastic B cell, an isolated leukemia B cell, or an isolated melanoma cell expressing a nucleic acid vector encoding a LMP1 polypeptide having a sequence that is at least 90% identical to SEQ ID NO: 1, wherein at least 50% of an Epstein-Barr virus (EBV) genome is absent from the vector, and wherein the method treats the B cell cancer or melanoma in the subject.

2. The method of claim 1, wherein the LMP1-cell vaccine comprises the isolated neoplastic B cell, and the method further comprises irradiating the isolated neoplastic B cell.

3. The method of claim 1, wherein the LMP1-cell vaccine comprises the isolated neoplastic B cell, and the method further comprises administering to the subject:
   (a) an adjuvant; or
   (b) an immune co-stimulation therapy selected from the group consisting of an agonist of CD27, an agonist of OX40, and an agonist of 4-1BB; or
   (c) an immune checkpoint targeting therapy; or
   (d) a Treg modulating therapy.

4. The method of claim 1, wherein the LMP1-cell vaccine comprises the isolated neoplastic B cell.

5. The method of claim 1, wherein the LMP1-cell vaccine comprises the isolated neoplastic B cell, wherein the isolated neoplastic B cell is isolated from a subject with a pathology selected from the group consisting of Hodgkin's lymphoma, Burkitt's lymphoma, an AIDS-associated B cell lymphoma, a central nervous system lymphoma, and a diffuse large B cell lymphoma.

6. The method of claim 1, wherein the LMP1-cell vaccine comprises the isolated neoplastic B cell, wherein the method treats a B cell cancer in the subject.

7. The method of claim 1, wherein the LMP1-cell vaccine comprises the isolated leukemia B cell, and the method further comprises irradiating the isolated leukemia B cell.

8. The method of claim 1, wherein the LMP1-cell vaccine comprises the isolated leukemia B cell, and the method further comprises administering to the subject:
   (a) an adjuvant; or
   (b) an immune co-stimulation therapy selected from the group consisting of an agonist of CD27, an agonist of OX40, and an agonist of 4-1BB; or
   (c) an immune checkpoint targeting therapy; or
   (d) a Treg modulating therapy.

9. The method of claim 1, wherein the LMP1-cell vaccine comprises an isolated leukemia B cell.

10. The method of claim 1, wherein the LMP1-cell vaccine comprises the isolated leukemia B cell, and wherein the method treats leukemia in the subject.

11. The method of claim 1, wherein the LMP1-cell vaccine comprises the isolated melanoma cell, and the method further comprises irradiating the isolated melanoma cell.

12. The method of claim 1, wherein the LMP1-cell vaccine comprises the isolated melanoma cell, and the method further comprises administering to the subject:
   (a) an adjuvant; or
   (b) an immune co-stimulation therapy selected from the group consisting of an agonist of CD27, an agonist of OX40, and an agonist of 4-1BB; or (c) an immune checkpoint targeting therapy; or (d) a Treg modulating therapy.

13. The method of claim 1, wherein the LMP1-cell vaccine comprises an isolated melanoma cell.

14. The method of claim 1, wherein the LMP1-cell vaccine comprises the isolated melanoma cell, wherein the method treats melanoma in the subject.

15. The method of claim 1, wherein the LMP1-cell vaccine comprises the isolated melanoma cell, wherein the isolated melanoma cell is a B16 melanoma cell.

\*    \*    \*    \*    \*